(12) United States Patent
Cherrington et al.

(10) Patent No.: US 11,357,829 B2
(45) Date of Patent: Jun. 14, 2022

(54) SYSTEMS, COMPOSITIONS AND METHODS FOR TREATING DIABETES

(71) Applicant: Vanderbilt University, Nashville, TN (US)

(72) Inventors: Alan Cherrington, Nashville, TN (US); David Maggs, Boston, MA (US); Soumitra Ghosh, San Diego, CA (US); Christopher A. Rhodes, San Diego, CA (US); Jui-Chen Lin, San Diego, CA (US)

(73) Assignee: Vanderbilt University, Nashville, TN (US)

( * ) Notice: Subject to any disclaimer, the term of this patent is extended or adjusted under 35 U.S.C. 154(b) by 23 days.

(21) Appl. No.: 16/483,033

(22) PCT Filed: Feb. 2, 2018

(86) PCT No.: PCT/US2018/016647
§ 371 (c)(1),
(2) Date: Aug. 1, 2019

(87) PCT Pub. No.: WO2018/144867
PCT Pub. Date: Aug. 9, 2018

(65) Prior Publication Data
US 2020/0230211 A1    Jul. 23, 2020

Related U.S. Application Data

(60) Provisional application No. 62/454,613, filed on Feb. 3, 2017.

(51) Int. Cl.
| | |
|---|---|
| *A61K 38/00* | (2006.01) |
| *A61K 38/28* | (2006.01) |
| *A61P 3/10* | (2006.01) |
| *A61K 38/26* | (2006.01) |
| *A61K 47/10* | (2017.01) |
| *A61K 47/20* | (2006.01) |
| *A61K 47/32* | (2006.01) |
| *A61K 9/00* | (2006.01) |

(52) U.S. Cl.
CPC .............. *A61K 38/28* (2013.01); *A61K 38/26* (2013.01); *A61K 47/10* (2013.01); *A61K 47/20* (2013.01); *A61K 47/32* (2013.01); *A61P 3/10* (2018.01); *A61K 9/0019* (2013.01)

(58) Field of Classification Search
None
See application file for complete search history.

(56) References Cited

U.S. PATENT DOCUMENTS

| | | |
|---|---|---|
| 5,321,008 A | 6/1994 | Beaumont et al. |
| 6,540,982 B1 | 4/2003 | Adjei et al. |
| 7,314,859 B2 | 1/2008 | Green et al. |
| 7,642,232 B2 | 1/2010 | Green et al. |
| 7,655,618 B2 | 2/2010 | Green et al. |
| 2006/0014670 A1 | 1/2006 | Green et al. |
| 2009/0124559 A1 | 5/2009 | Bachovchin et al. |
| 2012/0035105 A1 | 2/2012 | Geho et al. |
| 2012/0232001 A1 | 9/2012 | Prestrelski et al. |
| 2016/0022899 A1 | 1/2016 | Aljohani |

FOREIGN PATENT DOCUMENTS

| | | |
|---|---|---|
| JP | 2016512255 A | 4/2016 |
| WO | 2006004696 A2 | 1/2006 |

OTHER PUBLICATIONS

Ubukata et al. Diabetes Research and Clinical Practice 24, 1996, 1-6.*
European Patent Office Examination Report for Application No. 18747931.6 dated Jun. 7, 2021 (8 pages).
International Search Report and Written Opinion for related Application No. PCT/US18/16647 dated Apr. 6, 2018 (10 pages).
Cherrington et al., "The Role of Insulin and Glucagon in the Regulation of Basal Glucose Production in the Postabsorptive Dog", The Journal of Clinical Investigation, vol. 58, Dec. 1976, pp. 1407-1418.
Edgerton et al., "Changes in Glucose and Fat Metabolism in Response to the Administration of a Hepato-Preferential Insulin Analog", Diabetes, vol. 63, Nov. 2014, pp. 3946-3954.
"Chapter 2: The endocrine pancreas" Endocrinology, NCBI Bookshelf, Mar. 2018, 29 pages.
Russell et al., "Outpatient Glycemic Control with a Bionic Pancreas in Type 1 Diabetes", The New England Journal of Medicine, 371;4, Jun. 15, 2014, pp. 313-325.
Bakhtiani et al., "A review of artificial pancreas technologies with an emphasis on bi-hormonal therapy", Diabetes, Obesity and Metabolism 15:1065-1070, 2013.
Steiner et al., "Effects of Insulin on Glucagon-Stimulated Glucose Production in the Conscious Dog", Metabolism, vol. 39, No. 12, pp. 1325-2133, 1990.
Rivera et al., "Insulin-induced hypoglycemia increases hepatic sensitivity to glucagon in dogs", Journal of Clinical Investigation, vol. 120 No. 12, 2010, pp. 4425-4435.
Day et al., "A new glucagon and GLP-1 co-agonist eliminates obesity in rodents", Nature Chemical Biology, vol. 5, No. 10, Oct. 2008, pp. 749-757.
European Patent Office Extended Search Report for Application No. 18747931.6 dated Oct. 6, 2020 (10 pages).
Gough et al., "Insulin degludec/liraglutide (IDegLira) for the treatment of type 2 diabetes", Expert Review of Endocrinology & Metabolism, vol. 11, No. 1, 2015, pp. 7-19.

(Continued)

*Primary Examiner* — Jeanette M Lieb
(74) *Attorney, Agent, or Firm* — Michael Best & Friedrich LLP

(57) ABSTRACT

This disclosure provides methods for treatment comprising co-administering insulin and glucagon to a subject, and co-formulations comprising insulin and glucagon.

23 Claims, 74 Drawing Sheets

(56) References Cited

OTHER PUBLICATIONS

Julia et al., "When should fixed ratio basal insulin/glucagon-like peptide-1 receptor agonists combination products be considered?", Journal of Diabetes and its Complications, vol. 33, No. 12, Oct. 2019, 5 pages.

Japanese Patent Office Notice of Reasons for Refusal for Application No. 2019-542088 dated Oct. 15, 2021 (7 pages including English translation).

* cited by examiner

Hyperglycemic-Hyperinsulinemic

SUBJECT 8: OMNIPOD Delivery

Basal
.4 mU / kg / min INS
2.0 ng / kg / min GGN

4 FOLD
INS : 1.6 mU / kg / min
Glucose (Pe) : 10 mg / kg / min
GGN : 2.0 ng / kg / min
or GGN : 8.0 ng / kg / min I/G ratio
16 or 4

SUBJECT 9 & 10: Microdialysis Delivery

Basal
.4 mU / kg / min INS
2.0 ng / kg / min GGN

4 FOLD
INS : 1.6 mU / kg / min
Glucose (Pe) : 10 mg / kg / min
GGN : 2.0 ng / kg / min
or GGN : 8.0 ng / kg / min I/G ratio
16 or 4

FIG. 42

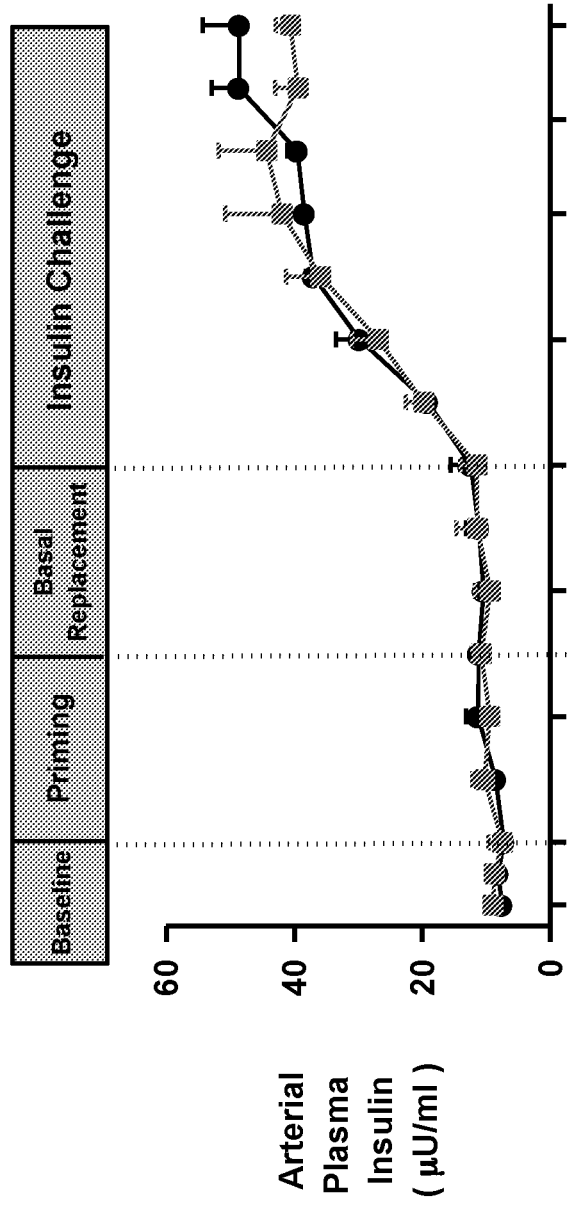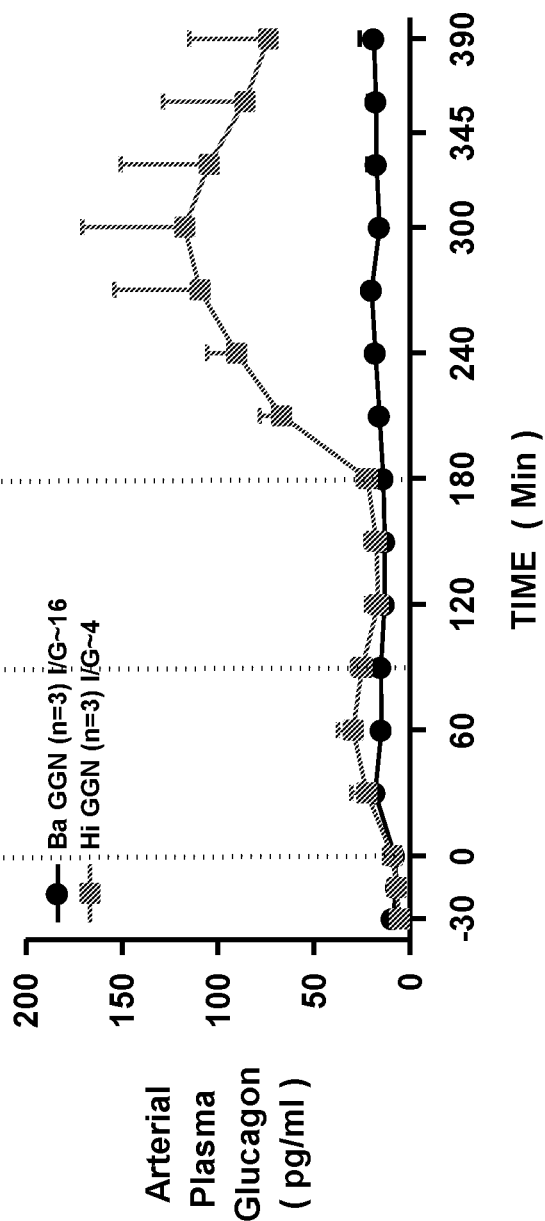

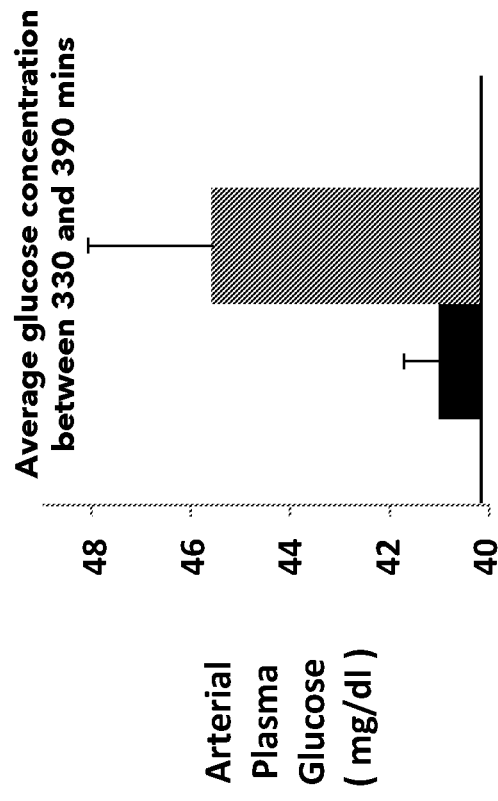
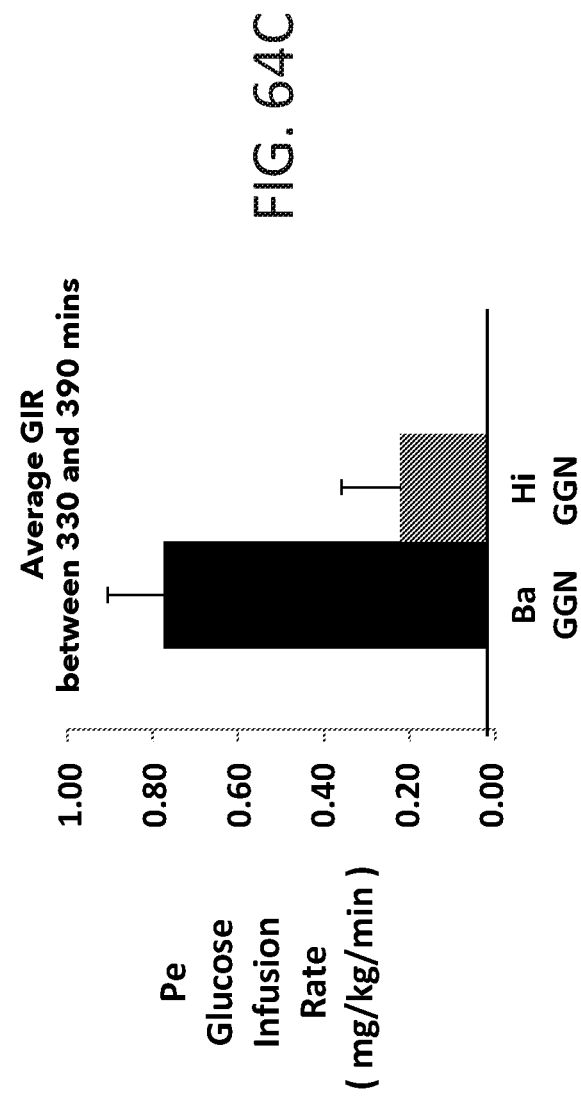
FIG. 64B
FIG. 64C

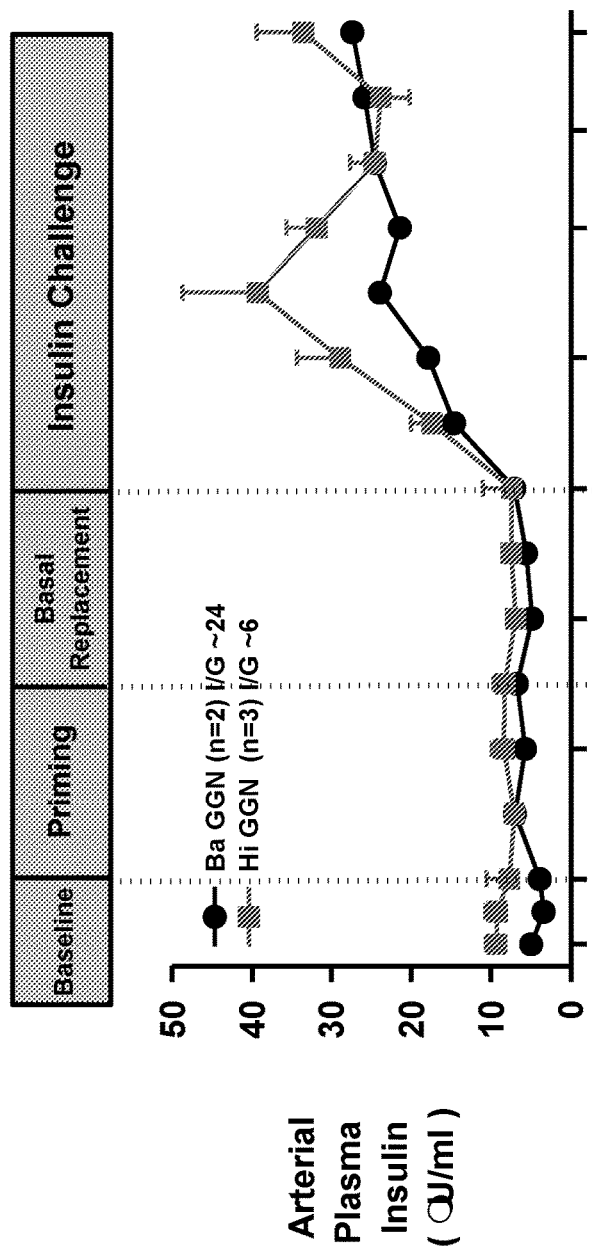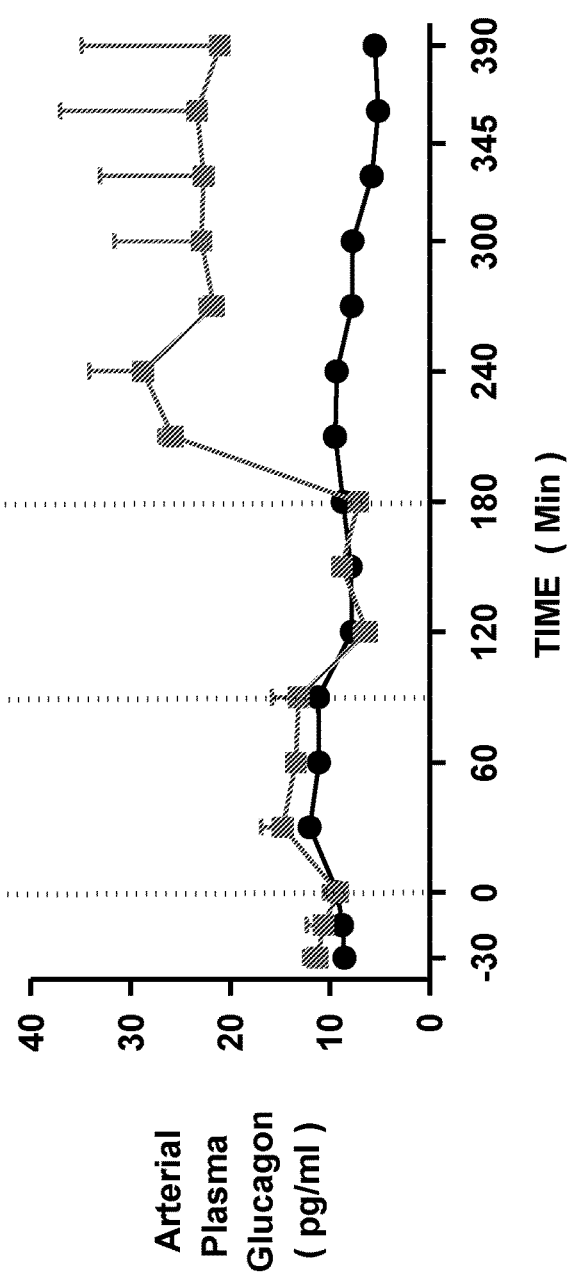

FIG. 70
| Lot No. | Insulin (mg/mL) | Glucagon (mg/mL) |
|---|---|---|
| AB-160003-01 | 4.48 | 0.83 |
| AB-160002-01 | 4.48 | 0.21 |
| AB-160001-01 | 1.08 | 0.21 |
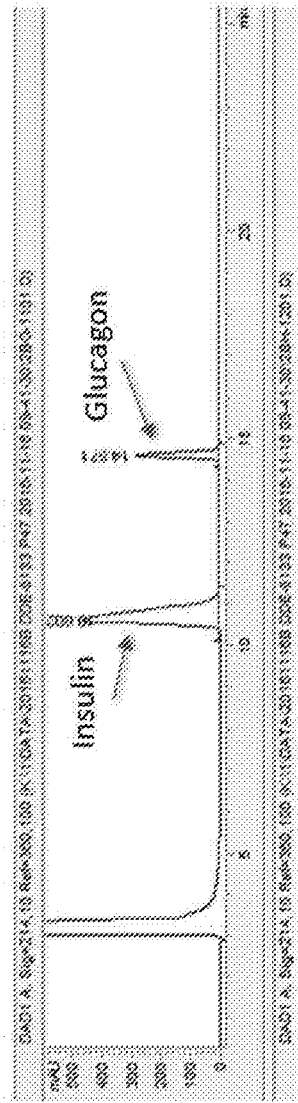
FIG. 70A
AB-160003-01
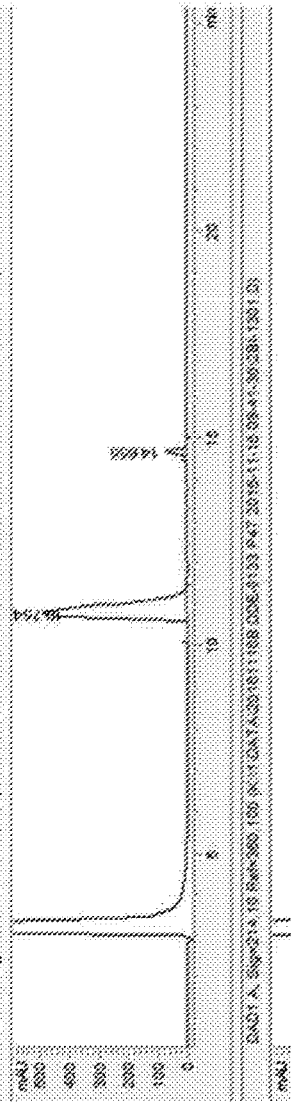
FIG. 70B
AB-160002-01
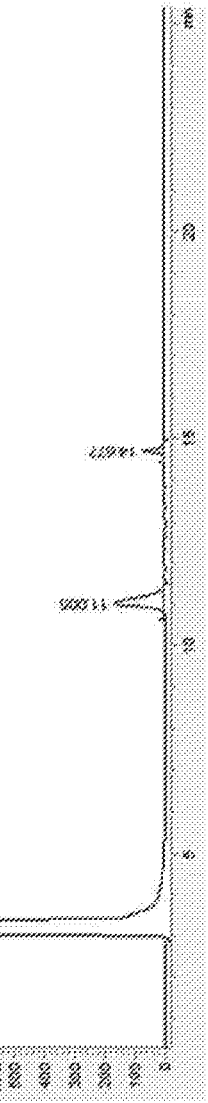
FIG. 70C
AB-160001-01

FIG. 72A

75 – 95% (v/v) Aqueous

| Buffer | Co-Solvent | | | | | Insulin (mg/mL) | Glucagon (mg/mL) |
| --- | --- | --- | --- | --- | --- | --- | --- |
| | 5% TPGS | 10% DMSO | 10% NMP | 10% PG | 10% Glycerol | | |
| PBS 7.8 | X | | | | | 1.38* | 0.25* |
| PBS 7.8 | X | | X | | | 3.3 | 0.07 |
| PBS 7.8 | X | | | X | | 0.7 | 0.11 |
| PBS 7.8 | X | | | X | | 1 | 0.25 |
| PBS 7.8 | X | X | | | X | 1.3 | 0.02 |

FIG. 72B 34.5 – 35.5 % (v/v) Aqueous

| 34.5-35.5% Buffer (20 mM) | Solvent (v/v/v) | | | | | 1% EDTA | Insulin (mg/mL) | Glucagon (mg/mL) |
| --- | --- | --- | --- | --- | --- | --- | --- | --- |
| | 4.5% TPGS | 30% DMSO | 30% NMP | 30% PG | 30% Glycerol | | | |
| PB 7.8 | X | | X | X | | | ≥6.55 | 0.30 |
| PB 7.8 | X | X | X | | X | | ≥6.26 | 0.07 |
| PB 7.8 | X | X | | X | | | ≥4.46 | 0.57 |
| PB 7.8 | X | X | | X | X | X | 3.83 | 0.72 |
| PB 7.8 | X | | | X | X | X | 3.33 | 0.30 |
| PB 7.8 | X | | X | | X | X | ≥4.25 | 0.06 |

30 – 40% (v/v) Phosphate Buffer

| ID | Solution Composition | Insulin (mg/mL) | Glucagon (mg/mL) |
|---|---|---|---|
| 6 | 20 mM PB, with 30% NMP, 30% PG | 5.48 | 0.32 |
| 7 | 20 mM PB, with 33% NMP, 33% glycerol | 5.62 | 0.21 |
| 9 | 20 mM PB, with 30% DMSO, 30% PG | 5.79 | 0.19 |
| 10 | 20 mM PB, with 30% DMSO, 30% glycerol | 5.72 | 0.11 |
| 11 | 20 mM PB, with 50% DMSO, 20% PG | 5.53 | 0.36 |
| 12 | 20 mM PB, with 40% DMSO, 20% PG | 4.15 | 0.33 |

FIG. 73

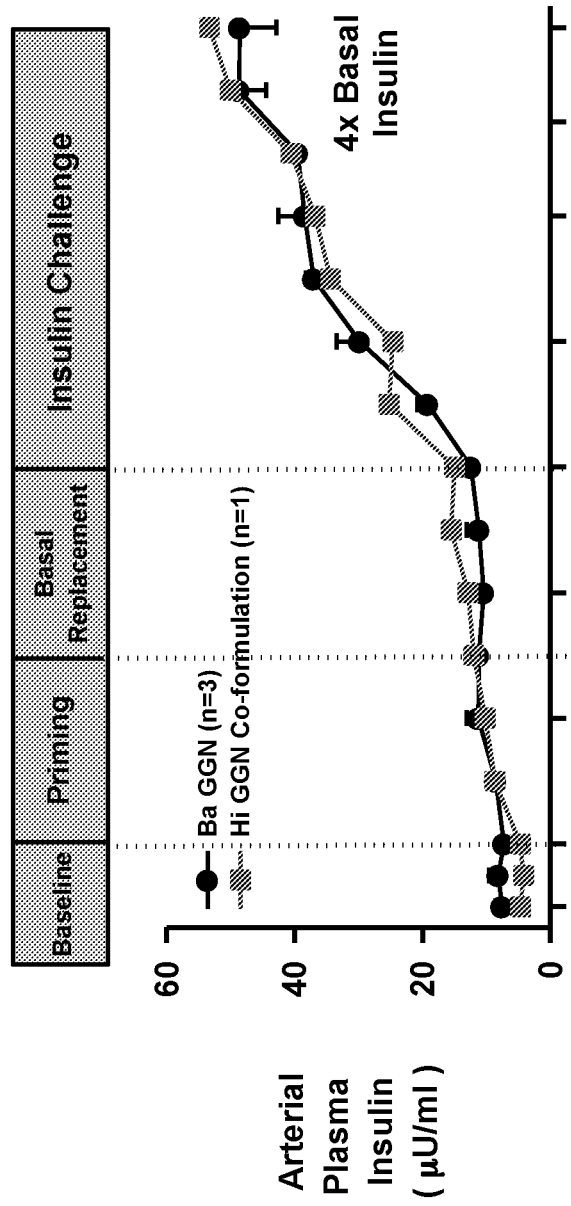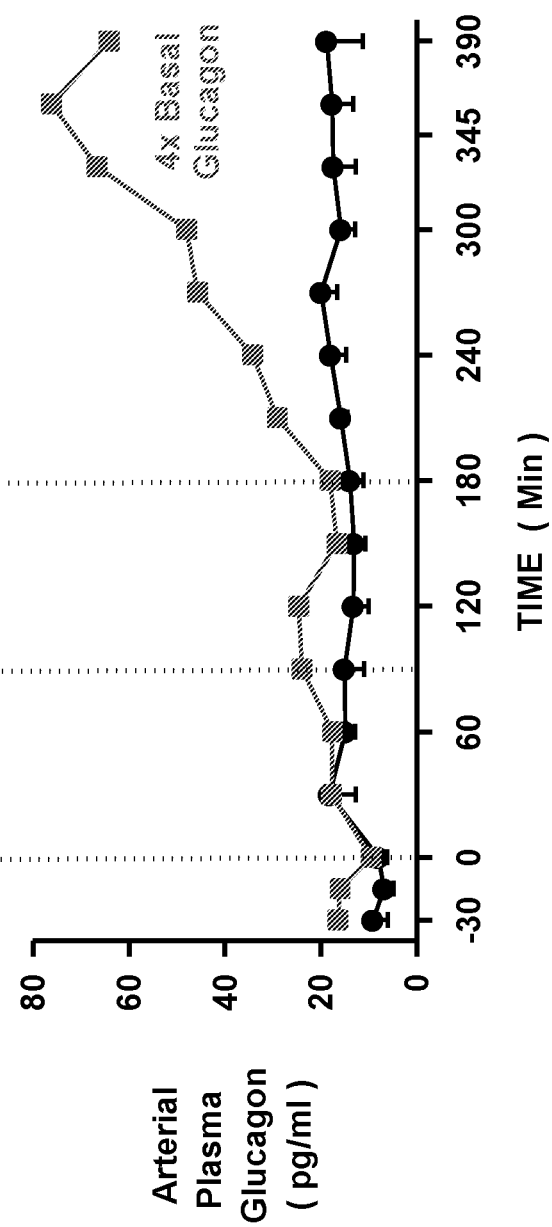

SYSTEMS, COMPOSITIONS AND METHODS FOR TREATING DIABETES

CROSS REFERENCE TO RELATED APPLICATIONS

This patent application is the U.S. national stage entry, under 35 U.S.C. § 371, of International Application Number PCT/2018/016647, filed Feb. 2, 2018, which claims the benefit of U.S. Provisional Application No. 62/454,613, filed Feb. 3, 2017, the entire contents of each of which are hereby incorporated by reference.

FIELD

The present disclosure provides systems, compositions and methods for treatment of a diabetic patient, and in particular to treatments including the co-administration of insulin and glucagon.

BACKGROUND

Treatment of a diabetic patient often includes delivery of insulin, such as via injections via syringe or an insulin delivery pump. Hypoglycemia is the complication feared most by patients with T1DM. It is a major barrier to effective treatment because people under-dose insulin so as to avoid hypoglycemia. As a result, current treatments often result in inadequate glycemic control, involving undesired hypoglycemic and/or hyperglycemic events.

There is a need for systems, compositions, and methods that treat diabetic patients while reducing oscillations in blood glucose and hypoglycemic episodes.

SUMMARY

Embodiments of the systems, devices and methods described herein can be directed to systems, devices and methods for treatment of a diabetic patient.

In some aspects, the present disclosure provides methods of treatment comprising co-administering insulin and glucagon to a subject, wherein the insulin and glucagon are co-administered at an insulin:glucagon molar ratio between about 1:1 and about 6:1, and wherein the insulin and glucagon are administered in an amount therapeutically effective to simultaneously treat or inhibit hyperglycemia and to inhibit hypoglycemia. For example, the insulin and glucagon may be co-administered at an insulin: glucagon molar ratio between about 1:1 and about 5:1, between about 3:1 and about 6:1, or between about 3:1 and about 5:1. The subject may be hyperglycemic prior to co-administering the insulin and the glucagon. In some embodiments, co-administering the insulin and the glucagon may comprise administering to the subject a co-formulation comprising insulin and glucagon. The co-formulation may comprise insulin at a concentration between about 1 mg/ml and about 10 mg/ml, and glucagon at a concentration between about 0.1 mg/ml and about 1 mg/ml. For example, the co-formulation may comprise insulin at a concentration between about 3 mg/ml and about 5 mg/ml, and glucagon at a concentration between about 0.1 mg/ml and about 0.8 mg/ml. The co-formulation may comprise a solvent that includes at least one non-aqueous solvent (e.g., an aprotic solvent, such as dimethyl sulfoxide and/or N-methylpyrrolidone). In some embodiments, between about 20% and about 60% of the solvent (v/v) consists of the one or more non-aqueous solvents. The solvent further may include one or more aqueous solvents. In some embodiments, no more than about 40% of the solvent (v/v) consists of the one or more aqueous solvents. In some embodiments, between about 10% and about 40% of the solvent (v/v) is propylene glycol (PG), glycerol or a combination of PG and glycerol. The co-administering of the insulin and the glucagon may comprise administering the insulin and the glucagon subcutaneously. Co-administering the insulin and glucagon may comprise administering insulin at a basal infusion rate of approximately 0.2-0.6 mU/kg/minute and administering glucagon at a basal infusion rate of approximately 1-4 ng/kg/minute. For example, the insulin may be administered at a basal infusion rate of approximately 0.3-0.5 mU/kg/minute, and/or the glucagon may be administered at a basal infusion rate of approximately 2-3 ng/kg/minute.

In some aspects, the present disclosure provides co-formulations comprising insulin at a concentration between about 1 mg/ml and about 10 mg/ml, and glucagon at a concentration between about 0.1 mg/ml and about 1 mg/ml, wherein the molar ratio of insulin:glucagon is between about 1:1 and about 6:1. For example, the molar ratio of insulin: glucagon may be between about 1:1 and about 5:1, between about 3:1 and about 6:1, or between about 3:1 and about 5:1. The insulin may be at a concentration between about 3 mg/ml and about 5 mg/ml, and the glucagon may be at a concentration between about 0.1 mg/ml and about 0.8 mg/ml. The co-formulations may further comprise a solvent that includes one or more aqueous solvents and one or more non-aqueous solvents (e.g. an aprotic solvent such as DMSO and/or NMP). In some embodiments, between about 20% and about 60% of the solvent (v/v) may consist of the one or more non-aqueous solvents. The solvent further may include one or more aqueous solvents. In some embodiments, no more than about 40% of the solvent (v/v) may consist of the one or more aqueous solvents. In some embodiments, between about 10% and about 40% of the solvent may be propylene glycol (PG), glycerol, or a combination of PG and glycerol.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

FIGS. 17-46 illustrate data from mammalian studies conducted by applicant, consistent with the present inventive concepts.

FIGS. 63-65 illustrate data from mammalian studies conducted by applicant to assess the ability of a co-infusion of insulin and glucagon to replace basal endogenous secretion of the two hormones while still maintaining euglycemic, consistent with the present inventive concepts.

FIGS. 68 and 69 illustrate data from mammalian studies conducted by applicant to assess the ability of an insulin infusion at a rate of 0.4 mU/kg/min and a glucagon infusion at a rate of 1.38 ng/kg/min to effectively replace basal secretion of insulin and glucagon and to limit insulin-induced hypoglycemia, consistent with the present inventive concepts.

FIGS. 70-73 illustrate data from mammalian studies conducted by applicant to support the development of a non-aqueous co-formulation of insulin and glucagon for use in infusion pumps that is stable at 2-8° C., consistent with the present inventive concepts.

FIGS. 74-76 illustrate data from mammalian studies conducted by applicant to assess the therapeutic value of a co-formulation of an insulin and glucagon solution as compared to insulin and glucagon as separate solutions, consistent with the present inventive concepts.

DETAILED DESCRIPTION

Figure 1:
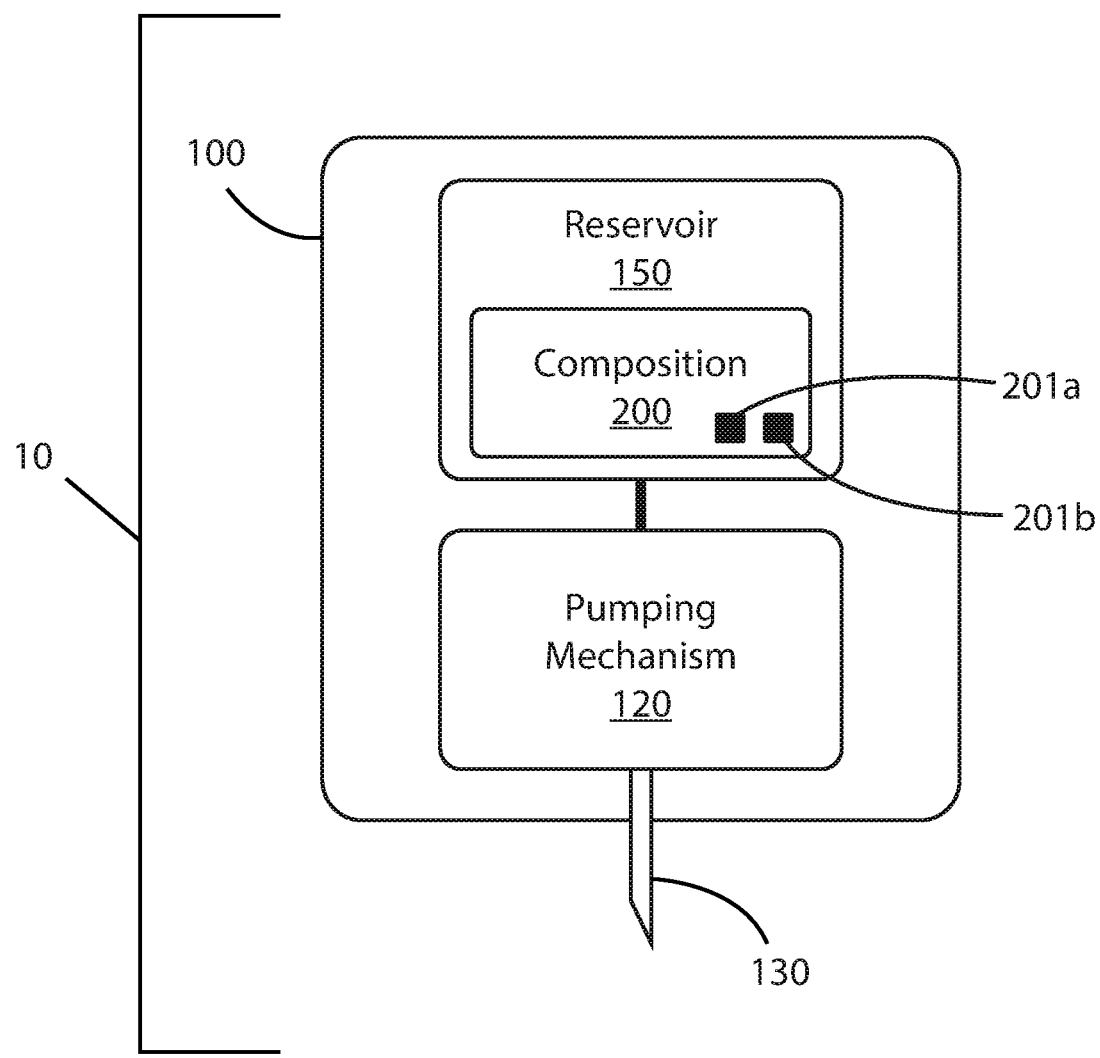
FIG. 1 illustrates a system for delivering a composition to a patient, comprising a single pumping device with a single reservoir, consistent with the present inventive concepts.

Reference will now be made in detail to the present embodiments of the technology, examples of which are illustrated in the accompanying drawings. The same reference numbers are used throughout the drawings to refer to the same or like parts.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate" shall include locations relatively close to, on, in and/or within a referenced component or other location.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "insulin" where used herein shall include the hormone insulin and/or any one or more insulin analogues (e.g. one or more insulin analogues known to one of skill in the art), such as NPH insulin, insulin aspart, insulin glulisine, insulin lispro, and/or hepato-preferential insulin.

The term "glucagon" where used herein shall include the hormone glucagon and/or one or more glucagon analogues (e.g. one or more glucagon analogues known to one of skill in the art), such as Dasiglucagon (also known as ZP-4207, Zealand Pharmaceuticals), [Asp28] glucagon, [Asp28, Glu29] glucagon, [Asp28, Glu29] glucagon, and/or glucagon-Cex.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any suitable sub-combination. For example, it will be appreciated that all features set out in any of the claims (whether independent or dependent) can be combined in any given way.

Provided herein are systems, compositions and methods for treating a diabetic patient, such as by delivering both insulin and glucagon simultaneously, or at least relatively simultaneously ("simultaneously" or "at the same time" herein). For example, simultaneous delivery includes sequential delivery of a volume of a first agent (e.g. insulin) and a volume of a second agent (e.g. glucagon), delivered in either order, that occurs within a time period of between 0.1 seconds and 90 minutes, a time period of between 0.1 seconds and 60 minutes, or a time period of between 0.1 seconds and 30 minutes.

Modification of insulin can be performed to mitigate the risk of iatrogenic hypoglycemia in order to improve treatment of the diabetic patient. By developing a hypoglycemia safe insulin, one could titrate up the insulin dose and by doing so lessen the lows and highs in plasma glucose. More modulated oscillations in the plasma glucose is a highly desired outcome in T1DM treatment, and should lead to an improvement in HbA1c and a reduction in the other complications. Glucagon and insulin have opposing effects on glucose metabolism in the liver and glucagon injection has long been used to overcome hypoglycemia resulting from an over-dose of insulin. Glucagon is known to be the first hormone responder when the plasma glucose level is low. In a non-diabetic individual, glucagon secreted in response to hypoglycemia stimulates glucose production and thereby limits fall in plasma glucose. In the individual with Type 1 diabetes mellitus (T1DM), the alpha cell is dysfunctional (the cellular source of glucagon) and glucagon does not rise in response to hypoglycemia, thus placing a greater burden on the autonomic nervous system which as a result may itself fail.

Under euglycemic/hyperglycemic conditions insulin (I) overpowers glucagon (G) action on the liver (Steiner, et al, in Metabolism, 1990) such that at a given I/G molar ratio insulin will dominate glucagon when the infusion rates of both rise. On the other hand, glucagon is much more effective in competing with insulin under hypoglycemic conditions. Systems, devices and methods of the present inventive concepts combine insulin and glucagon at a desirable molar ratio as a therapeutic modality, to lessen the extent to which insulin induces hypoglycemia, while retaining the ability for insulin to control hyperglycemia. The delivery of the two peptide hormones could be by simultaneous co-administration of their individual formulations, or by administration of a co-formulation of the peptide hormones. In this way, the administered glucagon compensates for the deficient alpha cell response lessening the demand on the autonomic nervous system. This combination provides hypoglycemic buffering while having little or no effect on glucose tolerance. Applicant has conducted in vivo experiments, described below, in which particular ratios of insulin and glucagon were simultaneously delivered, both intravenously and into subcutaneous tissue, to support this desired therapeutic result.

Referring now to FIG. 1, a system for treating a diabetic patient is illustrated, consistent with the present inventive concepts. System 10 comprises pump 100 and composition 200. Pump 100 can comprise reservoir 150, which can be used to surround, store, supply and/or otherwise provide (generally "provide" herein) composition 200, such as to allow prolonged and/or intermittent delivery of composition 200. Pump 100 can be configured to deliver composition 200 to one or more patient locations, such as when pump 100 delivers composition 200 into one or more of: subcutaneous tissue; a muscle; a vein; and/or an artery. Composition 200 can include two or more agents, such as when composition 200 comprises at least insulin (e.g. insulin and/or an insulin analogue, "insulin" herein) and glucagon (e.g. as a separate material or as a co-formulation or otherwise mixed state). Composition 200 can comprise a co-formulation or other mixture of at least two agents. Alternatively, composition 200 can comprise a first agent 201a (e.g. an agent including at least insulin) and a separate, second agent 201b (e.g. an agent including at least glucagon that is not mixed with the first agent). The ratio of the amount of first agent 201a and second agent 201b delivered to a patient by system 10 (e.g. an insulin/glucagon molar ratio, or I/G molar ratio) can be predetermined and/or otherwise controlled (e.g. controlled to a maximum, minimum, and/or within a range), such as to achieve a desired therapeutic benefit and/or lack of adverse events for the patient.

Pump 100 can comprise a pump positioned external to the patient, such as when pump 100 includes a fluid delivery element 130 comprising: an integrated needle (e.g. a needle positioned through the skin into a body location such as the subcutaneous (SQ) space, the intraperitoneal (IP) space, a vein, or an artery); an infusion set comprising a needle (e.g. a needle positioned through the skin into a body location such as the subcutaneous space, the intraperitoneal space, a vein, or an artery); and/or a catheter (e.g. a catheter positioned through the skin into a body location such as the subcutaneous space, the intraperitoneal space, a vein or an artery). Alternatively, pump 100 can comprise an implantable pump, such as when fluid delivery element 130 comprises a catheter, such as a catheter implanted in subcutaneous tissue. Pump 100 can comprise an implantable pump including a refill port accessible through the patient's skin via a needle.

Pump 100 can comprise one or more pumping mechanisms, such as a pumping mechanism 120 selected from the group consisting of: a syringe drive; a peristaltic pumping assembly; a rotary pump; a spring driven pump; and combinations of one or more of these. Reservoir 150 can comprise a single or multiple reservoirs, such as when reservoir 150 comprises one or more: syringes and/or chambers (e.g. compressible chambers).

In some embodiments, composition 200 comprises a co-formulation of insulin and glucagon, such as when reservoir 150 comprises a single reservoir that provides the co-formulation. Composition 200 can comprise a co-formulation of glucagon and a hepato-preferential insulin. A hepato-preferential insulin has enhanced liver-focused action, where glucagon is an effective competitor under hypoglycemic conditions. Use of a hepato-preferential insulin in a co-formulated composition 200 can be configured to provide enhanced results as compared to a co-formulation including non-hepatopreferential insulin, as the impact of non-hepatopreferential insulin in a co-formulated form on muscle glucose uptake will become more prominent.

In some embodiments, composition 200 comprises insulin and glucagon with an I/G molar ratio below about 6, such as an I/G ratio or below about 5, below about 4, or below about 3. In some embodiments, composition 200 comprises insulin and glucagon with an I/G molar ratio less than 6 but greater than about 1, such as an I/G molar ration above about 2 or above about 3. In some embodiments, composition 200 comprises insulin and glucagon with an approximate I/G molar ratio as used in applicant's studies described herebelow. In some embodiments, composition 200 may comprise insulin at a concentration between about 1 mg/ml and about 10 mg/ml, such as between about 3 mg/ml and about 5 mg/ml. In some embodiments, composition 200 may comprise glucagon at a concentration between about 0.1 mg/ml and about 1 mg/ml, such as between about 0.1 mg/ml and about 0.8 mg/ml. In some embodiments, composition 200 comprises insulin and glucagon at concentrations used in applicant's studies described herebelow. The composition 200 may be administered to a subject in an amount therapeutically effective to simultaneously treat or inhibit hyperglycemia and to inhibit hypoglycemia. For example, the composition may be administered in a manner that causes insulin to be administered at a basal insulin infusion rate between about 0.2-0.6 mU/kg/min, and that causes glucagon to be administered at a basal infusion rate between about 1-4 ng/kg/min. In some embodiments, the composition may be administered in a manner that causes insulin to be administered at a basal insulin infusion rate between about 0.3-0.5 mU/kg/min, and that causes glucagon to be administered at a basal infusion rate between about 2-3 ng/kg/min. Our data illustrate that an I/G molar ratio of 3 provides hypoglycemic protection with little to no negative consequences regarding treatment of hyperglycemia when the insulin infusion rate is increased to cover a meal. The optimal I/G molar ratio is likely to vary between 2 and 6, because lower I/G ratios may result in glucagon levels that could increase postprandial hyperglycemia while higher I/G molar ratios may provide too little hypoglycemic protection. In addition, since glucagon and insulin analogs can have differing potencies from native human insulin and glucagon the optimal ratios would have to be further adjusted to take into account the differing potencies when insulin and glucagon analogs are used.

Composition 200 further may comprise a solvent that includes one or more non-aqueous solvents and/or includes one or more aqueous solvents. In some embodiments, between about 20% and about 60% of the solvent (v/v) may consist of the one or more non-aqueous solvents. In some embodiments, at least one non-aqueous solvent may be an aprotic solvent, including, but not limited to, dimethyl sulfoxide (DMSO) or N-methylpyrrolidone (NMP). The solvent further may include one or more aqueous solvents. In some embodiments, no more than about 40% of the solvent (v/v) may consist of the one or more aqueous solvents. Finally, in some embodiments, between about 10% and about 40% of the solvent may be propylene glycol (PG), glycerol, or a combination of PG and glycerol.

Figure 1A:
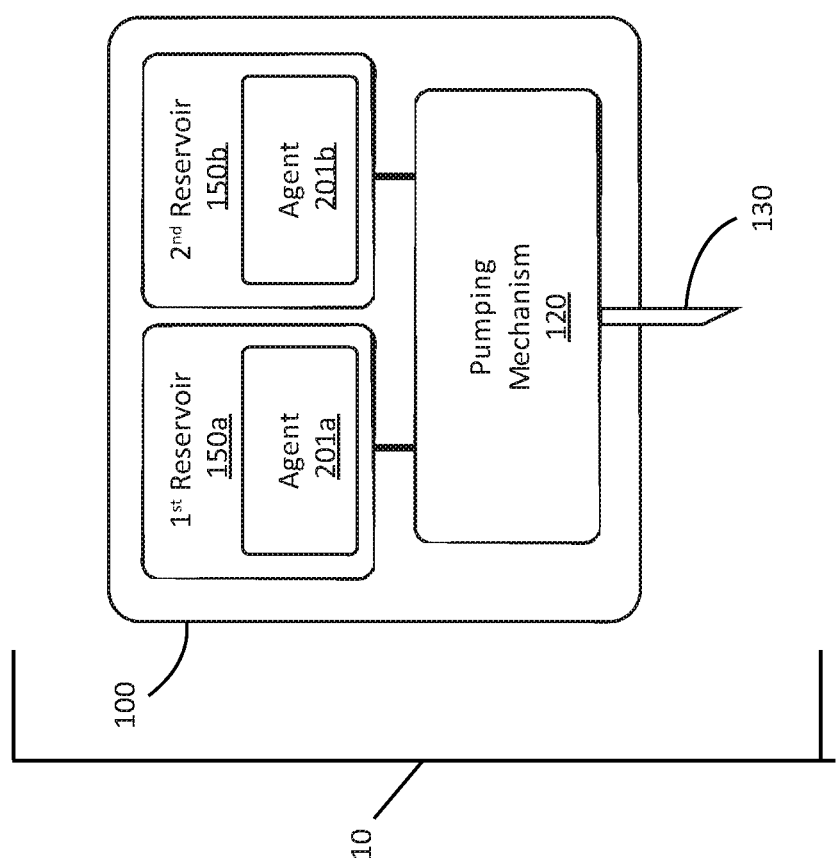
FIG. 1A illustrates a system for delivering a composition to a patient, comprising a single pumping device with two reservoirs, consistent with the present inventive concepts.

In some embodiments, pump 100 comprises a pump with dual reservoirs, such as is shown in FIG. 1A. Reservoir 150a can be configured to provide a first agent 201a (e.g. insulin) while reservoir 150b can be configured to provide a second agent 201b (e.g. glucagon). In these embodiments, composition 200 comprises agent 201a and separate (unmixed) agent 201b, collectively. Agents 201a and 201b can be mixed prior to entry into and delivery by a single pumping mechanism 120. The concentration of each of agents 201a and 201b stored in reservoirs 150a and 150b respectively, shall determine the ratio of the key components of each of the agents (e.g. to deliver a pre-determined molar ratio of insulin vs glucagon as described herein). Alternatively, pump 100 can comprise two pumping mechanisms 120 (e.g. mechanisms 120a and 120b not shown but independently controllable mechanisms), such that the flow rate of pumping can be configured (e.g. programmed or programmable) to achieve a desired ratio of delivery of agent 150a to agent 150b, independent of their relative concentrations.

Figure 1B:
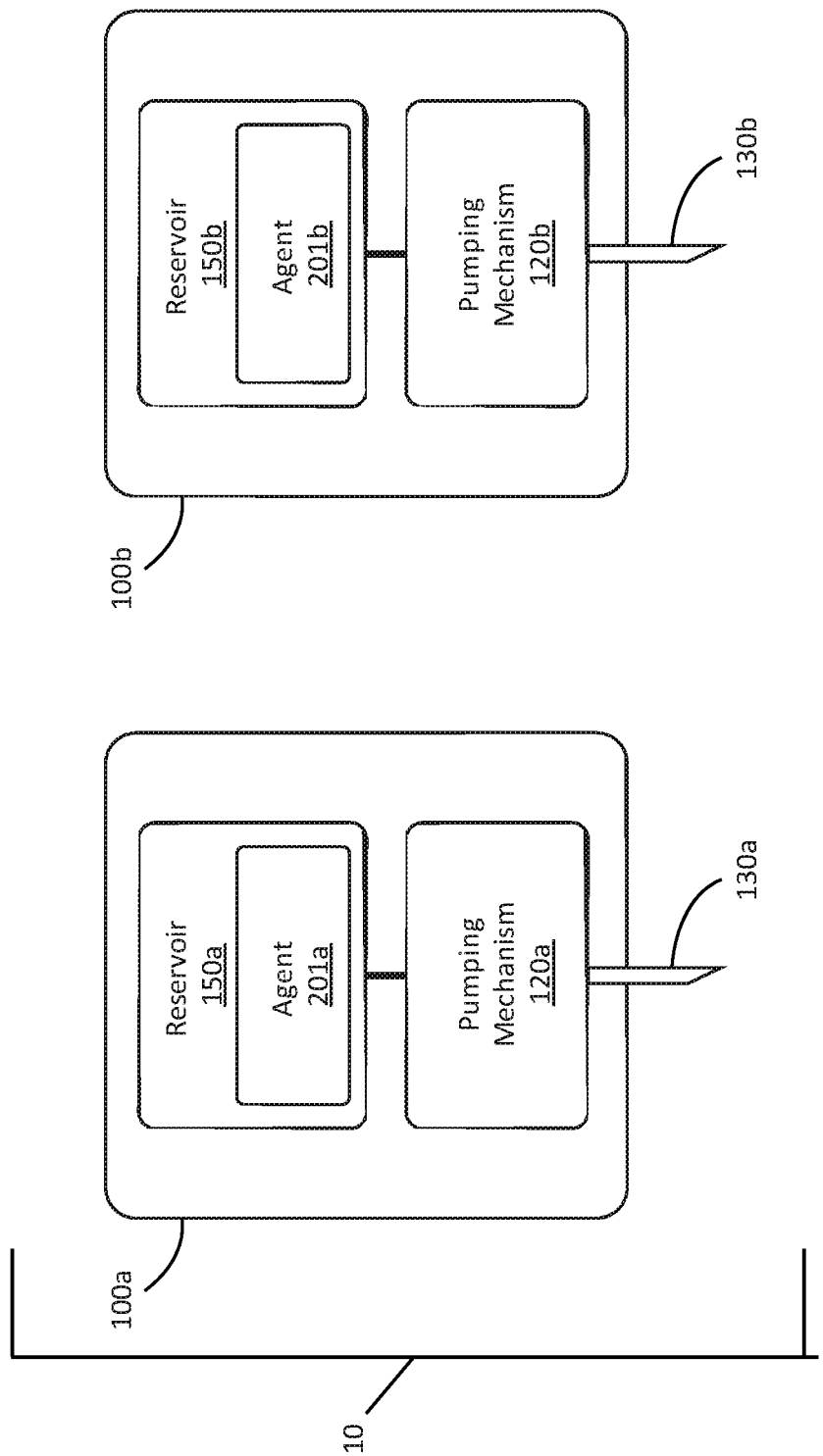
FIG. 1B illustrates a system for delivering a composition to a patient, comprising two pumping devices, consistent with the present inventive concepts.

In some embodiments, pump 100 comprises two pumps, pumps 100a and 100b, such as is shown in FIG. 1B. Pump 100a comprises reservoir 150a which can be configured to provide a first agent 201a (e.g. insulin). Pump 100b can comprise a second reservoir 150b which can be configured to provide a second agent 201b (e.g. glucagon). In these embodiments, composition 200 comprises agent 201a and separate (unmixed) agent 201b, collectively. The ratio of delivery of agent 201a to agent 201b is determined by both the concentration of each of the two agents 201a and 201b, as well as the programmed flow rates of each of the two pumps 100a and 100b (e.g. to deliver a pre-determined molar ratio of insulin vs glucagon as described herein).

Composition 200 may be configured such that its glucagon and insulin work in concert to closely regulate blood glucose. Insulin promotes the removal of glucose from blood to muscle and fat tissue and also inhibits the production of glucose by the liver, thereby lowering blood glucose levels. Glucagon stimulates hepatic glucose production, which is released into the bloodstream to elevate blood glucose. In people with diabetes, both the beta cell, which secretes insulin, and the alpha cell, which secretes glucagon, become defective. This issue manifests as insulin deficiency which leads to decreased glucose utilization and increased glucose production. At the same time, glucagon excess also results in increased glucose production. It is not surprising, therefore, that current therapeutic approaches have focused on enhancing insulin secretion and action, and blocking glucagon secretion and action.

One of the major barriers to the effective treatment of people with diabetes is their defective ability to respond to hypoglycemia with a normal glucagon response, particularly in people with Type 1 diabetes (T1D). This deficiency makes patients with T1D more susceptible to hypoglycemia than the normal (non-diabetic) individual. As a result of this defect, the blood glucose level in these patients oscillates wildly, exhibiting both marked hyperglycemia and hypoglycemia, thereby making it very difficult for such patients to adequately control their blood glucose level with insulin treatment alone. Recently, investigators, using closed loop insulin pumps, have come to the conclusion that using insulin at times of high blood glucose and glucagon at times of low blood glucose can reduce the magnitude of both hypoglycemia and hyperglycemia (e.g. as described in publications by Russel, et al in New England Journal of Medicine, June 2014 and Bakhtiani, et al, in Diabetes, Obesity and Metabolism, 2013). Notwithstanding the use of real-time glucose sensors and sophisticated algorithms to trigger either insulin or glucagon infusion in closed loop systems, there is still a significant unmet need to reduce such oscillations in blood glucose and to minimize hypoglycemic episodes.

Composition 200 comprises a particular relationship (e.g. ratio) between the quantities of insulin and glucagon to achieve a beneficial therapeutic effect while minimizing hypoglycemia. Composition 200 may comprise such a ratio and/or otherwise be configured to avoid complications from hyperinsulinemia and/or hyperglucagonemia. In some embodiments, system 10 and composition 200 are configured to provide sufficient glucagon to the patient to be able to protect against hypoglycemia risk in the context of hyperinsulinemia or increased insulin delivery. System 10 can provide glucagon to the patient at a rate of approximately 2 ng/kg/min. System 10 can provide glucagon at a rate of more than 0.5 ng/kg/min, or more than 0.75 ng/kg/min, such as to protect against hypoglycemia when insulin levels are elevated or infusion rate is increased. Alternatively or additionally, system 10 can provide a glucagon infusion rate less than 20 ng/kg/min, so as to avoid increasing the risk of metabolic derangement and/or cardiovascular toxicity from excess glucagon. In some embodiments, system 10 and composition 200 provide an infusion rate of insulin configured to maintain glucose homeostasis in the face of the previously defined levels of glucagon infusion. Composition 200 can comprise a ratio between 1:1 and 6:1 of human insulin:human glucagon, such as a ratio of between about 1:1 and 5:1, between about 3:1 and about 6:1, or between about 3:1 and about 5:1, such as to both lower glucose effectiveness as well as reduce risk of hypoglycemia. In some embodiments, system 10 may be configured to administer less than 3.2 mU/kg/min of insulin (e.g. human insulin), so as to reduce the potential for administration of excess insulin that cannot be overcome by any amount of glucagon.

In some embodiments, system 10 provides glucagon at a minimum rate that is configured to be sufficient for protection from hypoglycemia under conditions of hyperinsulinemia without causing toxicity from hyperglucagonemia, such as a rate above 10 ng/kg/min or a rate above 20 ng/kg/min that could be delivered subcutaneously. In some embodiments, composition 200 comprises insulin:glucagon at a ratio configured to allow improved glucose homeostasis in the context of the glucagon delivered by system 10 via composition 200. By administering a composition 200 comprising a fixed molar ratio, system 10 provides protection from hypoglycemia even if insulin will be bolused by system 10 (e.g. via pump 100).

Applicant has conducted studies, which have shown that the way in which glucagon and insulin interact to control liver glucose production is influenced by the prevailing plasma glucose level. For instance, raising both the insulin and glucagon levels 4-fold on a molar basis under euglycemic conditions results in insulin action dominating glucagon action. In fact, the ability of a 4-fold rise in glucagon to stimulate hepatic glucose production is reduced by 80% when the insulin level also rises 4-fold. The reverse occurs under hypoglycemic conditions. Applicant has shown that under hypoglycemic conditions, glucagon becomes 3 times more effective in the presence of low glucose than under euglycemic conditions, even in the presence of high insulin levels. It has been demonstrated that hypoglycemia disengages insulin signaling in the liver thus allowing glucagon to work better. This improved glucagon effectiveness leads to the paradoxical possibility that co-administration of insulin and glucagon provides a therapeutic advantage.

The present inventive concepts described herein teach that co-administration or co-formulation of insulin and glucagon in the correct proportion allows more aggressive and yet safe treatment of T1D patients, providing enhanced long-term control of blood sugar levels. During eating and elevated blood glucose, the systems, compositions and methods of the present inventive concepts provide a prandial dose of insulin and glucagon in which the two are increased proportionately, where the impact of the extra insulin overrides the impact of the extra glucagon. During periods of low blood sugar, on the other hand, elevated insulin would be less effective at the liver, allowing the extra glucagon to drive increased glucose production thereby limiting hypoglycemia and reducing the need for sympathetic nervous system activation. The present inventive concepts provide co-administration and/or co-formulation of glucagon and insulin that limits these glycemic excursions, thereby improving HbA1c levels and reducing diabetic complications of the patient.

The present disclosure provides: using co-infusions of defined ratios of insulin and glucagon for control of blood glucose; using a co-formulated insulin glucagon mixture for control of blood glucose; use of an insulin and glucagon mixture to reduce hypoglycemia associated autonomic failure (HAAF); use of an insulin glucagon mixture to prevent insulin-mediated weight gain; use of an insulin glucagon mixture to limit fat accumulation in the liver. The present inventive concepts safely reduce glycemic variability in T1D patients, thereby allowing more aggressive treatment which leads to improved HbA1c levels and reduced complications to the patient. As described herein, insulin of the present inventive concepts can include insulin, analogues of insulin, and a preferentially biased insulin, such as hepato-preferential insulin.

Normally, insulin and glucagon are secreted into the hepatic portal vein such that the liver is exposed to a level 2 to 3-fold greater than any other tissues. After an overnight fast, the basal I/G molar secretion ratio is approximately 10, but it can vary from a low level (e.g. approximately 0) to a high level (e.g. approximately 240) in a state of hypoglycemia or hyperglycemia respectively. In applicant's preliminary experiments, it was shown that when the two hormones are infused peripherally, a molar ratio of approximately 3-4 is required to maintain normal fasting glucose metabolism when the glucagon infusion rate was 1.6 ng/kg/min. Studies included examining the ability of a rise in insulin to cause hypoglycemia or prevent hyperglycemia, by delivering composition 200 with an I/G ratio of approximately 20 and approximately 4.

Figure 2:
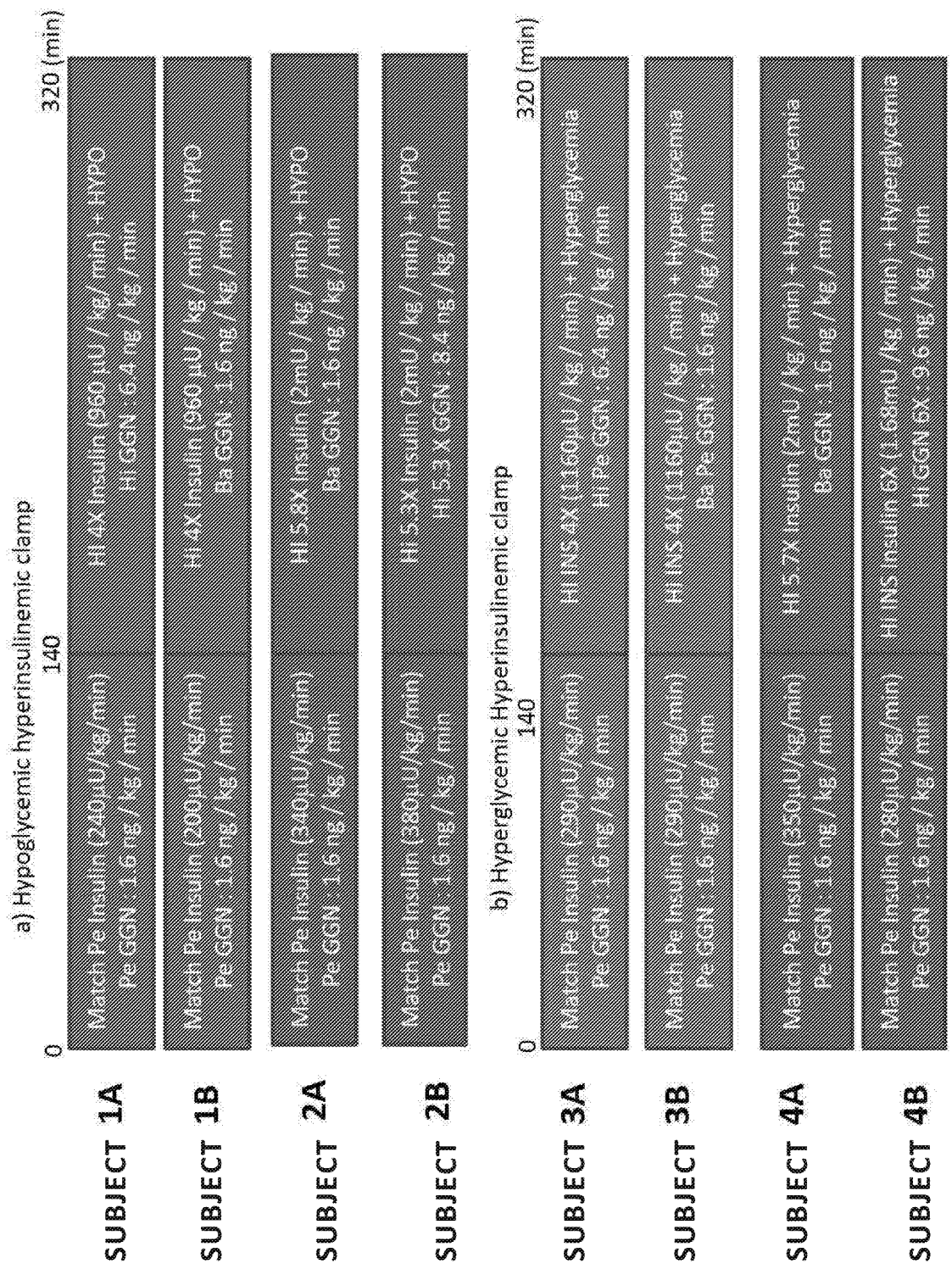
FIGS. 2-15 illustrate data from mammalian studies conducted by applicant, consistent with the present inventive concepts.

Applicant has conducted paired studies (experiments A and B) on each of four conscious subjects (canine), denoted subjects 1, 2, 3 and 4, in support of the clinical value of co-administration of elevated insulin and glucagon. Results of these studies are shown in FIGS. 2-15. In subjects 1 and 2, control was taken of the endocrine pancreas at 0 min by delivering somatostatin to inhibit endogenous insulin and glucagon secretion, and replacing both hormones by infusion through a leg vein. Glucagon was infused at 1.6 ng/kg/min (about 3 times its normal secretion rate), and insulin was infused as required to maintain euglycemia. In subject 1, 200-240 µU/kg/min was required, while in subject 2 340-380 µU/kg/min was required. In the test period (140-320 min) of Experiment A (see FIG. 2) on subject 1, plasma insulin and glucagon were raised 4-fold, while in Experiment B on the same subject, insulin was raised 4.8-fold and glucagon was kept at 1.6 ng/kg/min. In subject 2, both insulin and glucagon were increased 5.3-fold in experiment B, whereas in experiment A insulin was increased 5.8-fold while glucagon was kept basal (unchanged). In this way, the protective effect of the increase in glucagon (4-fold basal in subject 1 and 5.3-fold basal in subject 2) on insulin driven hypoglycemia was assessed.

Figure 3:
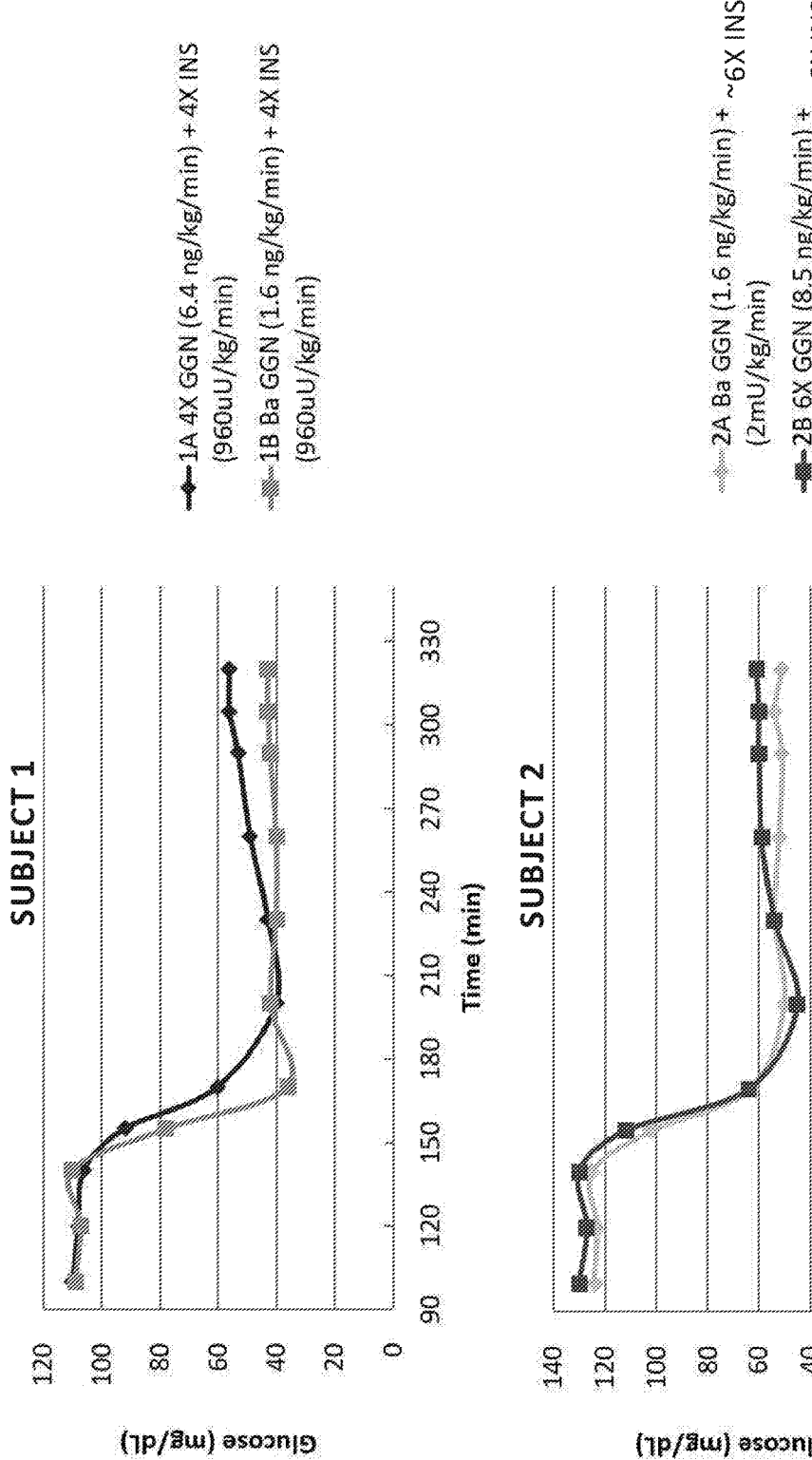

FIG. 3 illustrates data that show the plasma glucose excursions evident in the test period of the above experiments. The extra glucagon tended to slow the fall in plasma glucose in one subject, but most importantly it caused plasma glucose to rebound to almost 60 mg/dl in both subjects (reference experiments 1A, 2B shown in FIG. 3). The same rise in insulin, when brought about in the presence of basal glucagon, caused sustained hypoglycemia of approximately 40 mg/dl and approximately 50 mg/dl, in experiments 1B and 2A respectively.

Figure 4:
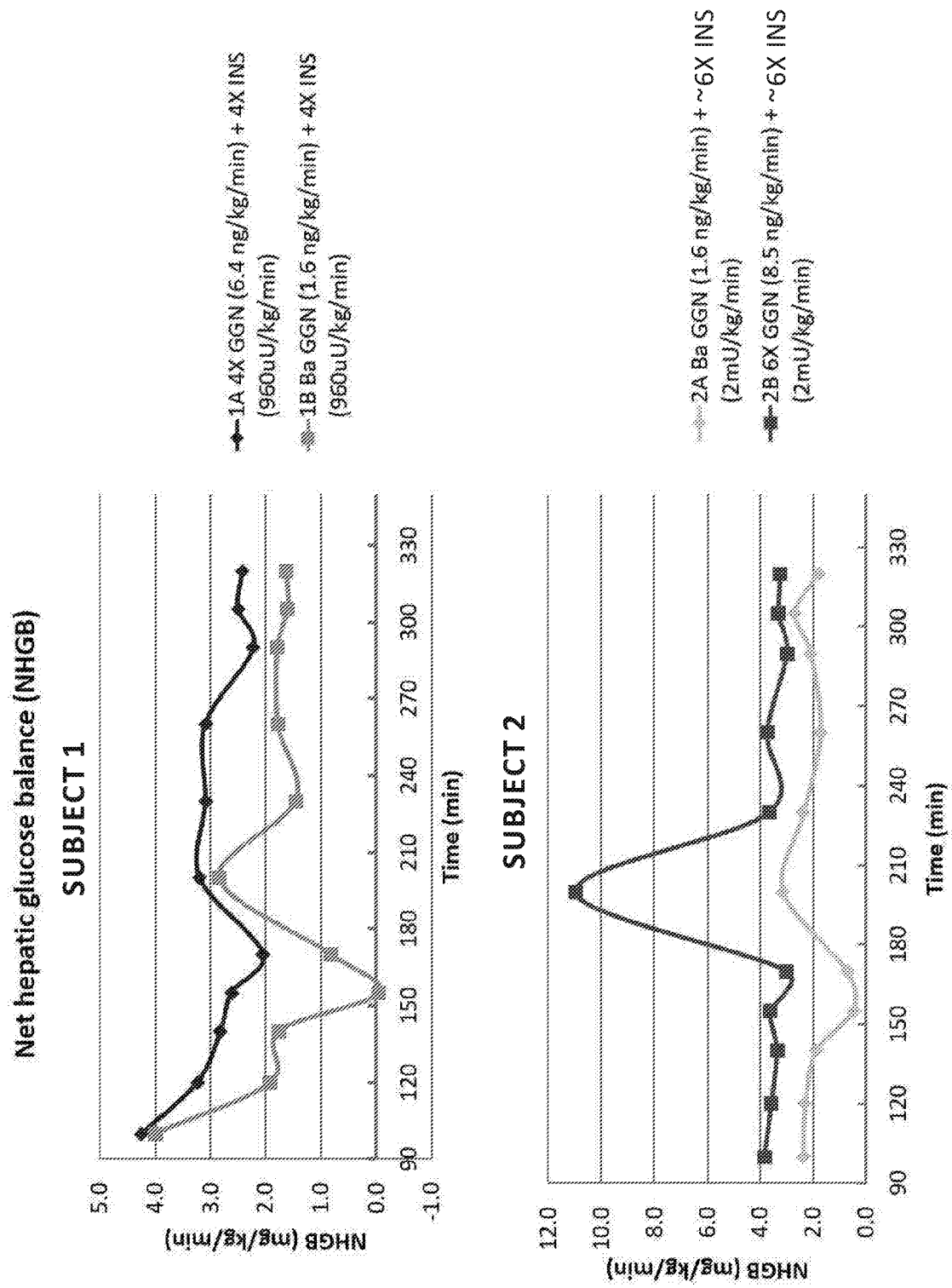

FIG. 4 illustrates data that show that insulin's inhibitory effect on net hepatic glucose output (NHGO) was clearly blunted by the presence of extra glucagon (as shown in 1A and 2B).

Figure 5:
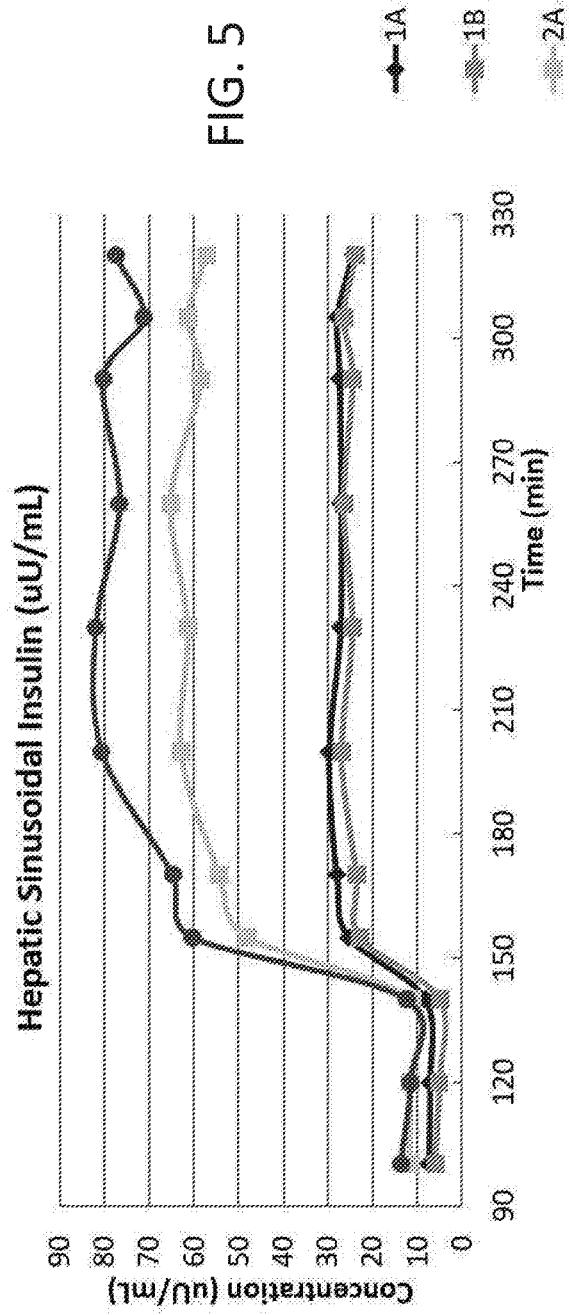

FIG. 5 illustrates data that show that the plasma insulin level within the liver was similar in both experiments in subject 1, and that in subject 2 plasma insulin was slightly higher in Experiment B than A. This result with subject 2 indicates the data shown in FIG. 3 is even more remarkable, because the extent of hypoglycemia in experiment B on subject 2 was reduced even though the plasma insulin level was somewhat higher in that subject.

Figure 6:
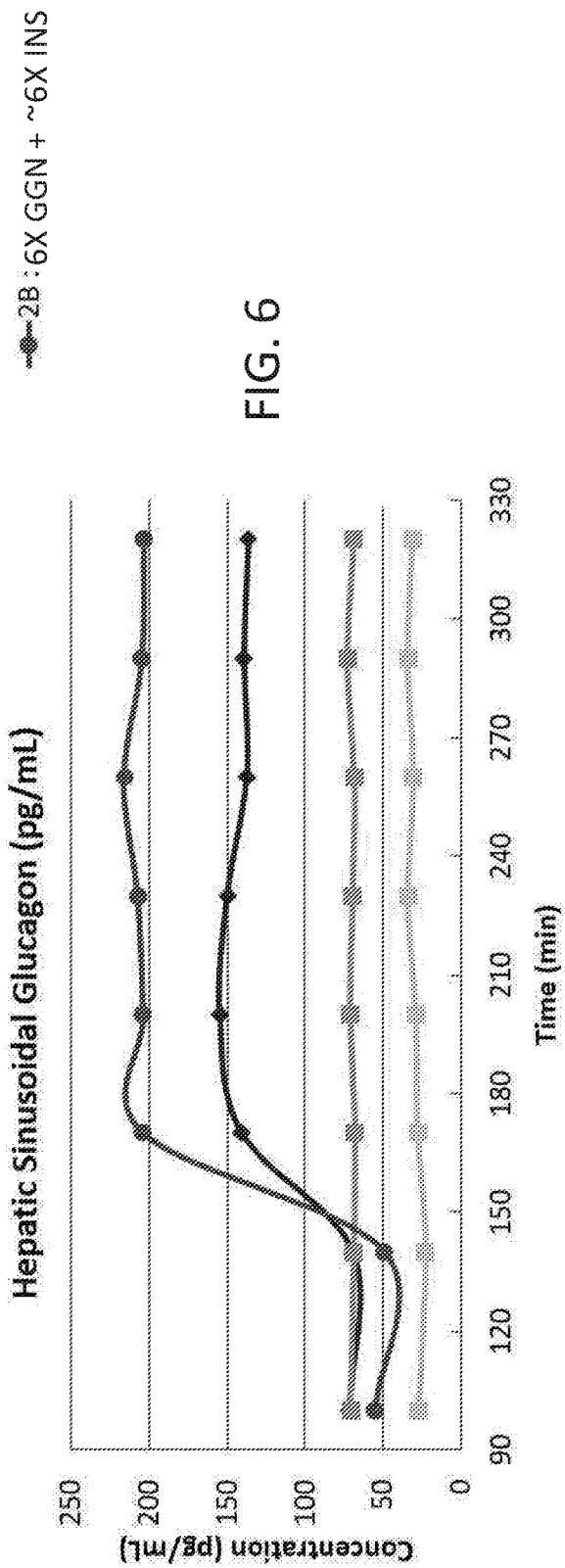

FIG. 6 illustrates data that confirms that plasma glucagon remained basal in experiments 1B and 2A, but rose in experiments 1A and 2B (due to the 4-fold and 5.3-fold increases in glucagon infusion respectively).

Figure 7:
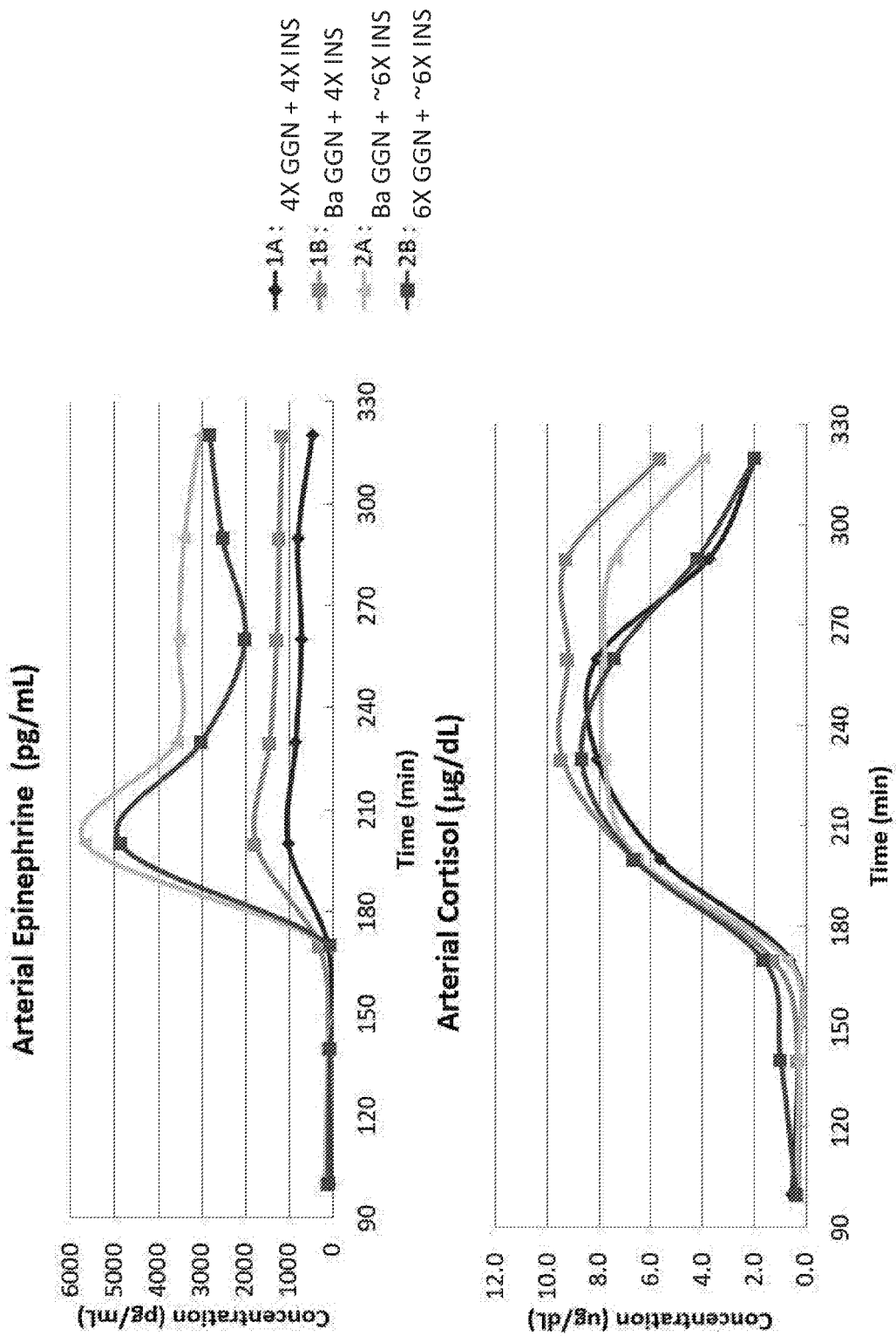
Figure 8:
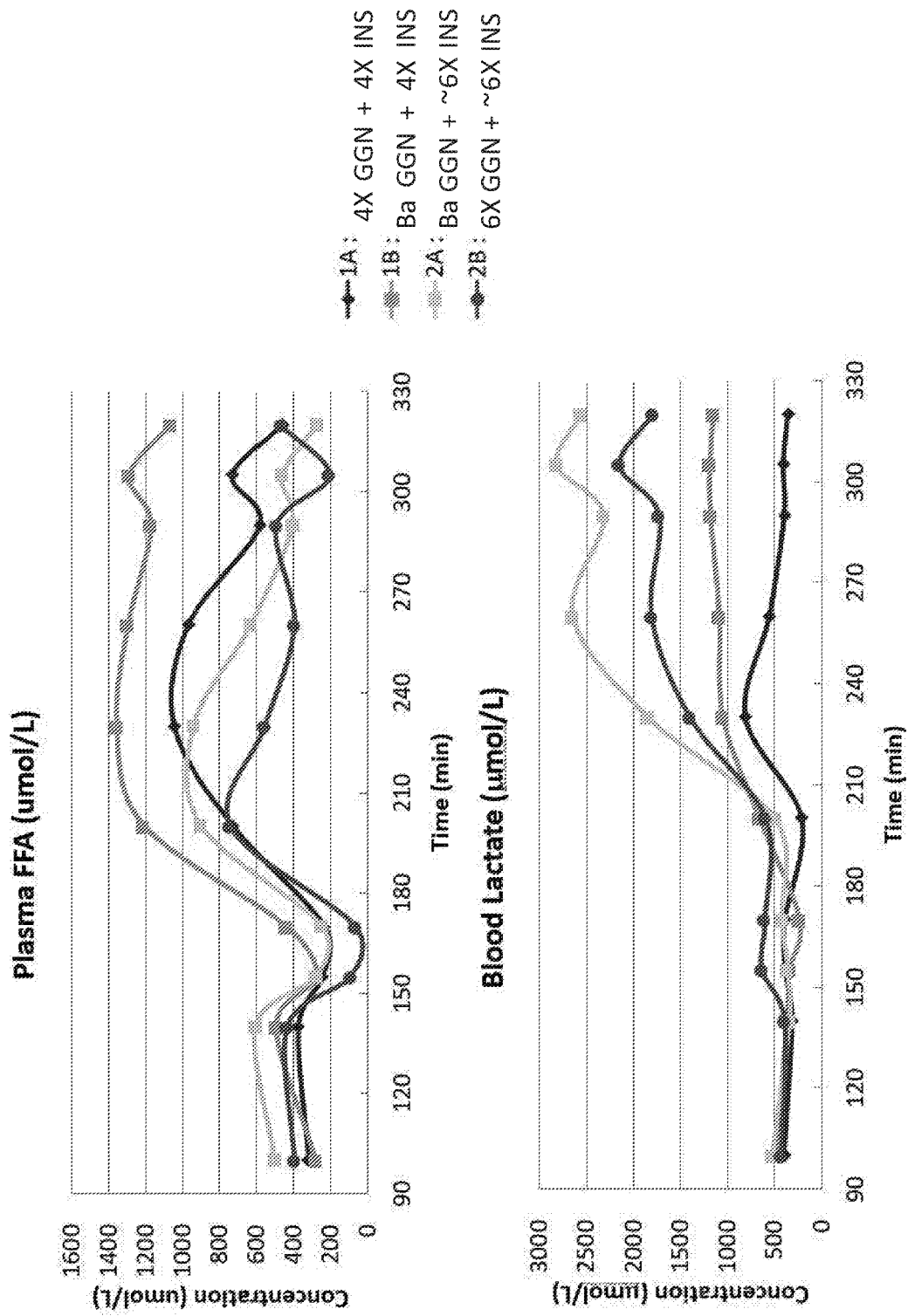
Figure 9:
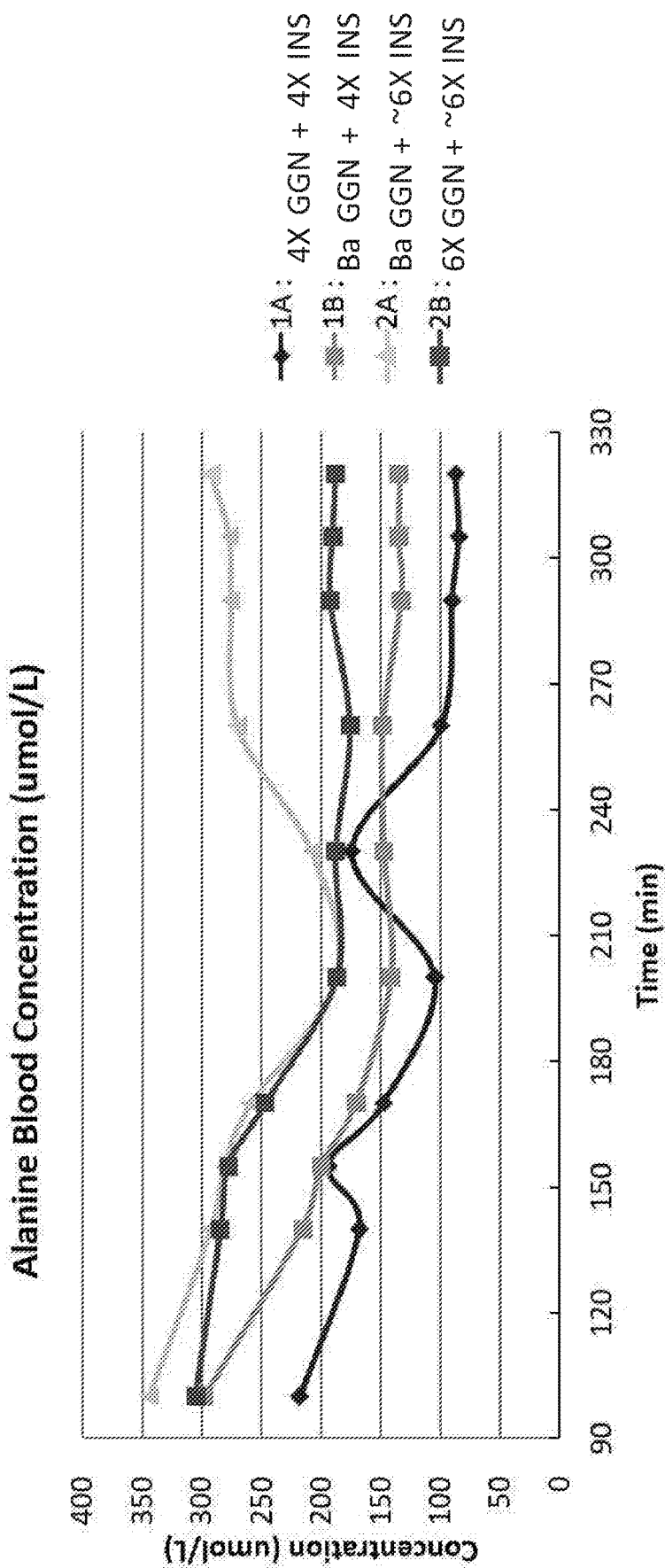

FIG. 7 illustrates data that shows that the plasma cortisol level fell in experiments 1A and 2B, as the glucose returned to 60 mg/dl. The data also shows that the arterial plasma epinephrine excursion was reduced when glucagon was elevated (1A, 2B), indicating a reduced, sympathetic nervous system response to hypoglycemia. Consequently, the lipolytic response was also reduced as evidenced by a much smaller rise in plasma FFA in experiment 1A and 2B (as shown in FIG. 8). Similarly, the sympathetic drive to muscle was abrogated in the presence of increased glucagon (1A, 2B), resulting in much smaller increases in blood lactate levels. As expected, the increases in insulin ±glucagon caused the blood alanine level to fall (as shown in FIG. 9).

Clearly, when glucagon and insulin rose proportionately (as opposed to insulin increasing in isolation), the presence of extra glucagon blunted the hypoglycemic response attributable to insulin, and reduced the activation of the nervous system which would otherwise have been required to protect the blood sugar level. Thus, the amelioration of hypoglycemia occurred despite reduced CNS activation. These data therefore suggest the present inventive concepts can be used to reduce hypoglycemia associated autonomic failure (HAAF).

In some embodiments, the co-formulation of insulin and glucagon of the present inventive concepts not only limits hypoglycemia, but it also does not significantly impair post-prandial glucose uptake by the liver. This dual benefit was demonstrated in two subjects (subjects 3 & 4). As in subjects 1 and 2, a pancreatic clamp was brought about by delivering somatostatin to inhibit insulin and glucagon secretion, and replacing both glucagon at 1.6 ng/kg/min and insulin (290 µU/kg/min in subject 3 and 280-350 µU/kg/min in subject 4) into a leg vein, as required to maintain euglycemia (see FIG. 2). At 140 min, the insulin infusion rate was increased 4 or 6-fold while glucagon was either left unchanged (3B, 4A) or increased 4 or 6-fold (3A, 4B). At the same time, glucose was infused through a leg vein to double the blood sugar level (approximately 200 mg/dl).

Figure 10:
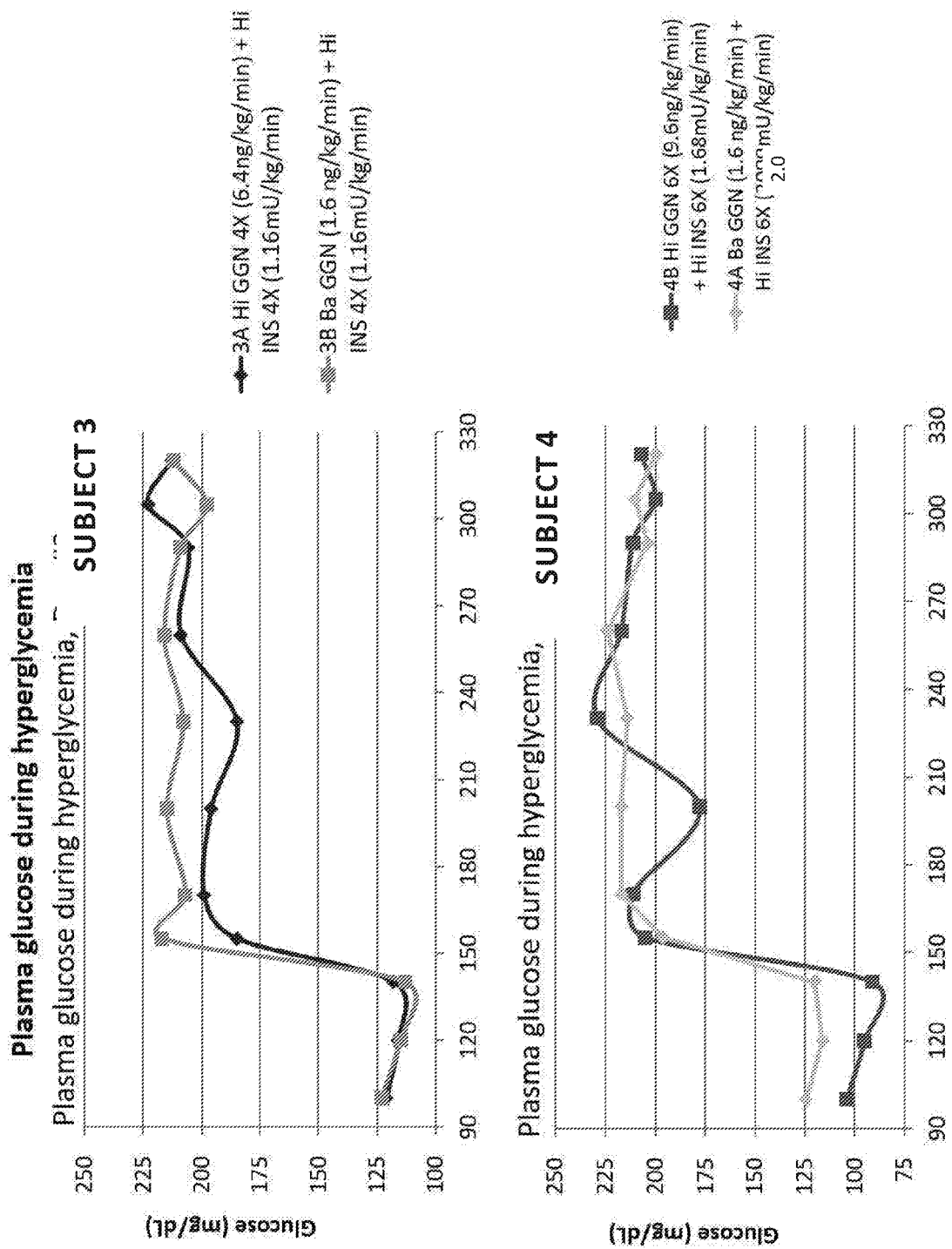
Figure 11:
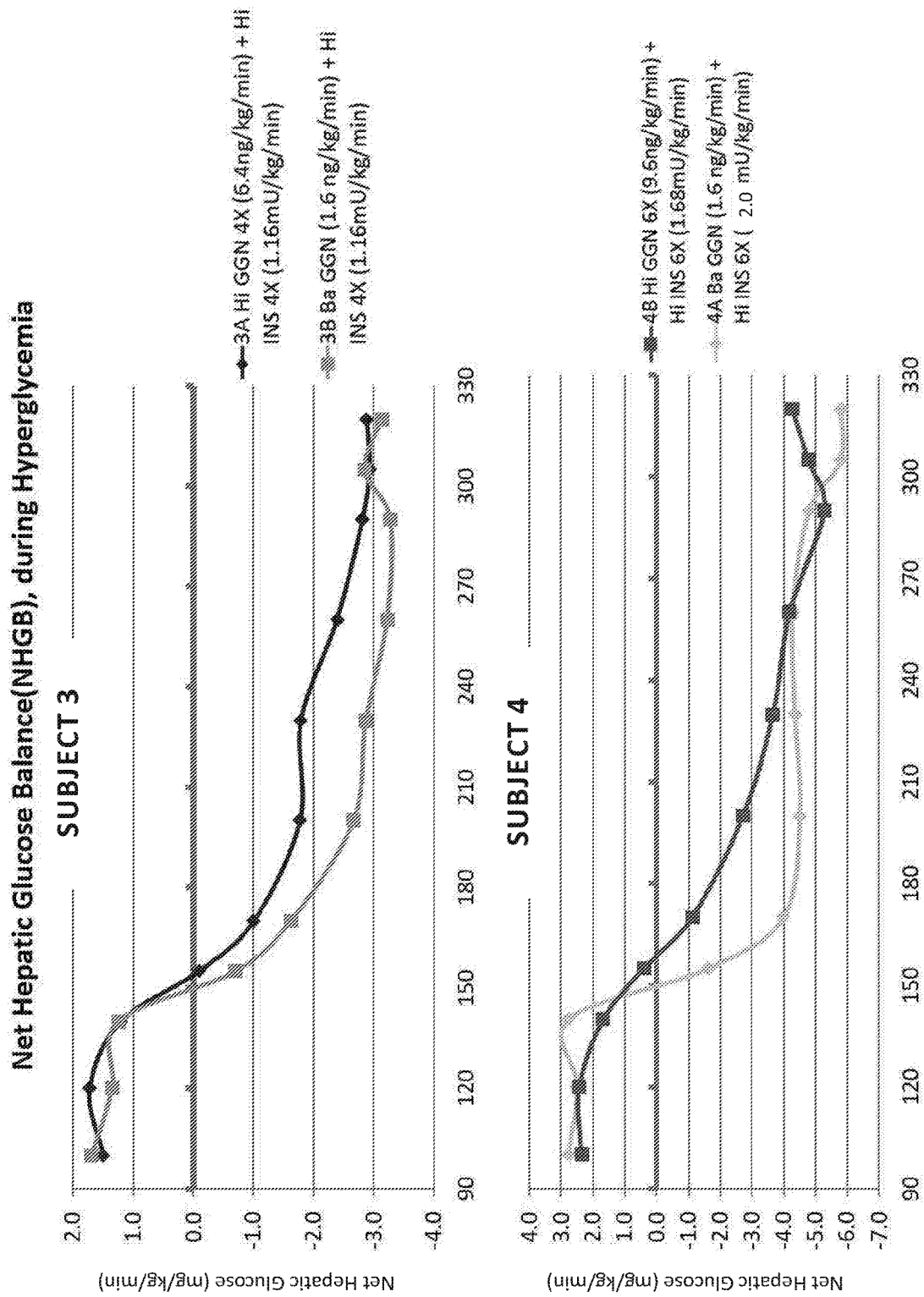

FIG. 10 illustrates data that shows that the plasma glucose level rose to >200 mg/dl in all four experiments. FIG. 11 illustrates data that show that the liver switched from net hepatic glucose output to net hepatic glucose uptake (NHGU) in response to the combined stimulus of hyperinsulinemia and hyperglycemia. The extra glucagon initially slowed the increase in NHGU somewhat, but by the last hour of the experiment NHGU was not appreciably different (2.8 vs 3.1 mg/kg/min in subject 3; 4.8 vs 5.1 mg/kg/min in subject 4 in the presence or absence of the extra glucagon respectively).

Figure 12:
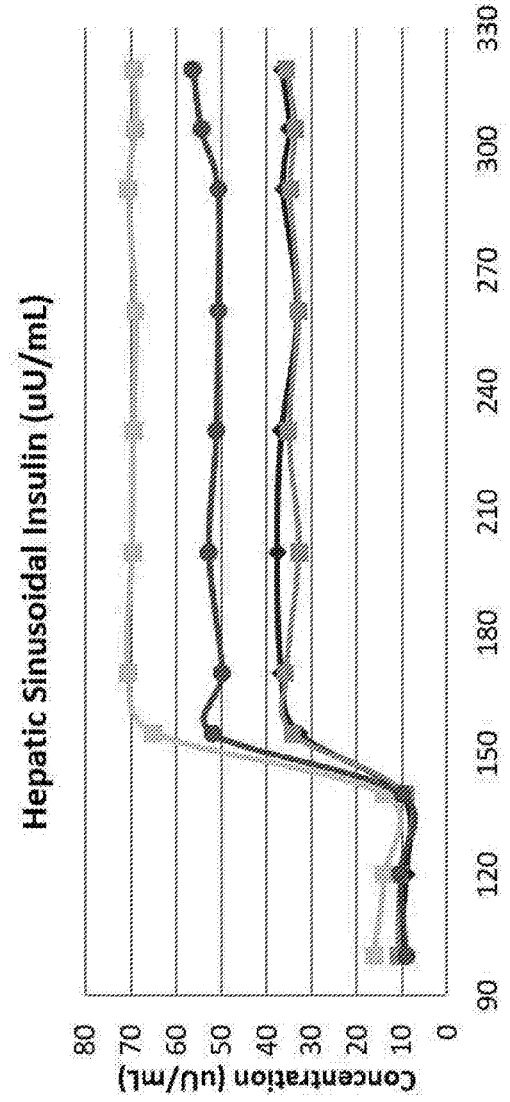

FIG. 12 illustrates data that show that the increments in plasma insulin were equal in the two experiments in subject 3 and that insulin was modestly higher in the presence of basal glucagon in subject 4, making the glucose balance data even more impressive since extra insulin should have further increased NHGU.

Figure 13:
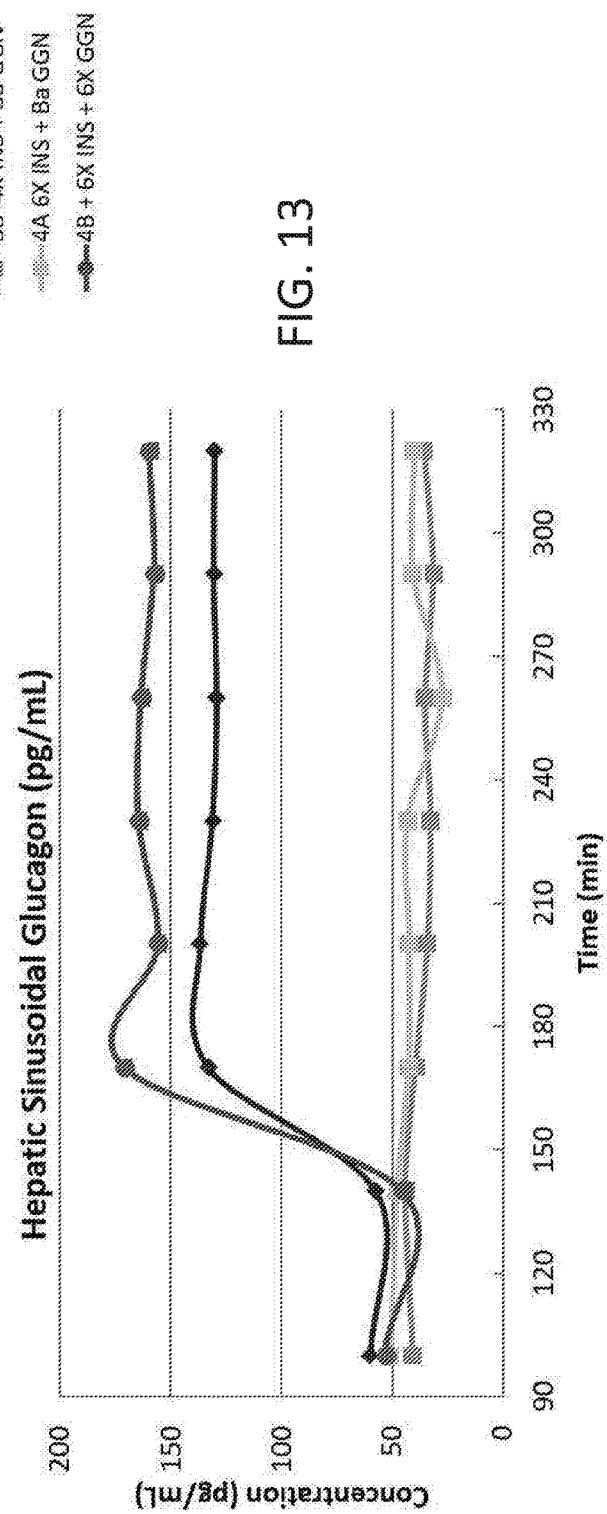

FIG. 13 illustrates data that show that plasma glucagon was indeed elevated in experiments 3A and 4B but not in 3B and 4A.

Figure 14:
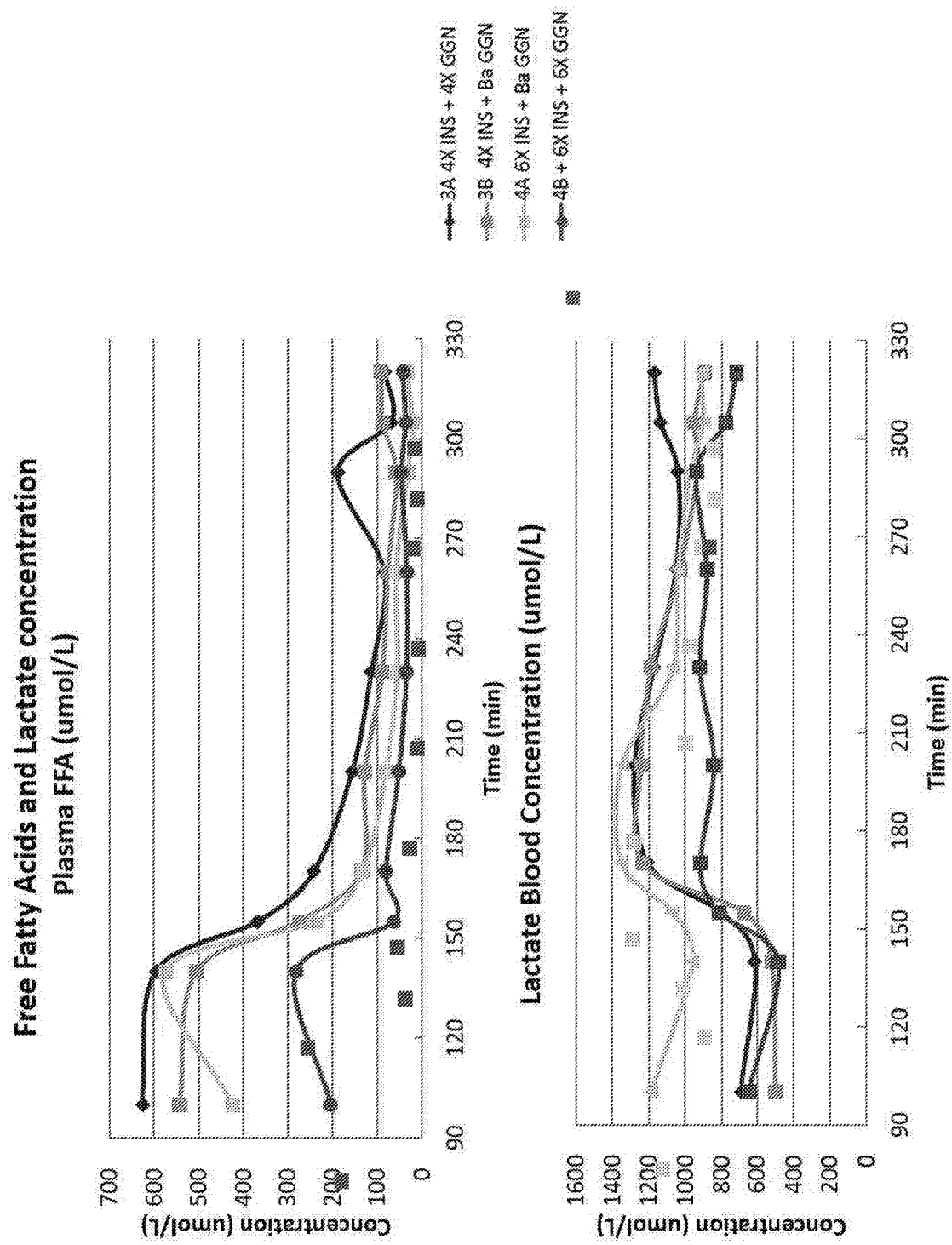
Figure 15:
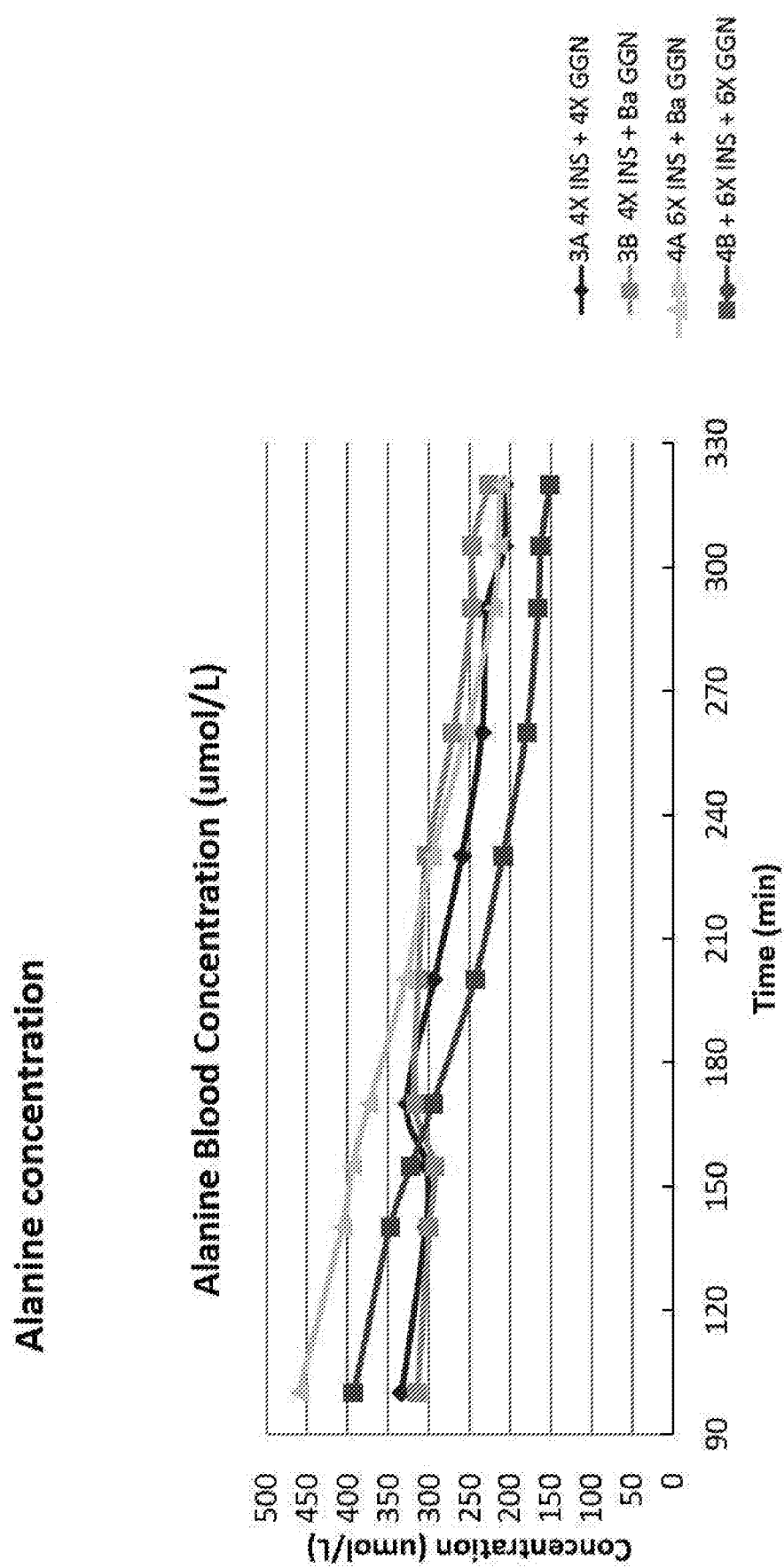

FIG. 14 illustrates data that show that the suppression of lipolysis was equivalent in the four experiments as indicated by indistinguishable changes in plasma FFA and glycerol (glycerol data not shown). Likewise, neither the rise in plasma lactate nor the change in the blood alanine level was different in the four experiments (as shown in FIGS. 14 and 15).

Thus, the presence of extra glucagon had little or no impact on the ability of the liver to take up and store glucose under hyperinsulinemic/hyperglycemic conditions. These data thus show that elevating glucagon in the presence of elevated insulin limits insulin induced hypoglycemia without appreciably blunting insulin's ability to inhibit lipolysis or cause net hepatic glucose uptake under hyperglycemic conditions.

Normally insulin and glucagon are secreted into the hepatic portal vein such that the liver is exposed to a level 2 to 3-fold greater than any other tissues. After an overnight fast, the basal I-G molar secretion ratio is approximately 10, but it can vary widely depending on the presence of hypoglycemia or hyperglycemia, as well as other factors. In preliminary experiments, the peripheral vein glucagon infusion rate was set to 1.6 ng/kg/min (0.45 pmol/kg/min; 3-fold its basal secretion rate into the portal vein). It was then established that it required a peripheral infusion rate of insulin (of 1.62 pmol/kg/min; I/G molar ratio of approximately 3.7) to maintain normal fasting glucose metabolism. With this in mind, experiments examined the ability of an increase in insulin infusion to cause hypoglycemia when glucagon was increased proportionally to insulin (an I/G molar ratio of 3-5) or when it was kept at 1.6 ng/kg/min (an I/G molar ratio of 12-25).

Figure 16:
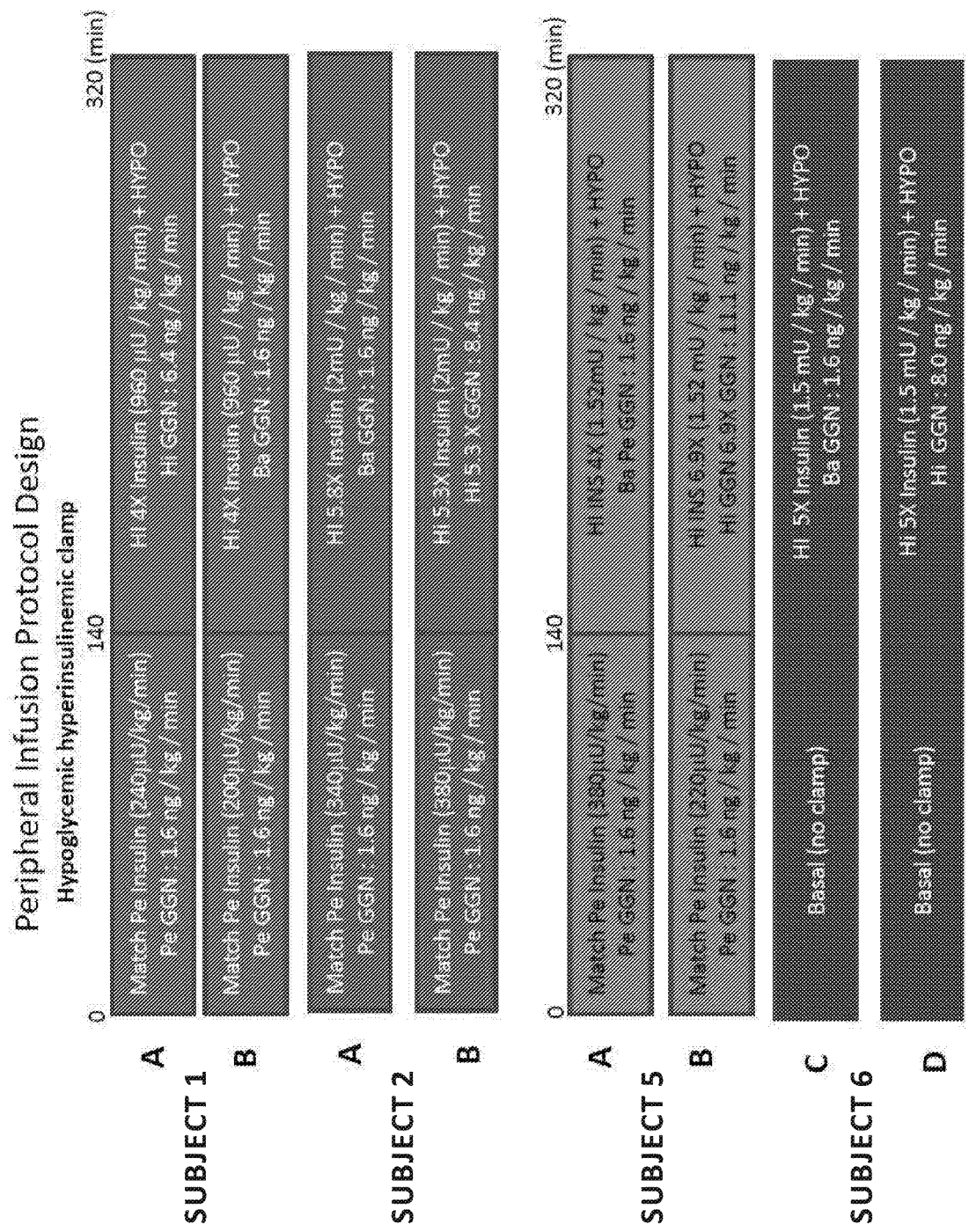
FIG. 16 illustrates a protocol of a mammalian study conducted by applicant, consistent with the present inventive concepts.

Paired studies were conducted on four conscious subjects (canine) to test the hypothesis that simultaneously elevating insulin and glucagon (e.g. maintaining the I/G molar ratio at a basal value) rather than raising insulin alone and thus increasing the I/G molar ratio, would limit insulin induced hypoglycemia. In subjects 1, 2 and 5, control of the endocrine pancreas at 0 min was established by delivering somatostatin to inhibit endogenous insulin and glucagon secretion, and both hormones were replaced by infusing the hormones through a leg vein of each subject. The experiments included infusing glucagon at 1.6 ng/kg/min (about 3 times its normal secretion rate), and insulin was infused as required to maintain euglycemia. In subject 1, 200-240 µU/kg/min was required; in subject 2, 340-380 µU/kg/min was required; and in subject 5, 220-380 µU//kg/min was required. In the test period (140-320 min) of Experiment A (FIG. 16) in subject 1, plasma insulin was raised 4-fold and glucagon was raised 4-fold, while in Experiment B insulin was raised 4.8-fold and glucagon was kept unchanged (at 1.6 ng/kg/min). In subject 2, both insulin and glucagon were increased 5.3-fold in experiment B, whereas in experiment A insulin was increased 5.8-fold and glucagon was kept basal. In subject 5, insulin was increased 4-fold in experiment A and 6.9-fold in experiment B while glucagon was kept at 1.6 ng/kg/min in experiment A and it was increased 6.9-fold in experiment B. In this way, assessment was performed on the protective effect of the increase in glucagon on insulin driven hypoglycemia. In subject 6, there was no basal clamp period but during the test period (140-320 min) insulin infusion was increased 5-fold and glucagon infusion was either kept at 1.6 ng/kg/min or increased 5-fold.

FIGS. 17-24 depict the data from the eight experiments described above. FIGS. 17, 19, 21, and 23 illustrate the glucose data from the control period (hatched bars), and the last 2 hours of the experimental periods (open bars). In the control period, plasma glucose, net hepatic glucose output, insulin and glucagon were equal in the two experiments on each subject. In the experimental period of subject 1 (FIG. 17) the insulin level was equivalent in both experiments but in one case glucagon was kept basal (I/G molar ratio of 12) while in the other it increased markedly sustaining an I/G molar ratio of 3. Raising glucagon proportionally to insulin, stimulated net hepatic glucose output and this reduced the fall in the plasma glucose level substantially (approximately 8 mg/dl).

Figure 17:
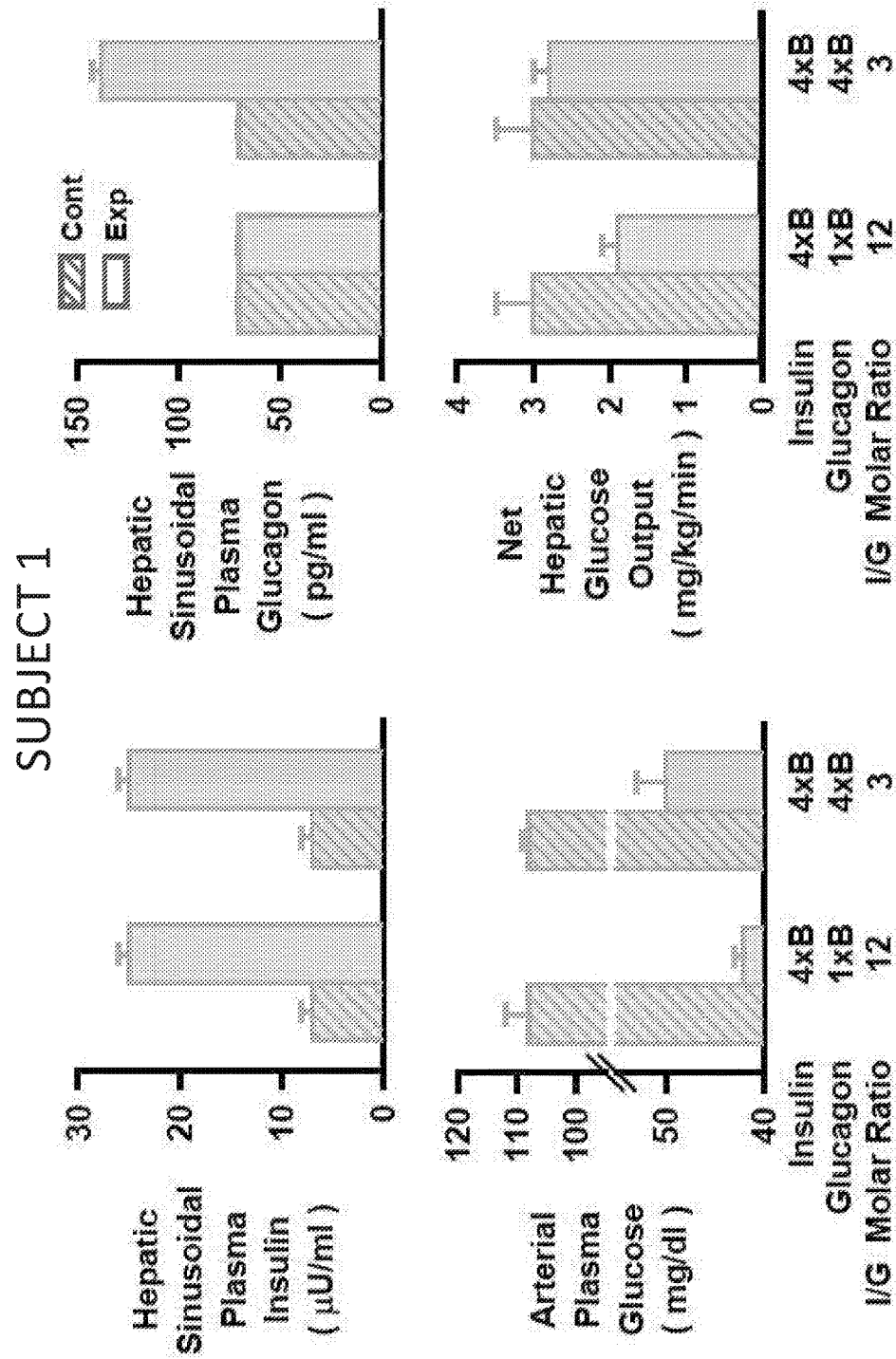

Referring to FIG. 17, data from subject 1 is illustrated. Somatostatin was infused to disable the endocrine pancreas during the experimental period. Insulin was infused in a leg vein of subject 1 for 3 hours at a rate 4× its basal (B) secretion rate along with an infusion of glucagon at a basal rate (I/G Ratio of 12) or a rate 4×B (I/G Ratio of 3). The insulin—induced fall in glucose was reduced by the extra glucagon (a nadir of 42±1 vs 50±3 mg/dl) as a result of increased glucagon-driven hepatic glucose production (2.8±0.2 vs 1.9±0.2 mg/kg/min). The data are from the control period (hatched bars) and the last 2 hours of the experimental period (solid bars).

Figure 19:
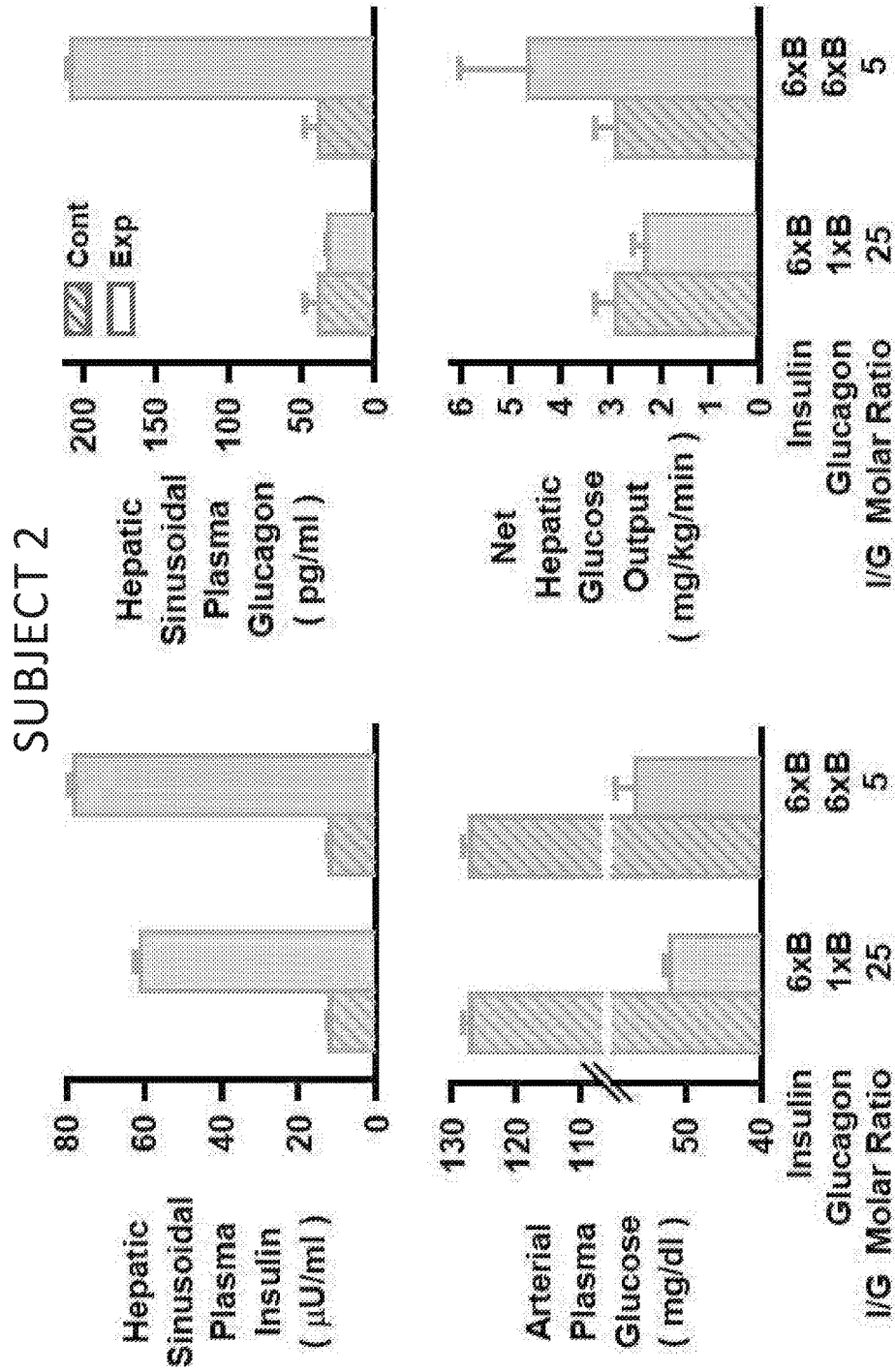

Referring to FIG. 19, data from subject 2 is illustrated. Somatostatin was infused to disable the endocrine pancreas during the experimental period. Insulin was infused in a leg vein of subject 2 for 3 hours at a rate 6× its basal (B) secretion rate along with an infusion of glucagon at a basal rate (I/G ratio of 25) or a rate 6×B (I/G ratio of 5). The insulin-induced fall in glucose was reduced by the extra glucagon (a nadir of 52±1 vs 57±3 mg/dl) as a result of increased glucagon-driven hepatic glucose production (2.3±0.2 vs 4.6±1.4 mg/kg/min). The data are from the control period (hatched bars) and the last 2 hours of the experimental period (solid bars).

Figure 21:
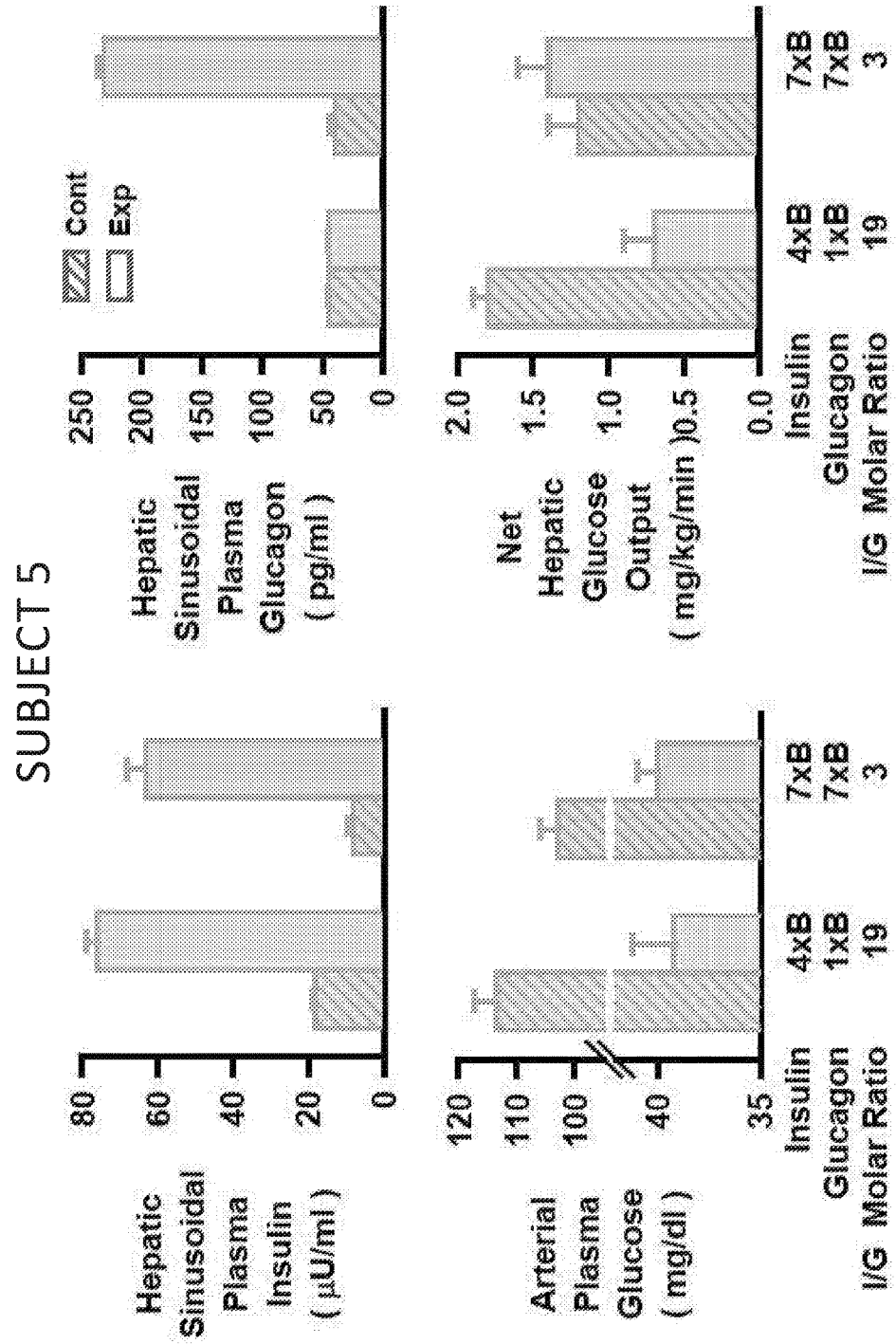

Referring to FIG. 21, data from subject 5 is illustrated. Somatostatin was infused to disable the endocrine pancreas during the experimental period. Insulin was infused in a leg vein of subject 5 for 3 hours at a rate 7× its basal (B) secretion rate along with an infusion of glucagon at a basal rate (I/G ratio of 19) or a rate 7×B (I/G ratio of 3). The insulin-induced fall in glucose was reduced by the extra glucagon (a nadir of 39±1 vs 40±1 mg/dl) as a result of increased glucagon-driven hepatic glucose production (0.7±0.2 vs 1.4±0.2 mg/kg/min). The data are from the control period (hatched bars) and the last 2 hours of the experimental period (solid bars).

Figure 23:
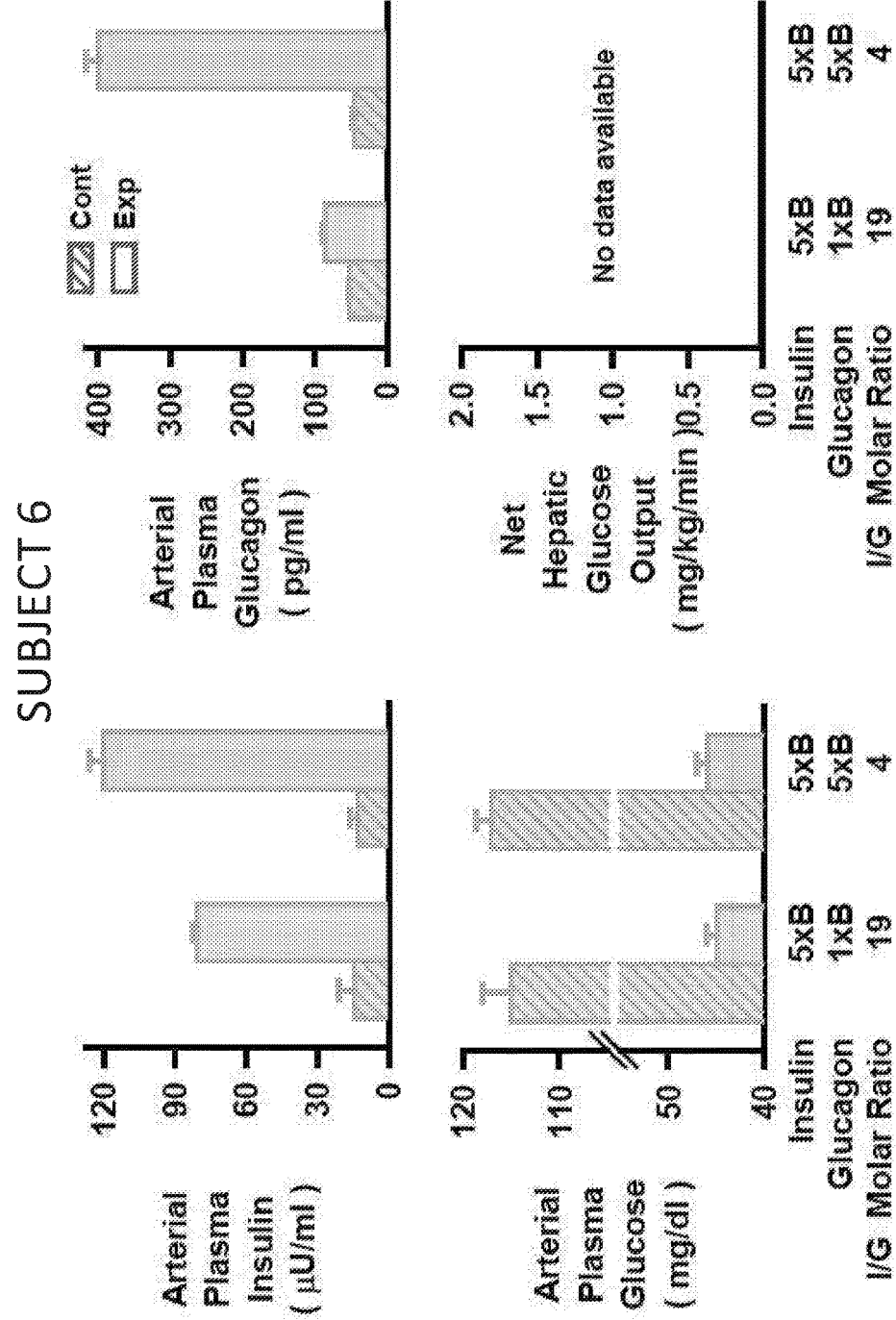

Referring to FIG. 23, data from subject 6 is illustrated. Somatostatin was infused to disable the endocrine pancreas during the experimental period. Insulin was infused in a leg vein of subject 6 for 3 hours at a rate 5× its basal (B) secretion rate along with an infusion of glucagon at a basal rate (I/G Ratio of 19) or a rate 5×B (I/G Ratio of 4). The insulin-induced fall in glucose was not changed by the extra glucagon (a nadir of 45±2 vs 46±2 mg/dl) and net hepatic glucose production was not measured. The data are from the control period (hatched bars) and the last 2 hours of the experimental period (solid bars).

Figure 18:
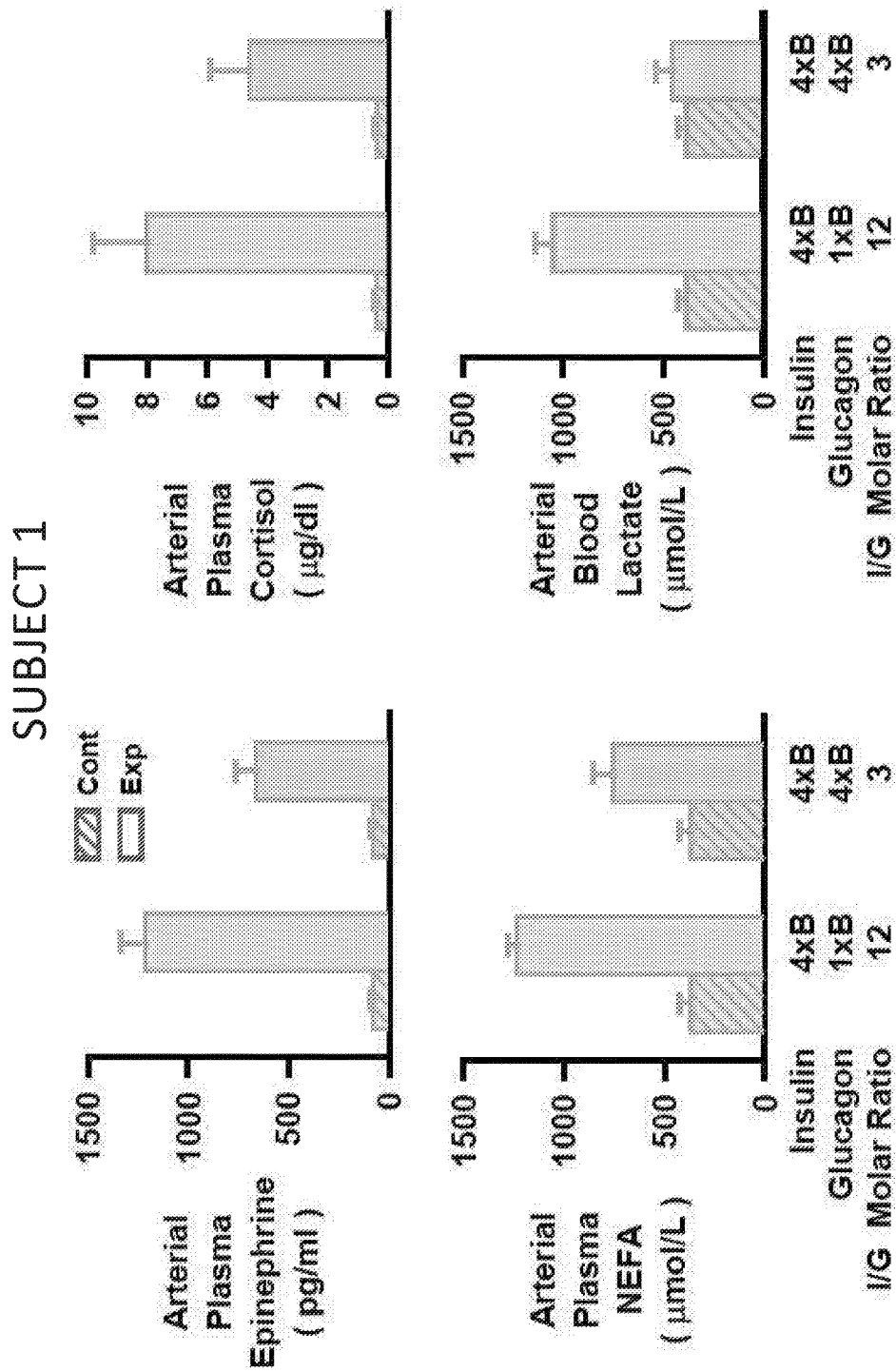

FIGS. 18, 20, 22 and 24 illustrate that when a rise in glucagon accompanied the rise in insulin, there was a reduction in cortisol and epinephrine in the blood which resulted in a reduced lipolytic response in fat, and a reduced glycogenolytic response in muscle. FIG. 18 illustrates data that shows that the increase in glucagon (I/G molar ratio of 3) and/or the reduction in the fall of plasma glucose resulted in a reduction in hypoglycemia associated cortisol release and epinephrine secretion. This in turn reduced the hypoglycemia driven lipolytic effect (smaller increase in NEFA) and the hypoglycemia associated rise in muscle glycogenolysis (smaller increase in blood lactate). The same pattern was seen in subject 2 (FIGS. 19 and 20) with the exception that the hypoglycemic protection was less (5 mg/dl) and the reduction in the response of the sympathetic nervous system was also somewhat less compared to that in subject 1. The same pattern was seen in subject 5, (FIGS. 21 and 22) with the exception that there was little hypoglycemic protection (approximately 1 mg/dl) afforded by the lower I/G molar ratio but there was still a substantial reduction in the sympathetic nervous system response to hypoglycemia. Likewise, in subject 6 (FIGS. 23 and 24), the hypoglycemia protection was minimal but there was a dramatic decrease in the sympathetic nervous system response to hypoglycemia in the presence of elevated glucagon (i.e. a low I/G molar ratio).

Referring to FIG. 18, data from subject 1 is illustrated. Somatostatin was infused to disable the endocrine pancreas during the experimental period. Raising insulin infusion in the presence of a proportional rise in glucagon infusion (as opposed to keeping glucagon basal) resulted in a halving of the response of the autonomic nervous system to hypoglycemia (Epi 1130±122 vs 668±100 pg/ml & Cortisol 8.0±0.9 vs 4.6±1.3 µg/dl) and consequently a much smaller increase in lipolysis (NEFA; Δ865 vs Δ385 µmol/L) and muscle glycogenolysis (lactate Δ662 vs Δ64 µmol/L). Data are from the control period (hatched bars) and the last 2 hours of the experimental period (solid bars).

Figure 20:
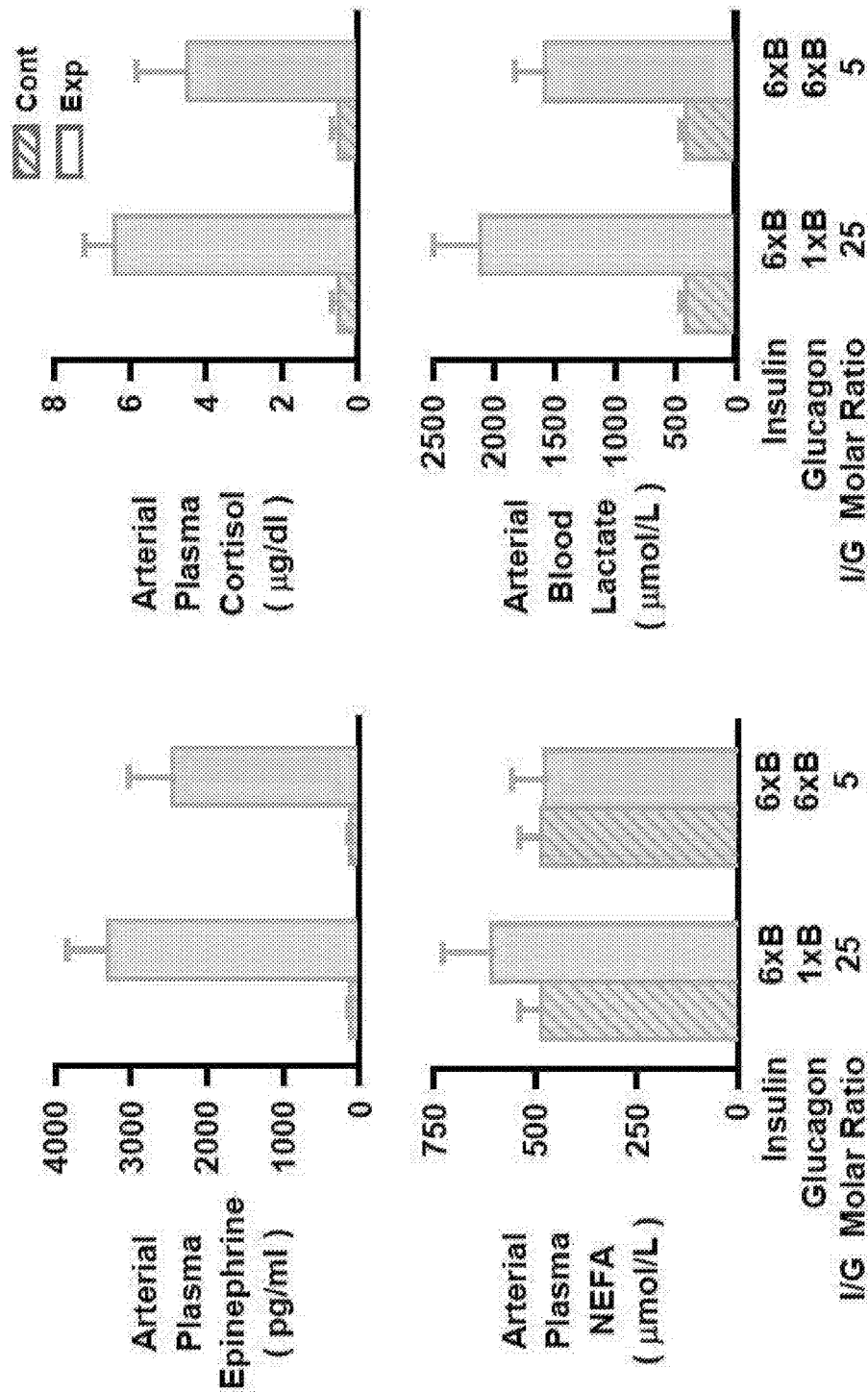

Referring now to FIG. 20, data from subject 2 is illustrated. Somatostatin was infused to disable the endocrine pancreas during the experimental period. Raising insulin infusion in the presence of a proportional rise in glucagon infusion (as opposed to keeping glucagon basal) resulted in a reduction of the response of the autonomic nervous system by ⅓ to hypoglycemia (Epi 3318±523 vs 2449±547 pg/ml & Cortisol 6.4±0.8 vs 4.5±1.3 µg/dl) and consequently a much smaller increase in lipolysis (NEFA; Δ121 vs Δ9 µmol/L) and muscle glycogenolysis (lactate Δ1690 vs Δ1162 µmol/L). Data are from the control period (hatched bars) and the last 2 hours of the experimental period (solid bars).

Figure 22:
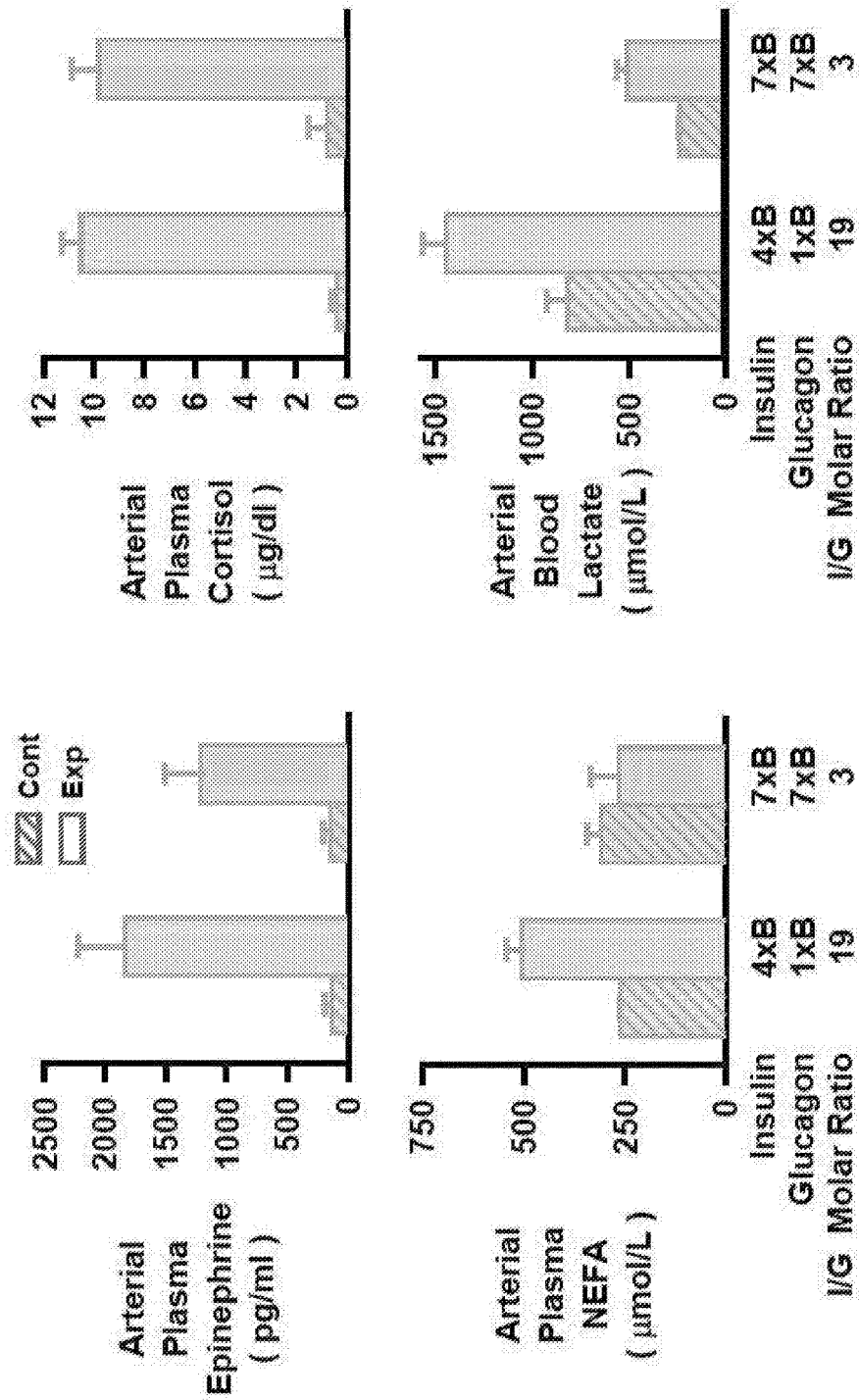

Referring now to FIG. 22, data from subject 5 is illustrated. Somatostatin was infused to disable the endocrine pancreas during the experimental period. Raising insulin infusion in the presence of a proportional rise in glucagon infusion (as opposed to keeping glucagon basal) resulted in a reduction of the response of the autonomic nervous system by ⅓ to hypoglycemia (Epi 1841±393 vs 1207±300 pg/ml & Cortisol 10.5±0.8 vs 8.8±1.2 µg/dl) and consequently a much smaller increase in lipolysis (NEFA; Δ242 vs Δ0 µmol/L) and muscle glycogenolysis (lactate Δ575 vs Δ253 µmol/L). Data are from the control period (hatched bars) and the last 2 hours of the experimental period (solid bars).

Figure 24:
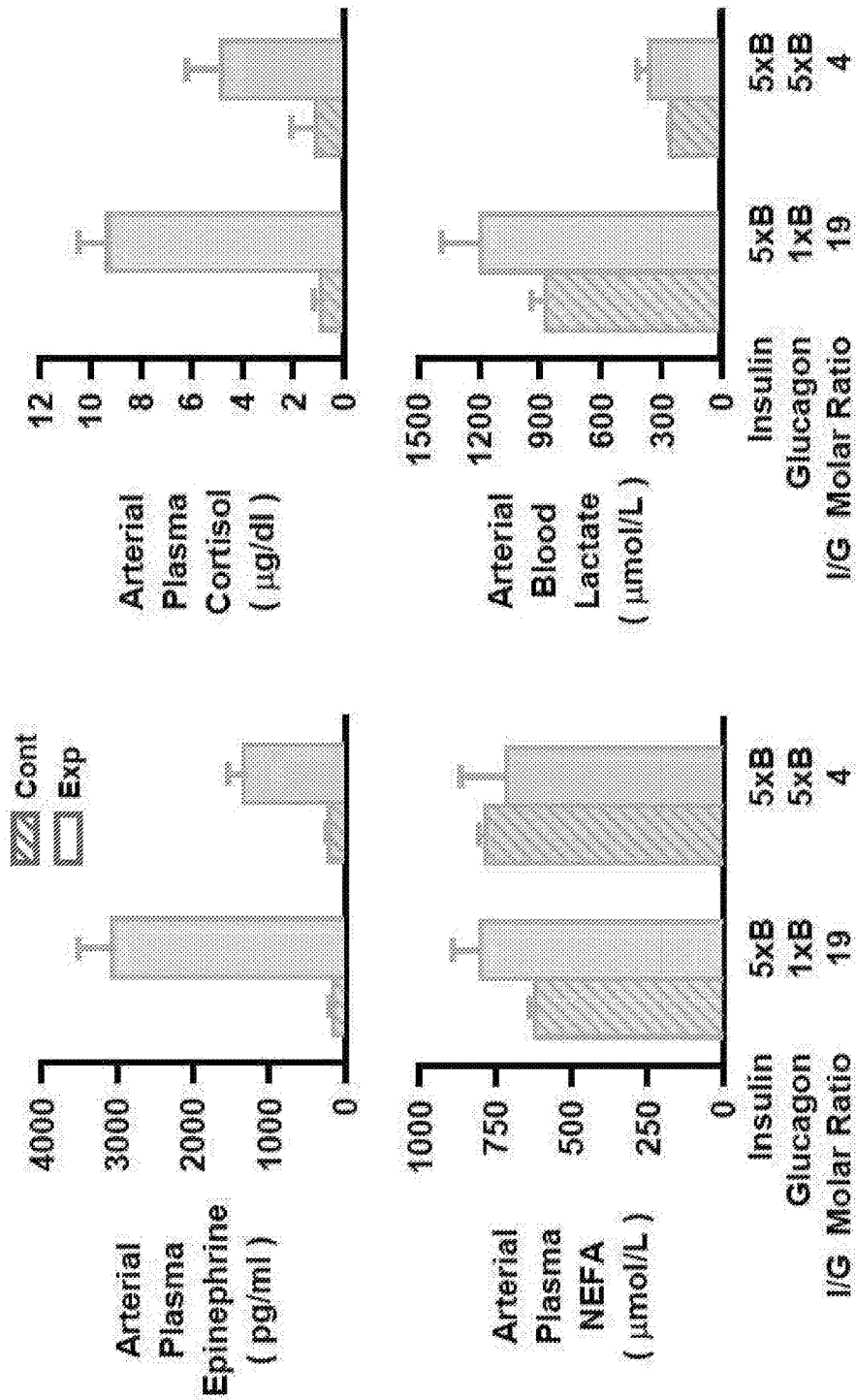

Referring now to FIG. 24, data from subject 6 is illustrated. Somatostatin was infused to disable the endocrine pancreas during the experimental period. Raising insulin infusion in the presence of a proportional rise in glucagon infusion (as opposed to keeping glucagon basal) resulted in a halving of the response of the autonomic nervous system to hypoglycemia (Epi 3060±450 vs 1334±195 pg/ml & Cortisol 9.3±1.2 vs 4.8±1.4 μg/dl) and consequently a reduced increase in lipolysis (NEFA; Δ182 vs Δ68 μmol/L) and muscle glycogenolysis (Lactate Δ396 vs Δ105 μmol/L). Data are from the control period (hatched bars) and the last 2 hours of the experimental period (solid bars).

Collectively, these data show that bringing about hyperinsulinemia in the presence of proportionally altered glucagon (sustained low I/G molar ratio) can reduce the depth of hypoglycemia in most canine subjects, and importantly can reduce the dependence on the sympathetic nervous system for defense of the blood sugar in all animals. Elevating glucagon in parallel to insulin reduced the hypoglycemic response to insulin while at the same time reducing reliance on the sympathetic nervous system for defense of the blood sugar. It should be stressed that when plasma glucose is in the 40's, small differences in glycemia (2-5 mg/dl) can have a dramatic impact on the counter-regulatory hormone response to insulin induced hypoglycemia. Thus, even a small decrease in the magnitude of the fall in glucose is clinically significant.

Figure 25:
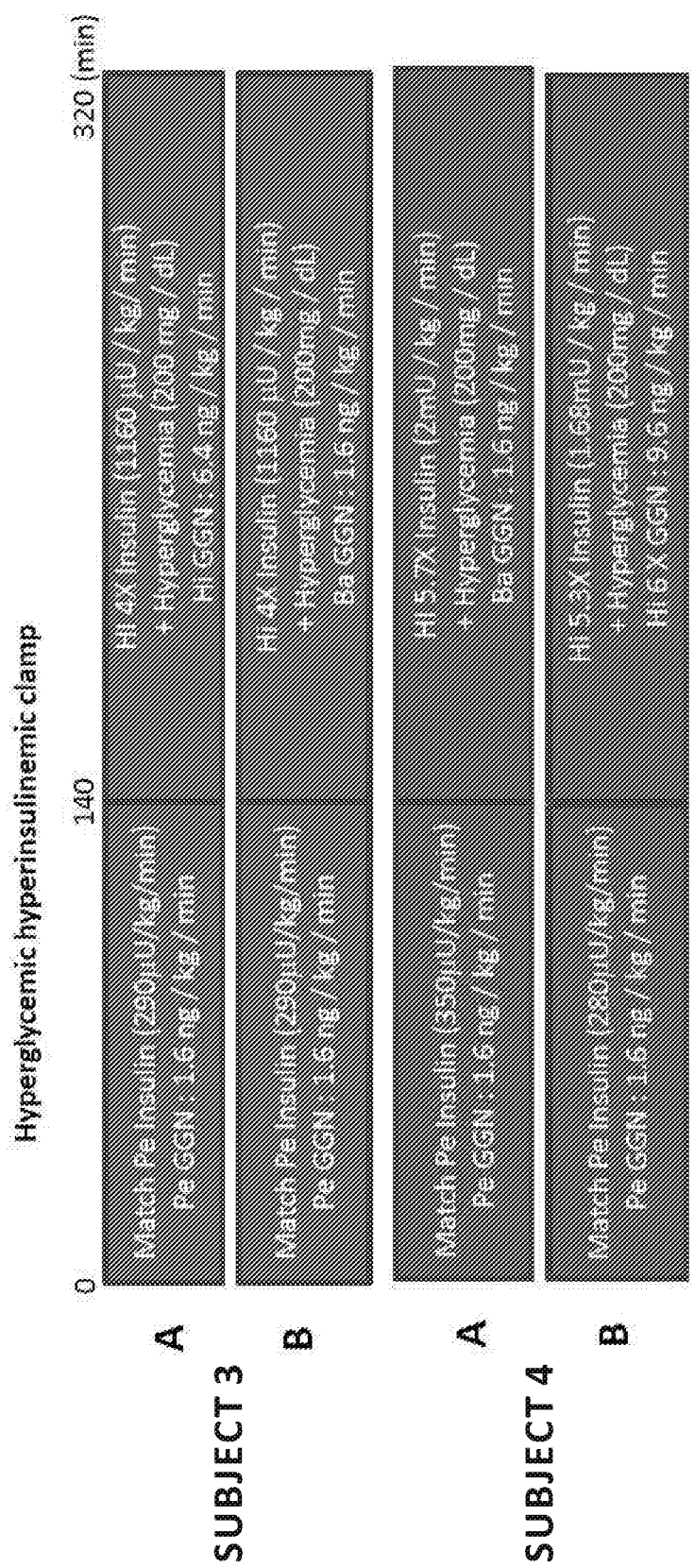

If keeping a low I/G molar ratio in the face of increased insulin delivery protects against hypoglycemia and/or the response to it, the question arises as to whether it would impair insulin action in a hyperglycemic situation. Applicant carried out paired experiments on two of the subjects (subject 3 and 4). The protocol (as shown in FIG. 25) consisted of a 140 min clamp period (as with the hypoglycemic studies described above), followed by an experimental period in which glucose was clamped at approximately 210 ng/dl and in which insulin was increased 4 to 5.7-fold while glucagon was kept at basal (unchanged from 1.6 ng/kg/min) or increased (4 or 6-fold).

Figure 26:
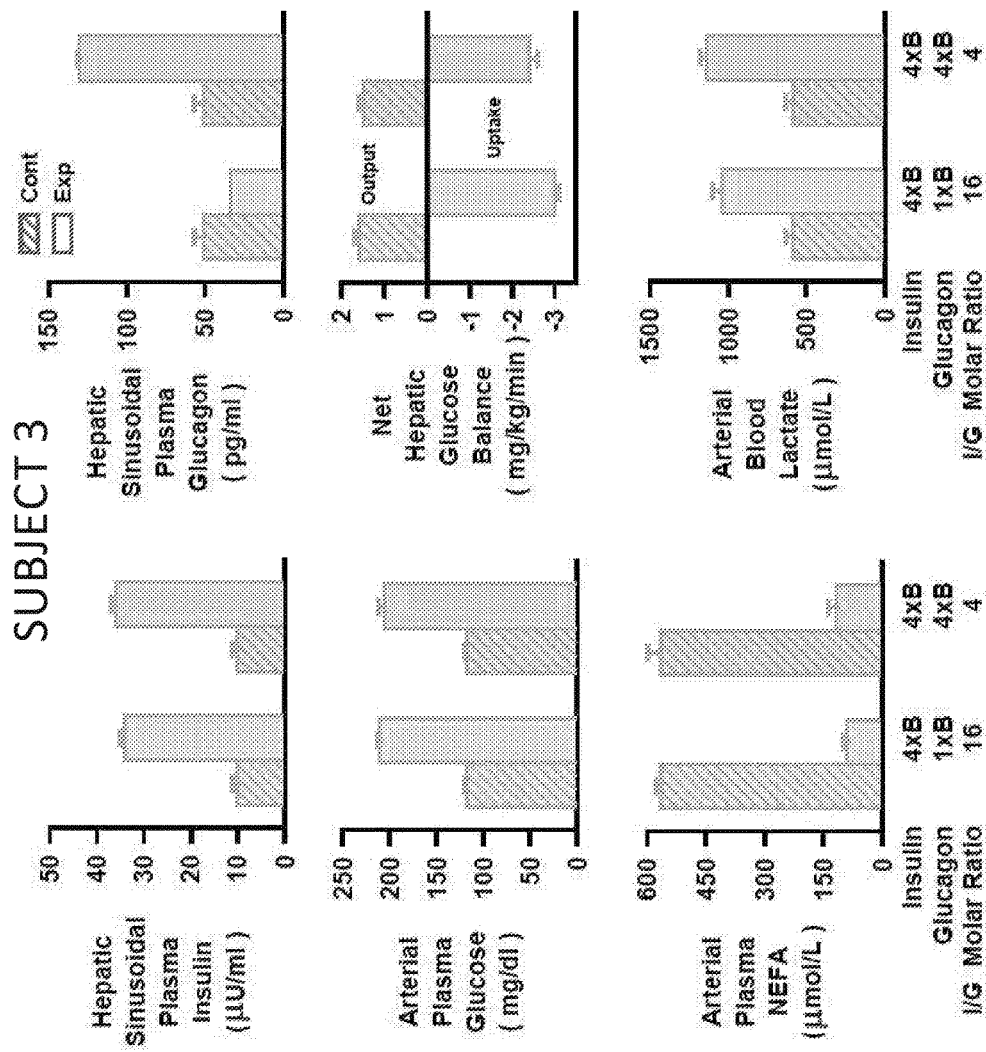
Figure 27:
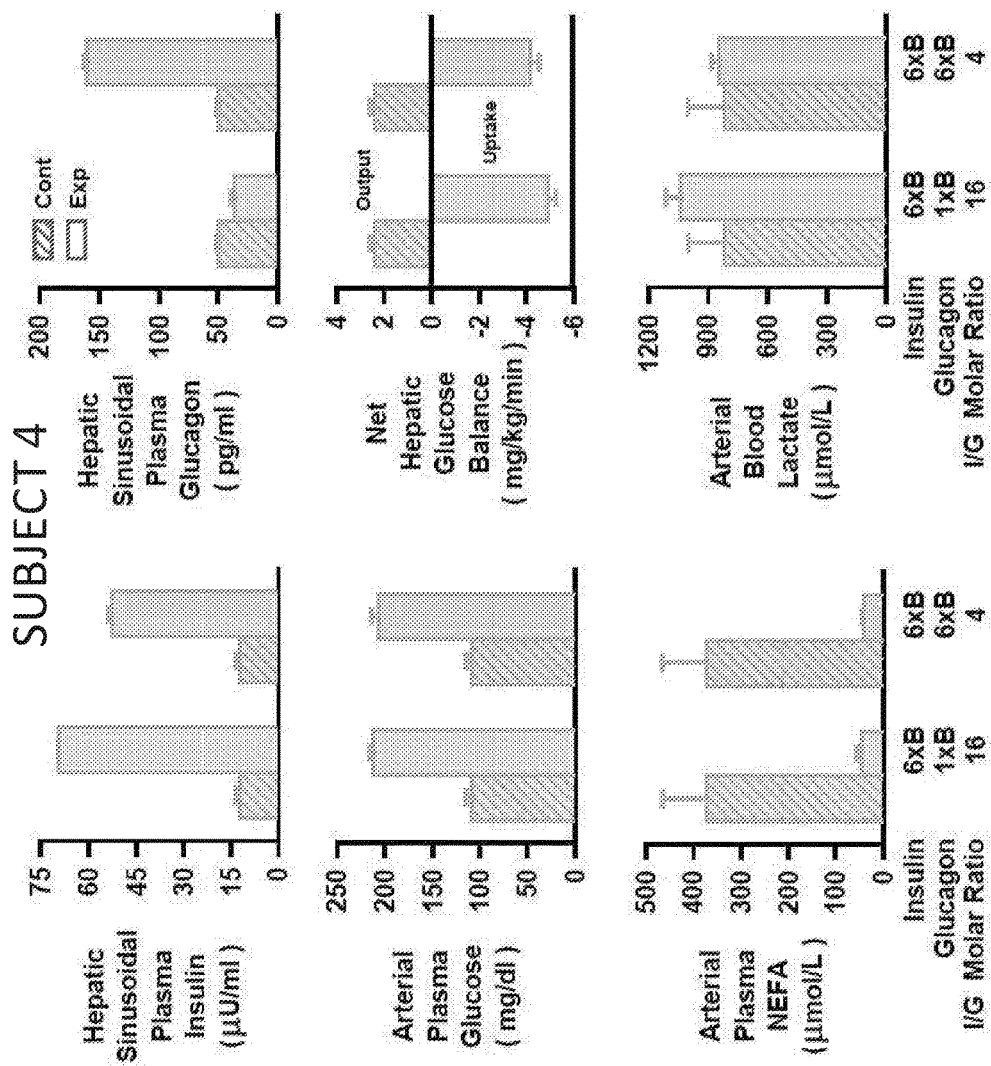
Figure 28:
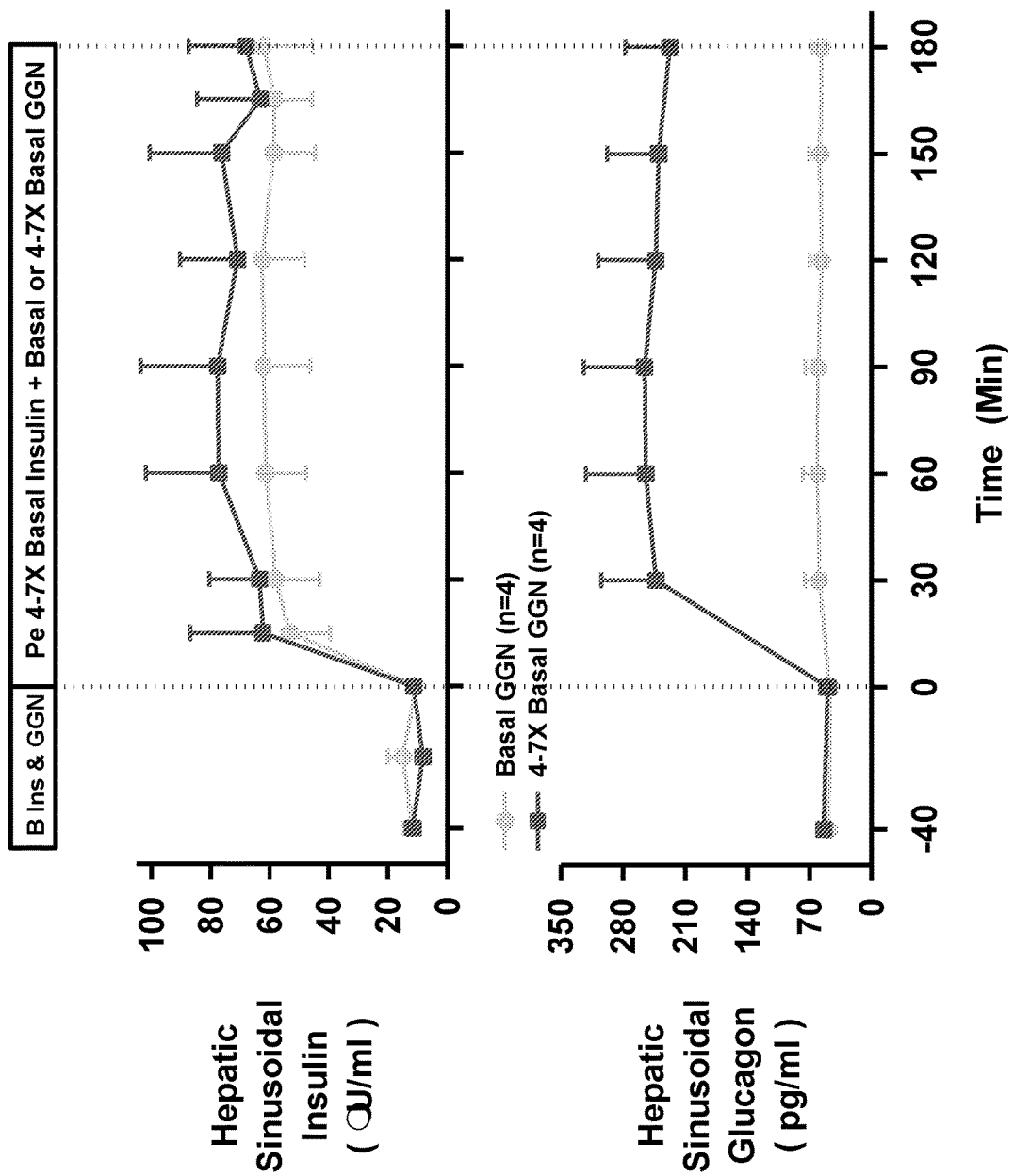

FIGS. 26 and 27 illustrate similar data and show that net hepatic glucose uptake, lipolytic suppression and lactate levels were virtually unaffected by the extra glucagon. Thus, co-infusion of insulin and glucagon at a low I/G molar ratio (e.g. 3-5) protects against hypoglycemia without having a deleterious effect on hepatic glucose uptake under hyperglycemic conditions.

Referring now to FIG. 26, data from subject 3 is illustrated. During the experimental period, somatostatin was infused to disable the endocrine pancreas. Insulin was infused at a rate 4× basal (B) for 3 hours, along with either 1×B or 4×B glucagon. The glucose level was clamped at approximately 210 mg/dl. The extra glucagon (4×B vs 1×B respectively, which changed the I/G molar ratio from 16 to 4) had no impact on the switch from net hepatic glucose output (1.5±0.1 mg/kg/min) to uptake (2.4±0.2 vs 3.0±0.2 mg/kg/min), nor on the suppression of plasma NEFA (567±3 μmol/L to 116±21 vs 89±10 μmol/L), nor on the rise in blood lactate (582±51 μmol/L to 1141±40 vs 1040±65 μmol/L). The data are from the control period (hatched bars) and the last 2 hours of the experimental period (solid bars).

Referring now to FIG. 27, data from subject 4 is illustrated. During the experimental period, somatostatin was infused to disable the endocrine pancreas. Insulin was infused at a rate 6× basal (B) for 3 hours, along with either 1×B or 6×B glucagon. The glucose level was clamped at approximately 210 mg/dl. The extra glucagon (6×B vs 1×B respectively, which changed the I/G molar ratio from 16 to 4) had no impact on the switch from net hepatic glucose output (1.52.4±0.2 mg/kg/min) to uptake (4.9±0.3 vs 4.2±0.4 mg/kg/min), nor on the suppression of plasma NEFA (371±94 μmol/L to 47±10 vs 41±3 μmol/L), nor on the rise in blood lactate (819±182 μmol/L to 1040±74 vs 845±38 μmol/L). The data are from the control period (hatched bars) and the last 2 hours of the experimental period (solid bars).

FIGS. 28 to 34 illustrate mean data from the 4 hypoglycemic subjects and the 2 hyperglycemic subjects (described hereabove), plotted over time. In the hypoglycemic subjects, the rise in insulin (approximately 50 μU/ml) was similar whether glucagon was increased proportionally (I/G molar ratio 3-5) or not (I/G molar ratio 12-25). Glucagon either increased by approximately 180 pg/ml or did not significantly change.

Figure 29:
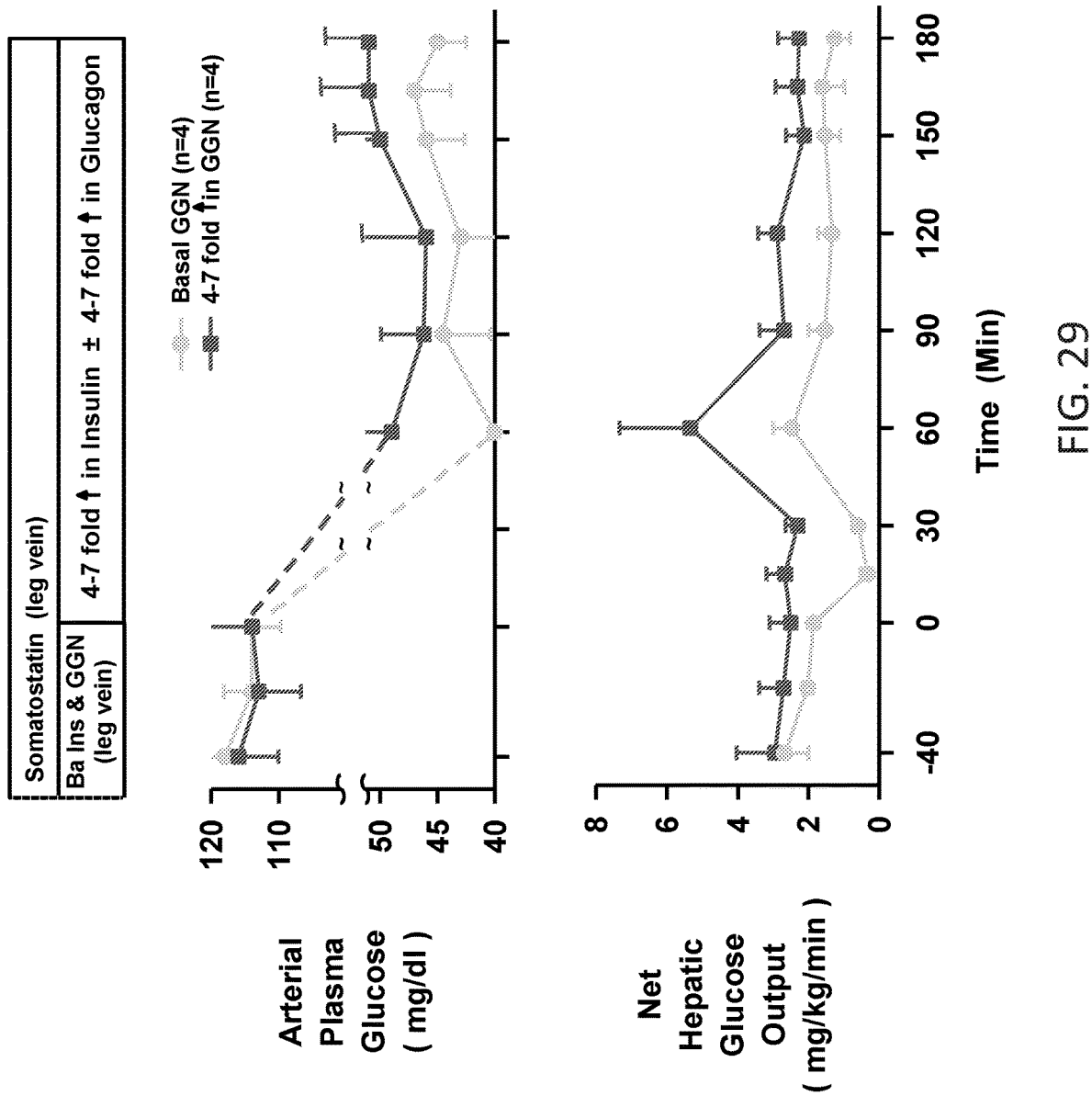
Figure 30:
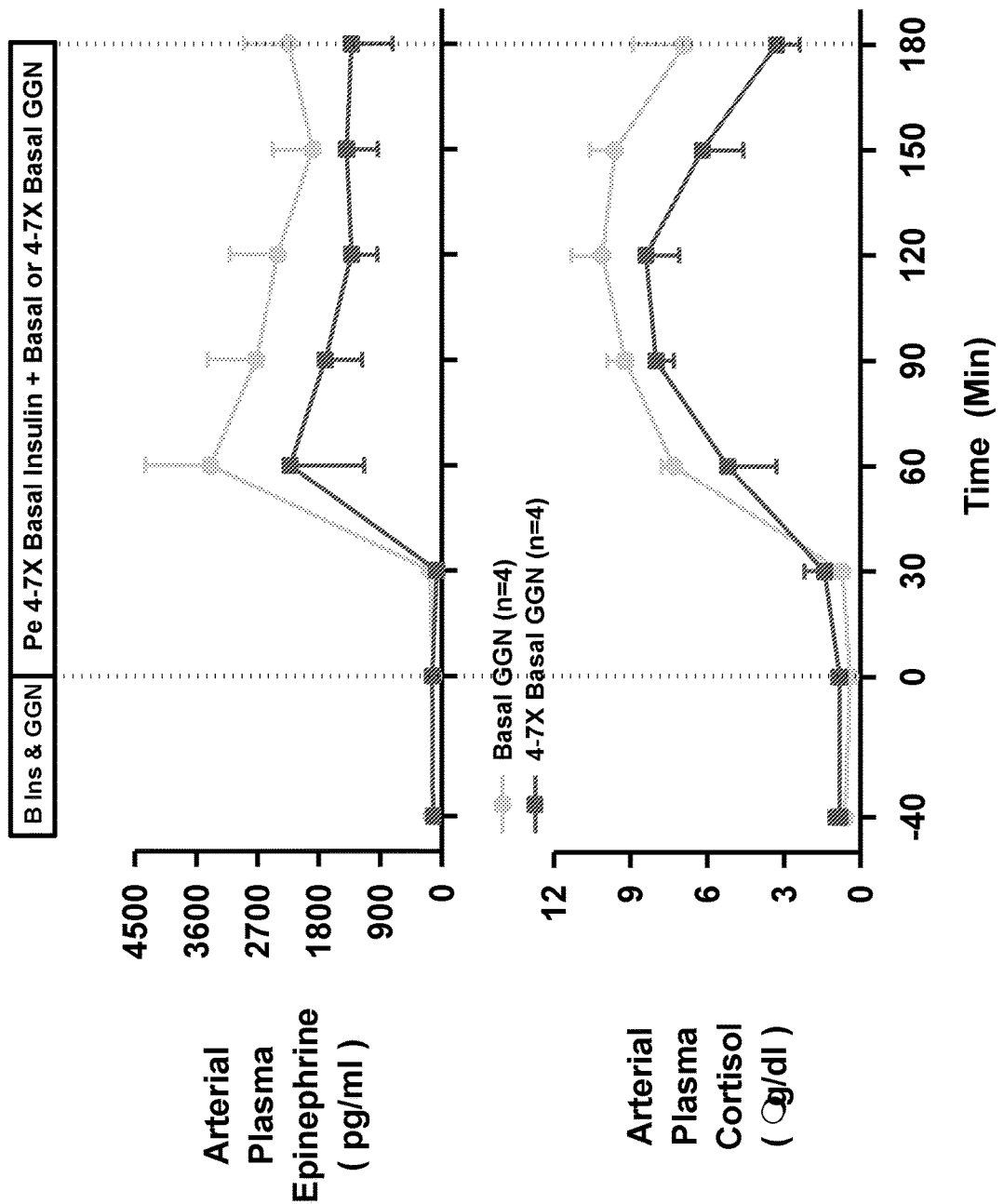
Figure 31:
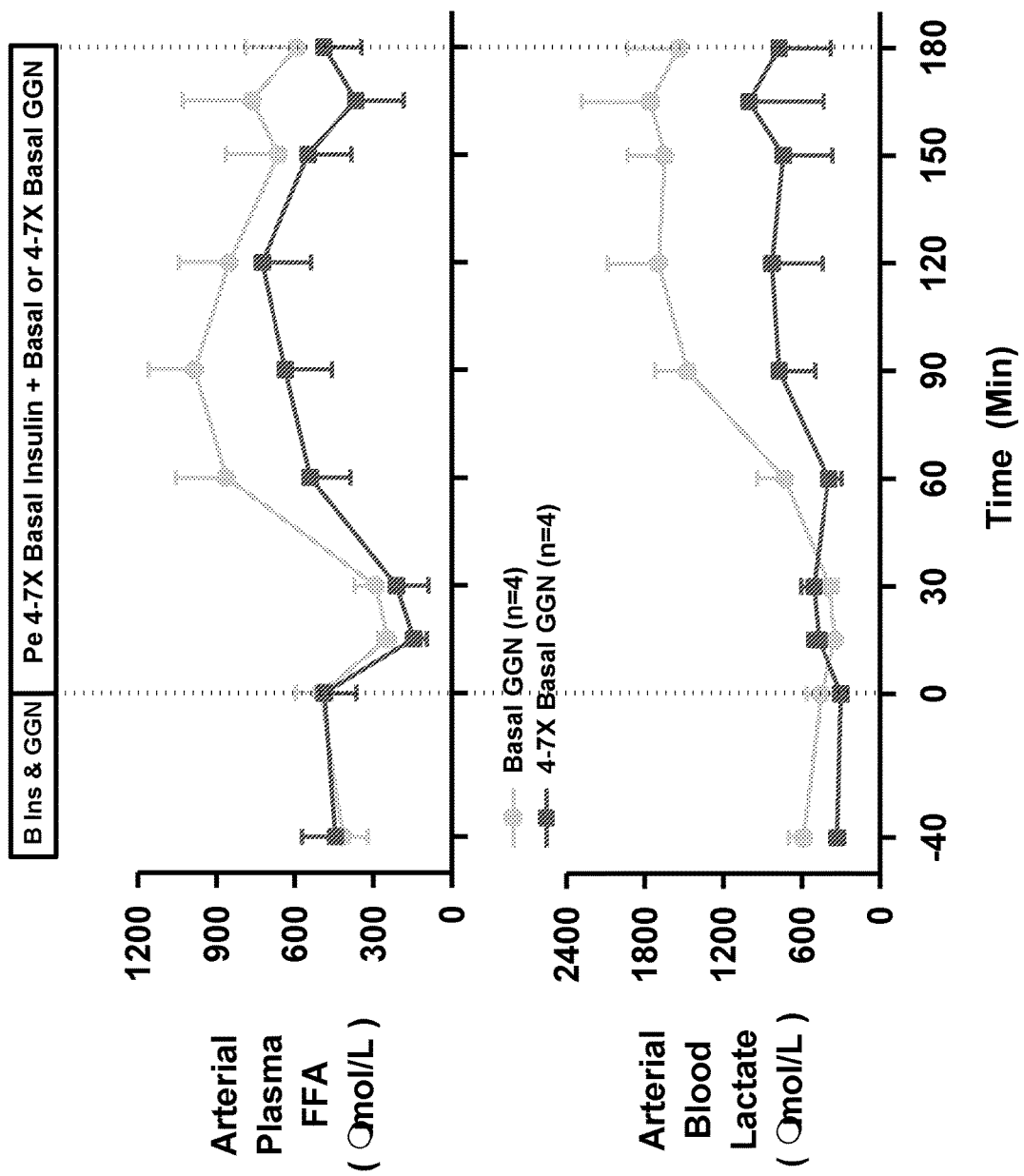

FIG. 29 illustrates data that show that in the presence of elevated glucagon, there was a reduction in the insulin induced drop in plasma glucose. This reduction was associated with, and probably caused by, an increase in net hepatic glucose output. The epinephrine and cortisol responses to hypoglycemia were reduced when glucagon was elevated (as shown in FIG. 30). Similarly, the hypoglycemia driven rise in NEFA (lipolysis) and blood lactate (muscle glycogenolysis) were reduced by the presence of extra glucagon (as shown in FIG. 31).

Figure 32:
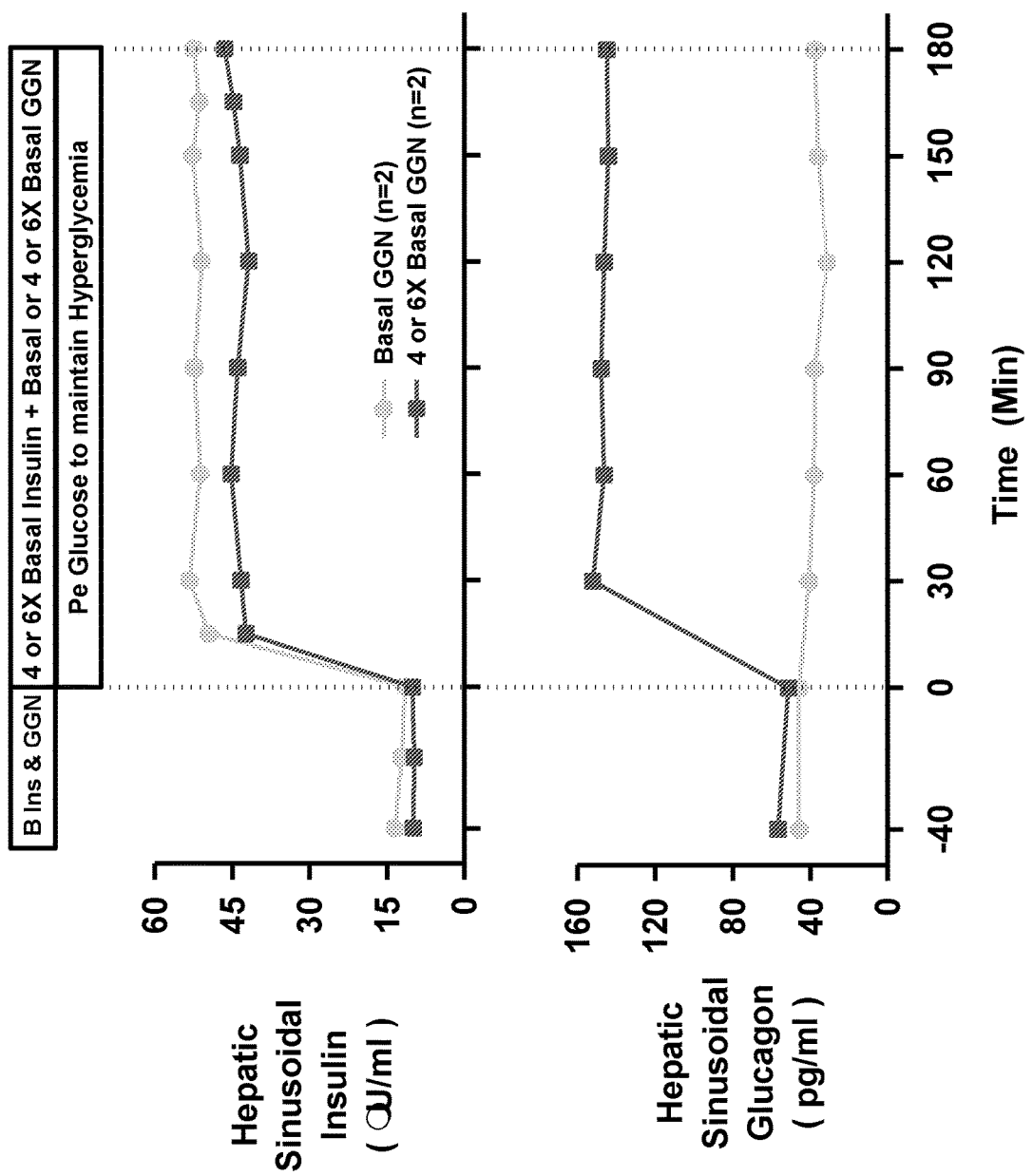
Figure 33:
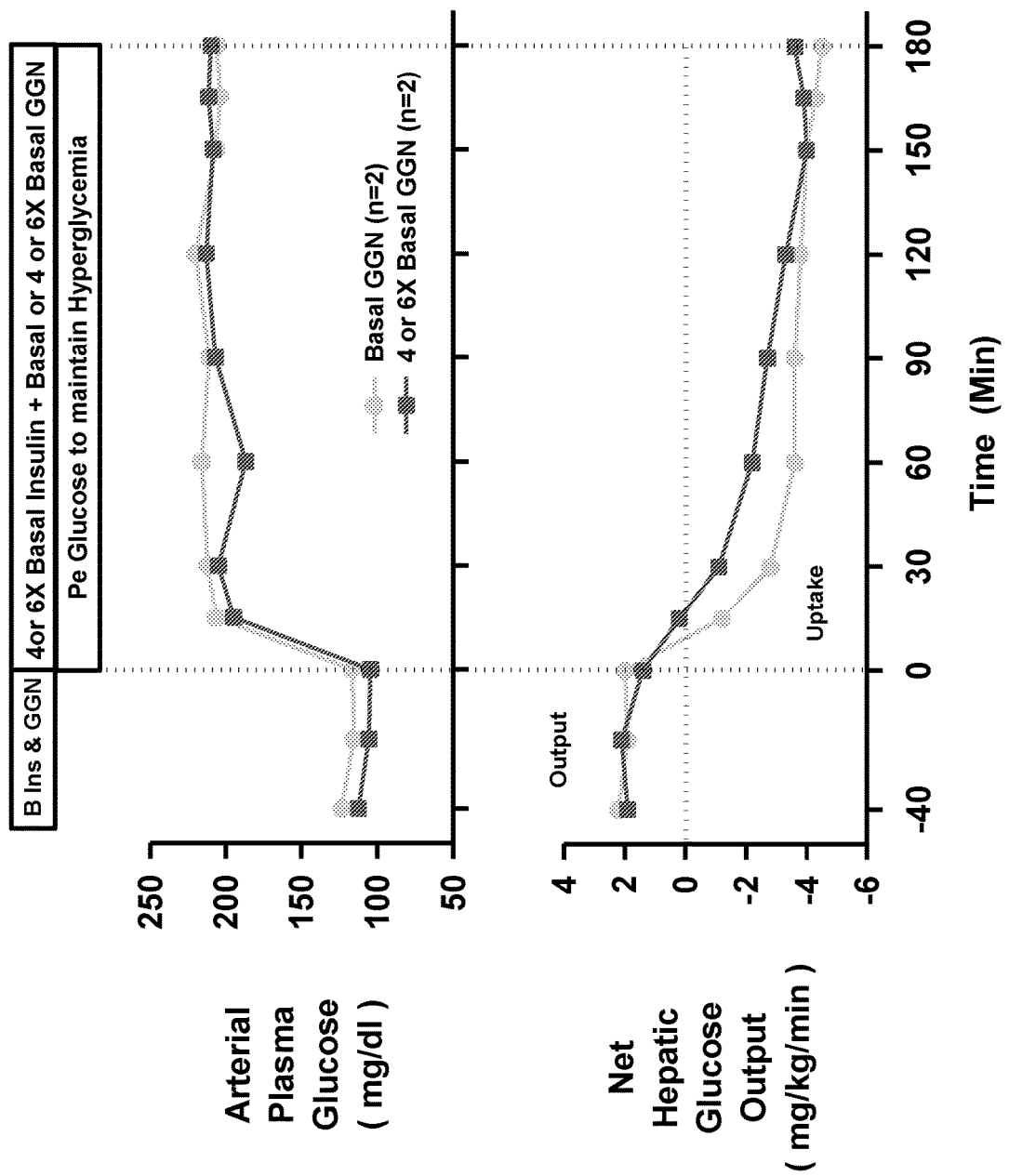
Figure 34:
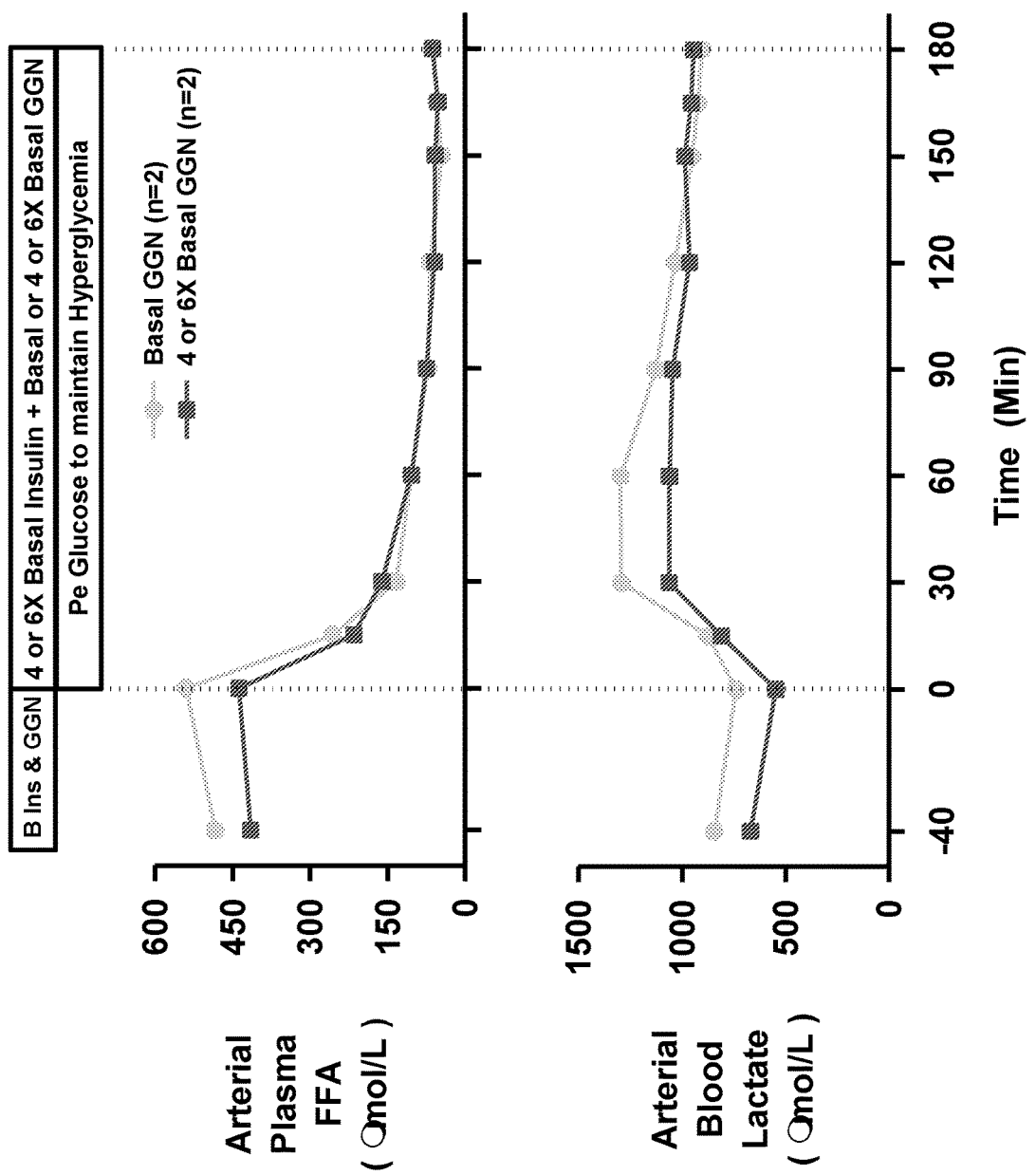

FIGS. 32-34 illustrate the mean data over time for the hyperglycemic studies. Once again, the rise in insulin was similar whether glucagon was elevated or not. The plasma glucose level was clamped at approximately 210 mg/dl in both protocols. In response to the rise in insulin and glucose, the liver switched from net glucose output to uptake. The transition to net hepatic glucose uptake occurred somewhat more slowly when glucagon was elevated but over the last 90 min of the experimental period there was no difference in net hepatic glucose uptake. Similarly, the fall in FFA (lipolysis) and the rise in lactate (lactate spillover from liver) were almost identical. Thus, a composition 200 with a low I/G molar ratio, could protect from hypoglycemia without appreciably impairing hepatic glucose uptake under hyperglycemic conditions.

Applicant's further studies include co-administering insulin and glucagon subcutaneously. The experiments were carried out using two infusion pumps, such as infusion pumps 100a and 100b described hereabove in reference to FIG. 1B. Each of the first 8 experiments of this type (2 on each of 4 subjects, subjects 7, 8, 9, and 10) consisted of a control period (−30 to 0 min) followed by a period (0-180 min) in which somatostatin was infused to inhibit the endocrine pancreas. At the same time, basal infusions of insulin (0.3 or 0. 4 mU/kg/min) and glucagon (1.6 to 2.0 ng/kg/min) were given. The goal was to clamp the plasma glucose level at a basal value. Clearly somatostatin inhibited endogenous insulin and glucagon secretion quickly and the subcutaneous infusions failed to restore the basal hormone levels in a timely fashion. Both plasma glucagon and insulin levels initially fell (15 min) and took 1-2 hours to recover. In four additional experiments on another subject (subject 11), the start of the somatostatin infusion was delayed by 60 or 90 min to prevent the transient drop in insulin and glucagon. The insulin infusion rate of 0.4 mU/kg/min produced an average arterial plasma insulin level of 10-12 μU/ml by the end of the basal period, although the average value from subject to subject ranged from 1 to 28 μU/ml. Thus, in addition to issues surrounding the delay in the rise in plasma insulin, the inherent variability evident when using the subcutaneous route of delivery was high. Nevertheless, an insulin infusion rate of 0.4 mU/kg/min (on average) was adequate for basal replacement.

Figure 35:
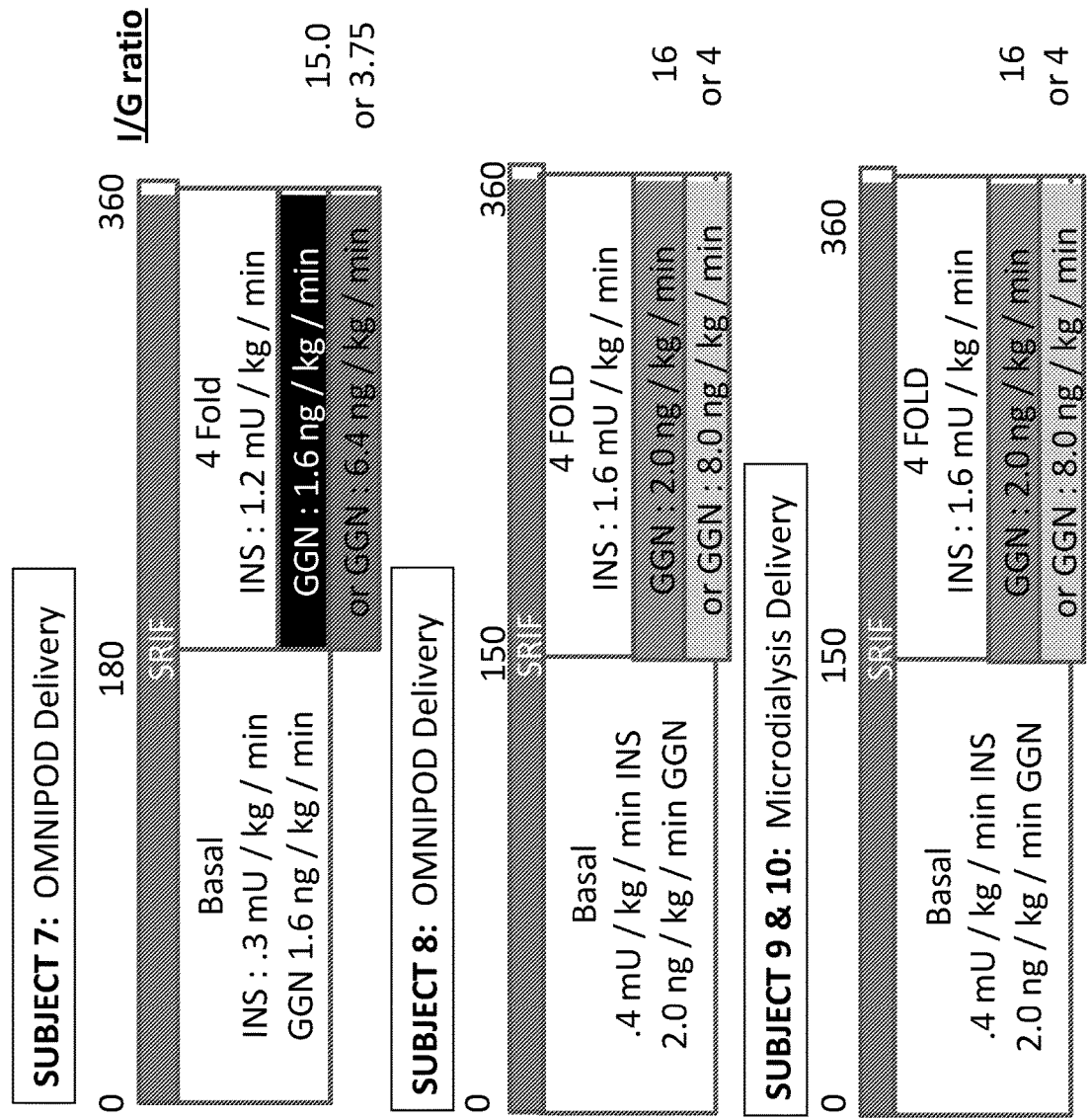
Figure 36:
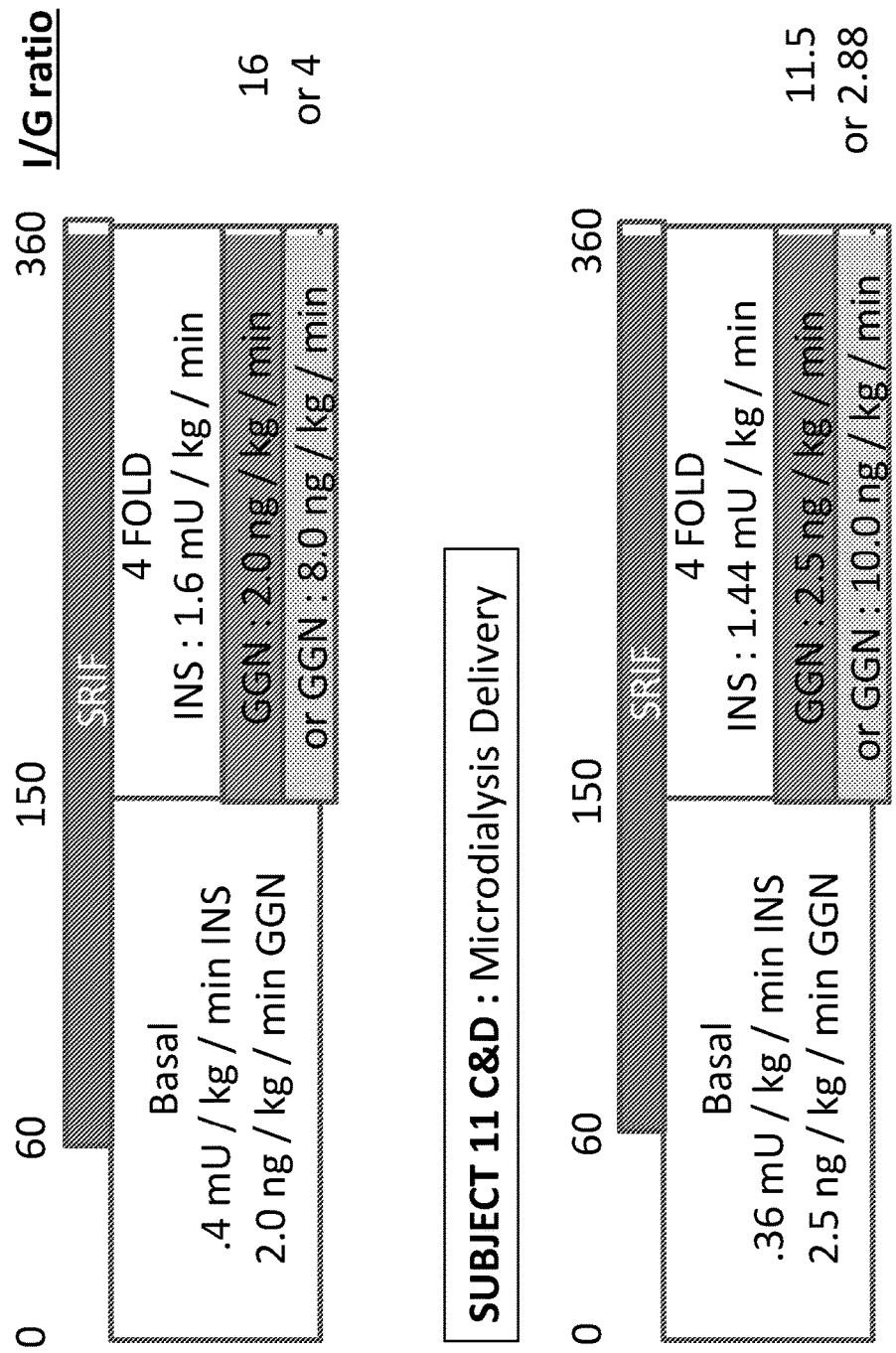
Figure 37:
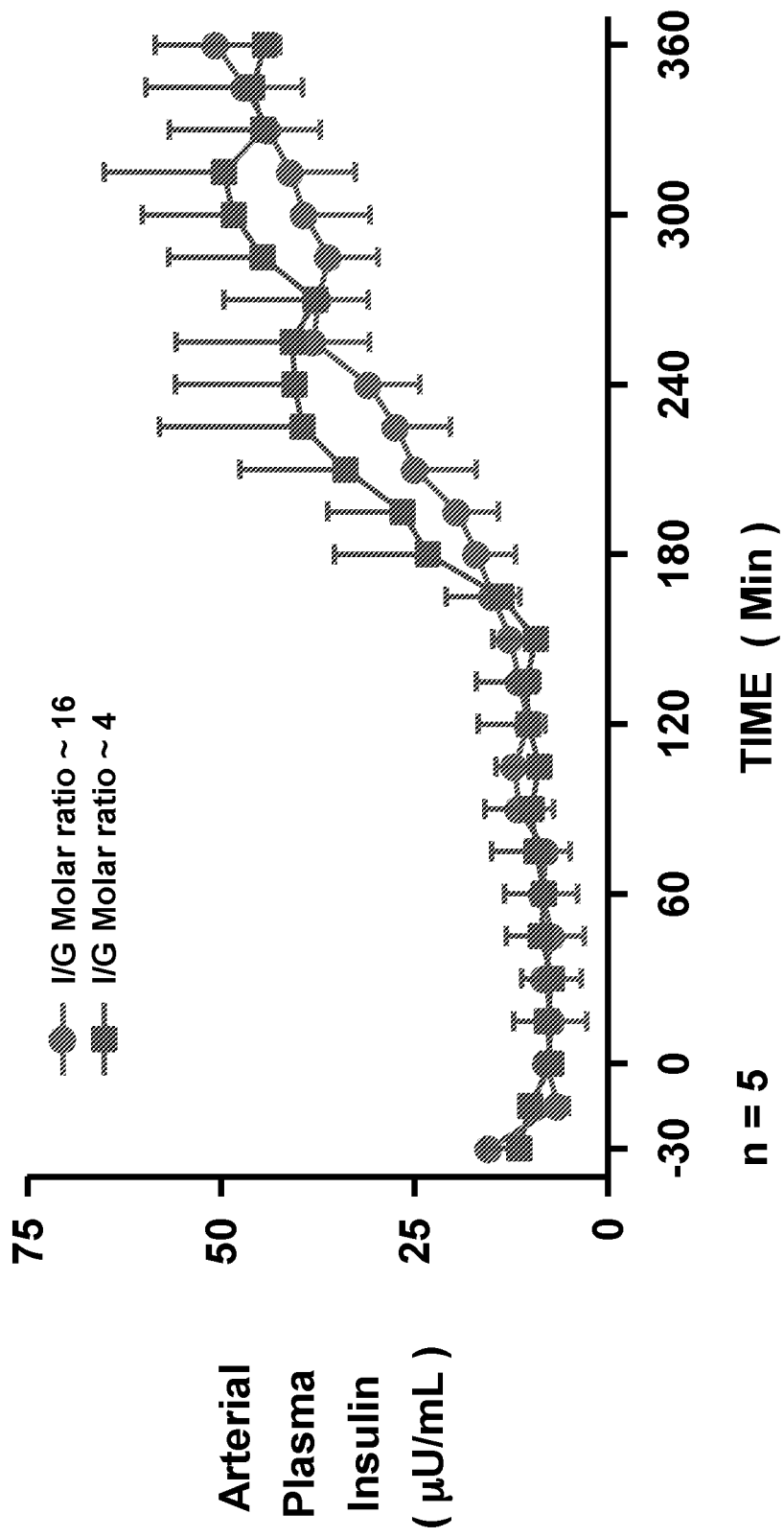
Figure 38:
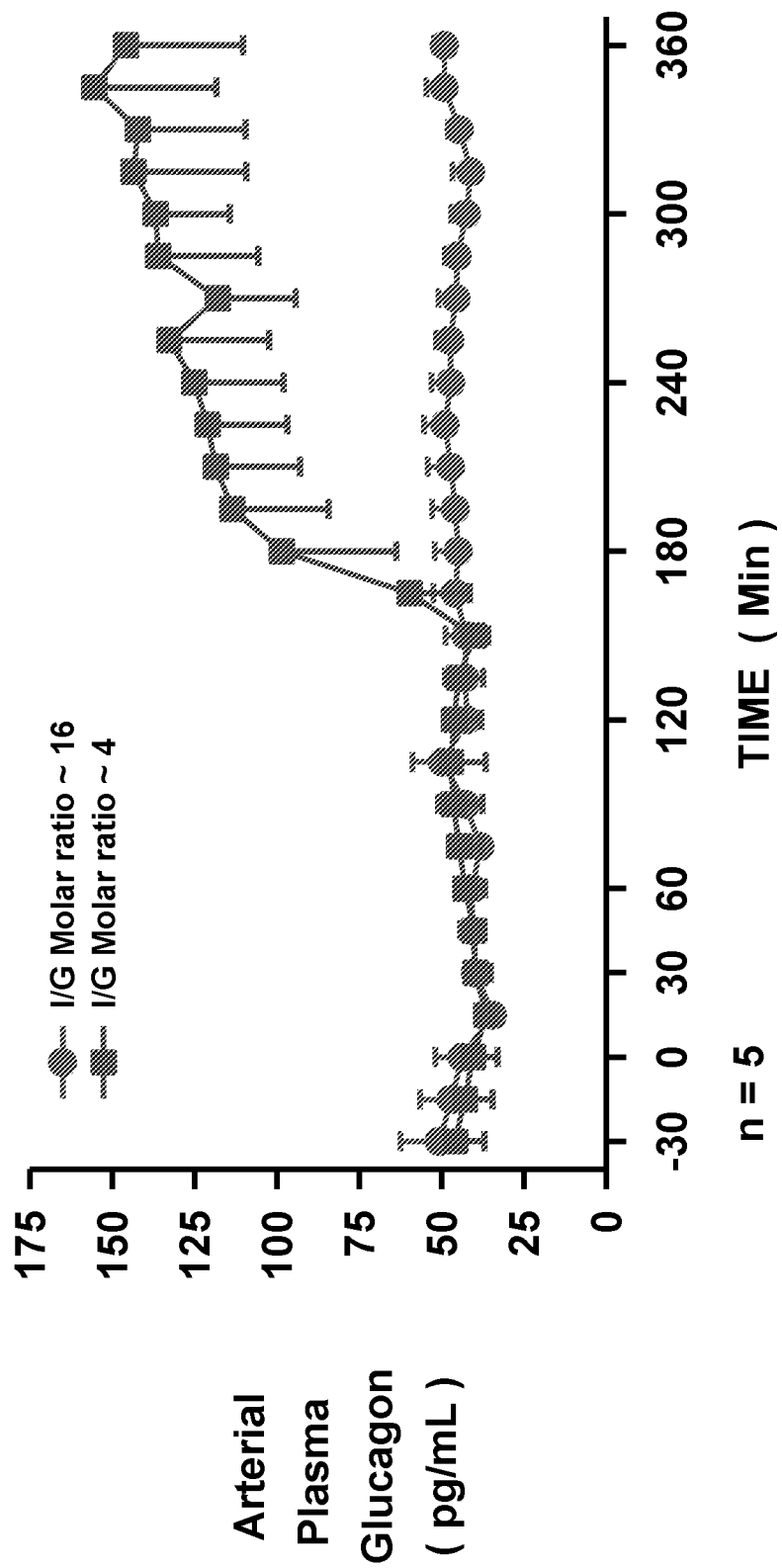
Figure 39:
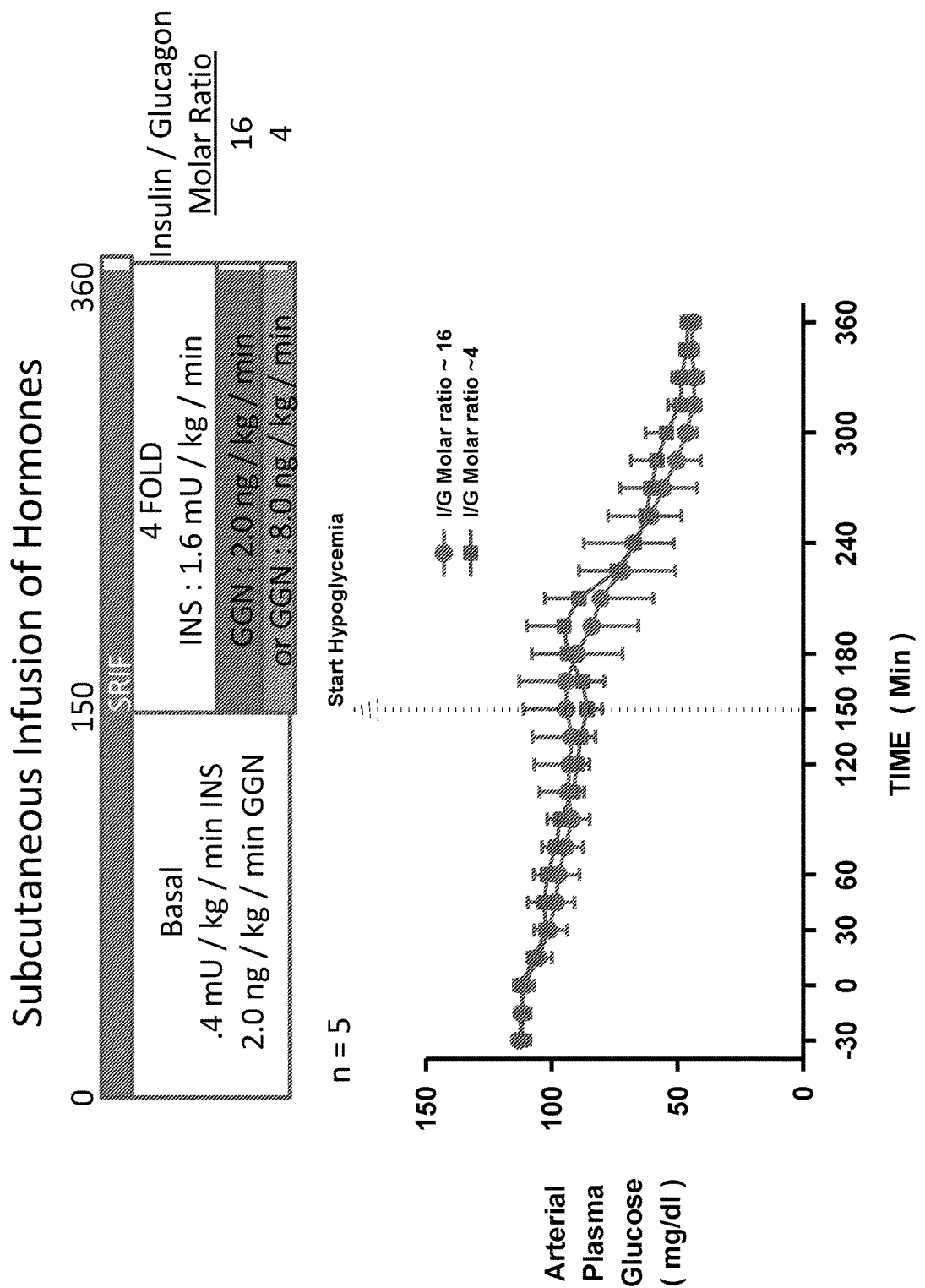
Figure 40:
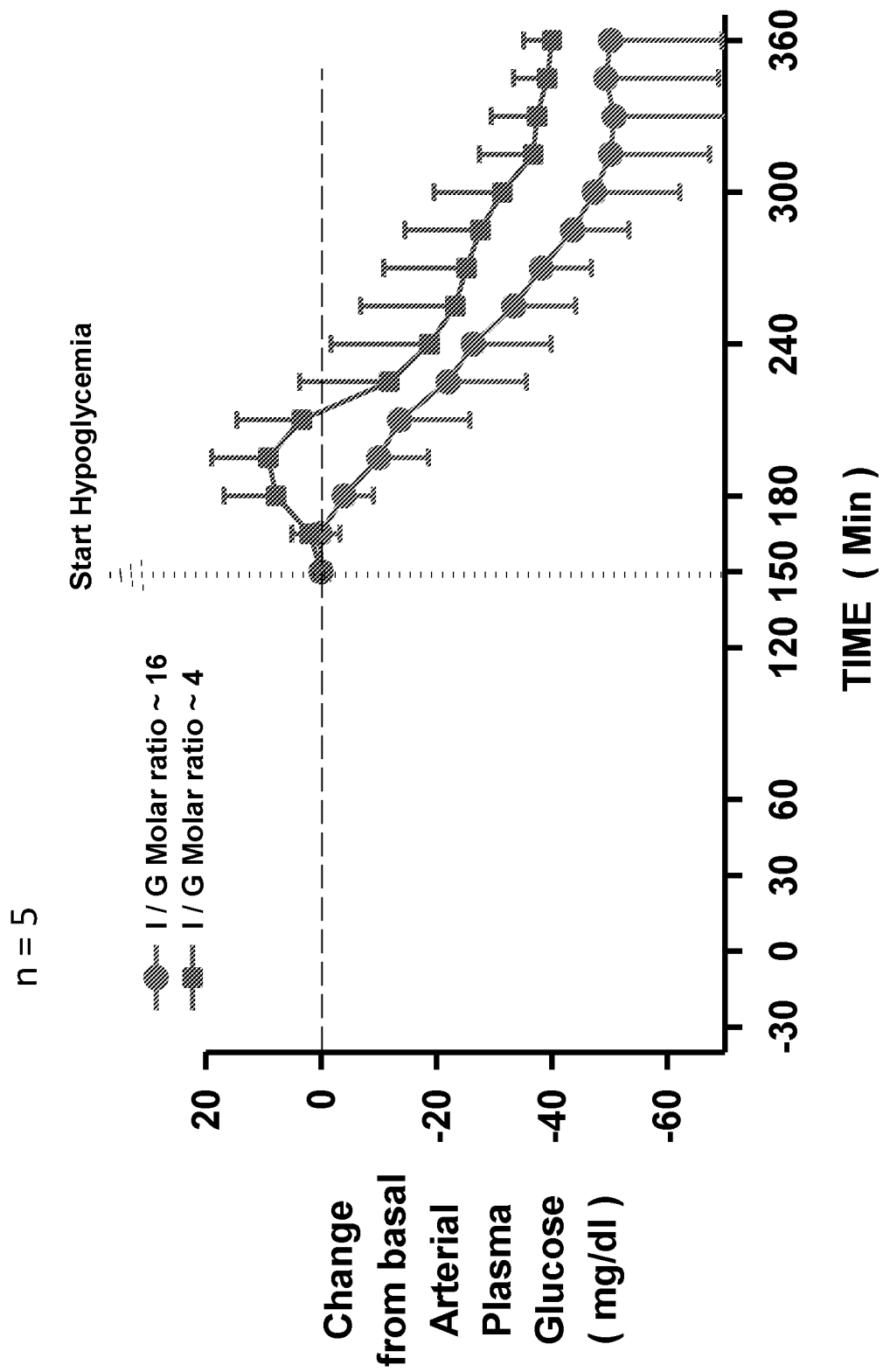
Figure 41:
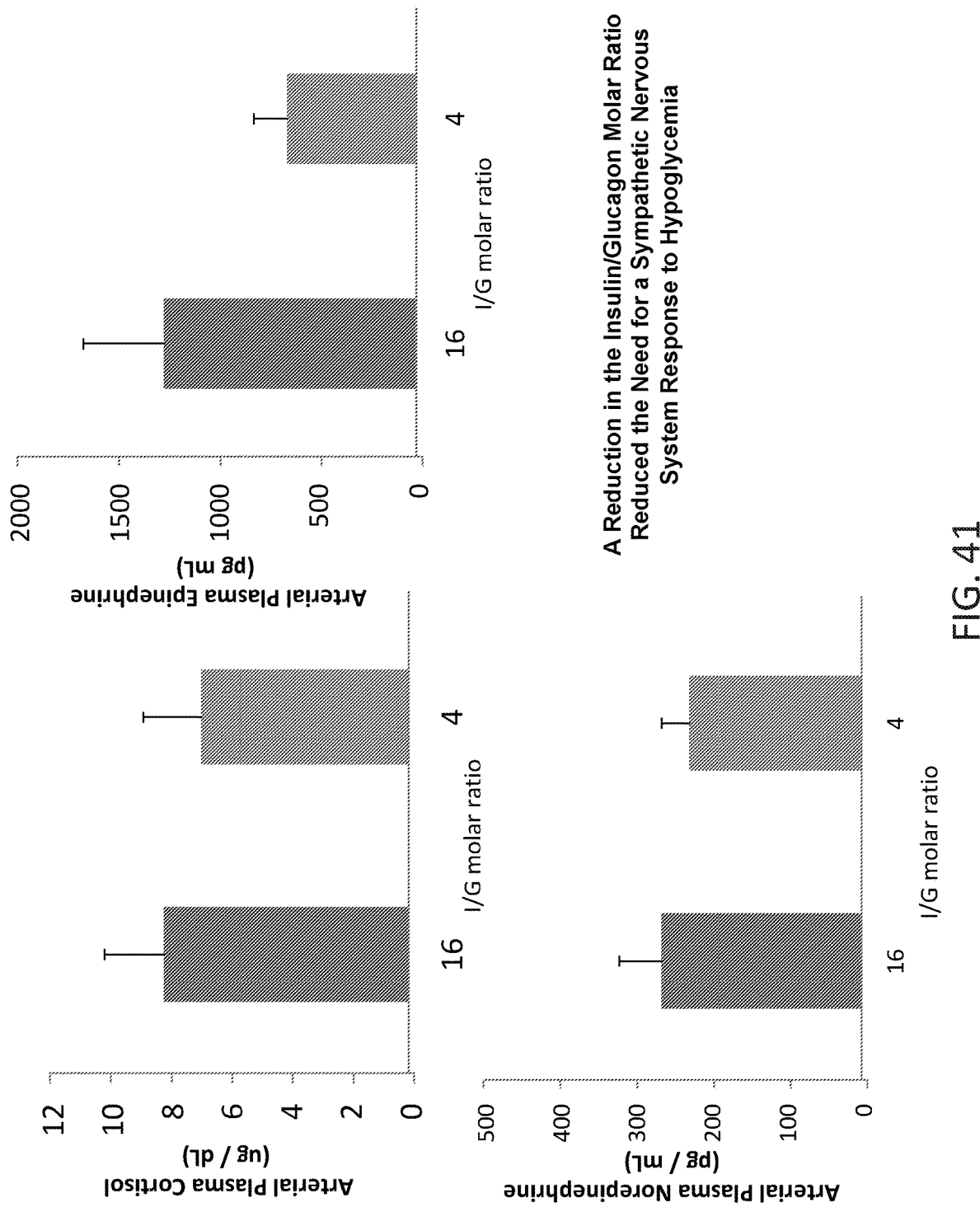

Following the basal clamp period, a 4-fold increase in the insulin infusion rate was brought about, while glucagon was either increased 4-fold or kept basal. Thus, the I/G molar ratio was either 3.8 or 15.0 in subject 7, 4 or 16 in subject 8, 9, 10 and 11A & B and 2.9 and 11.5 in subject 11 C & D (FIGS. 35, 36). Given the subject to subject variation, the data were meaned from four subjects, one of which (subject 15) was studied twice, despite the subtle differences in experimental design. The data from one subject was not included because its blood sugar dropped below 40 mg/dl and required glucose clamping thus preventing the glucose level from being a valid endpoint. Following the baseline period, the insulin infusion rate was increased and plasma insulin rose similarly in both groups to approximately 45 µU/ml (FIG. 37). Clearly the plasma glucagon level rose to almost 150 pg/ml in the group with an I/G ratio of 4, while it did not change in the group with an I/G ratio of 16 (FIG. 38). As a result, plasma glucose fell in both groups but in the presence of an I/G molar ratio of 4, the fall was delayed and diminished (FIG. 39). When adjusted for the baseline difference and plotted on an expanded scale, the fall in plasma glucose was approximately 10 mg/dl less in the group with the lower I/G molar ratio (FIG. 40). As with the IV infusion experiments described herein, the lower I/G molar ratio was associated with reduced epinephrine and cortisol responses to hypoglycemia (FIG. 41; data are meaned values from the last hour of the hypoglycemic period).

Figure 43:
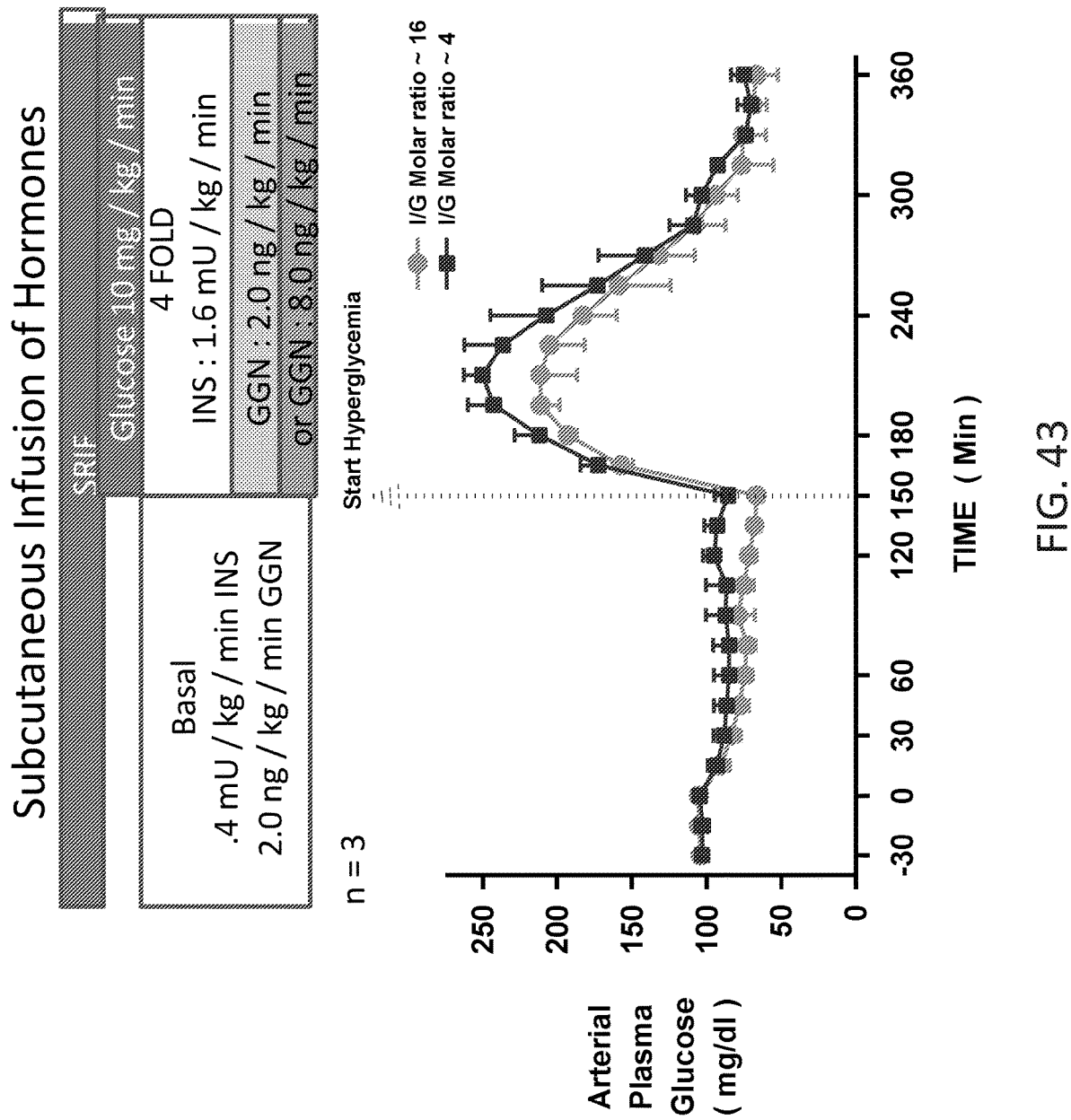
Figure 44:
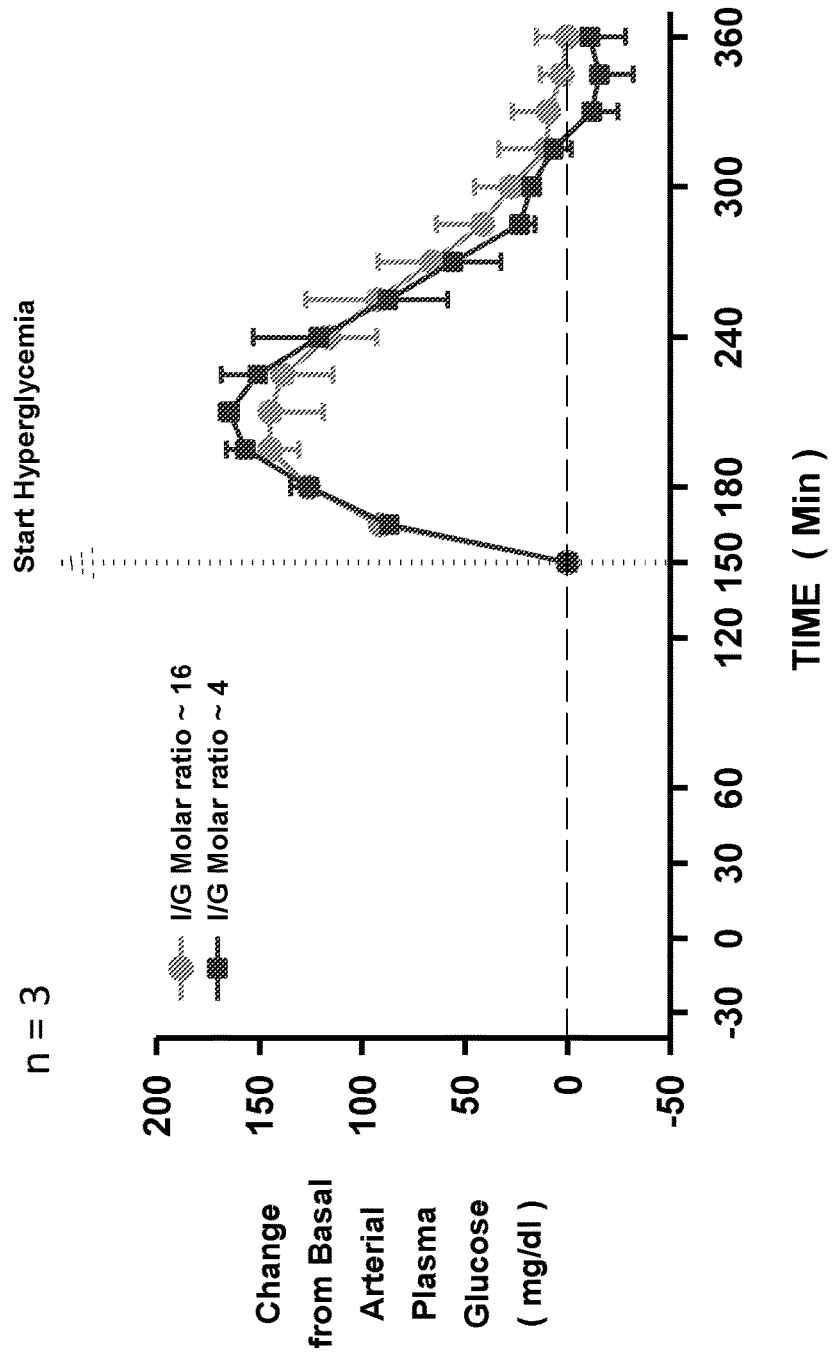
Figure 45:
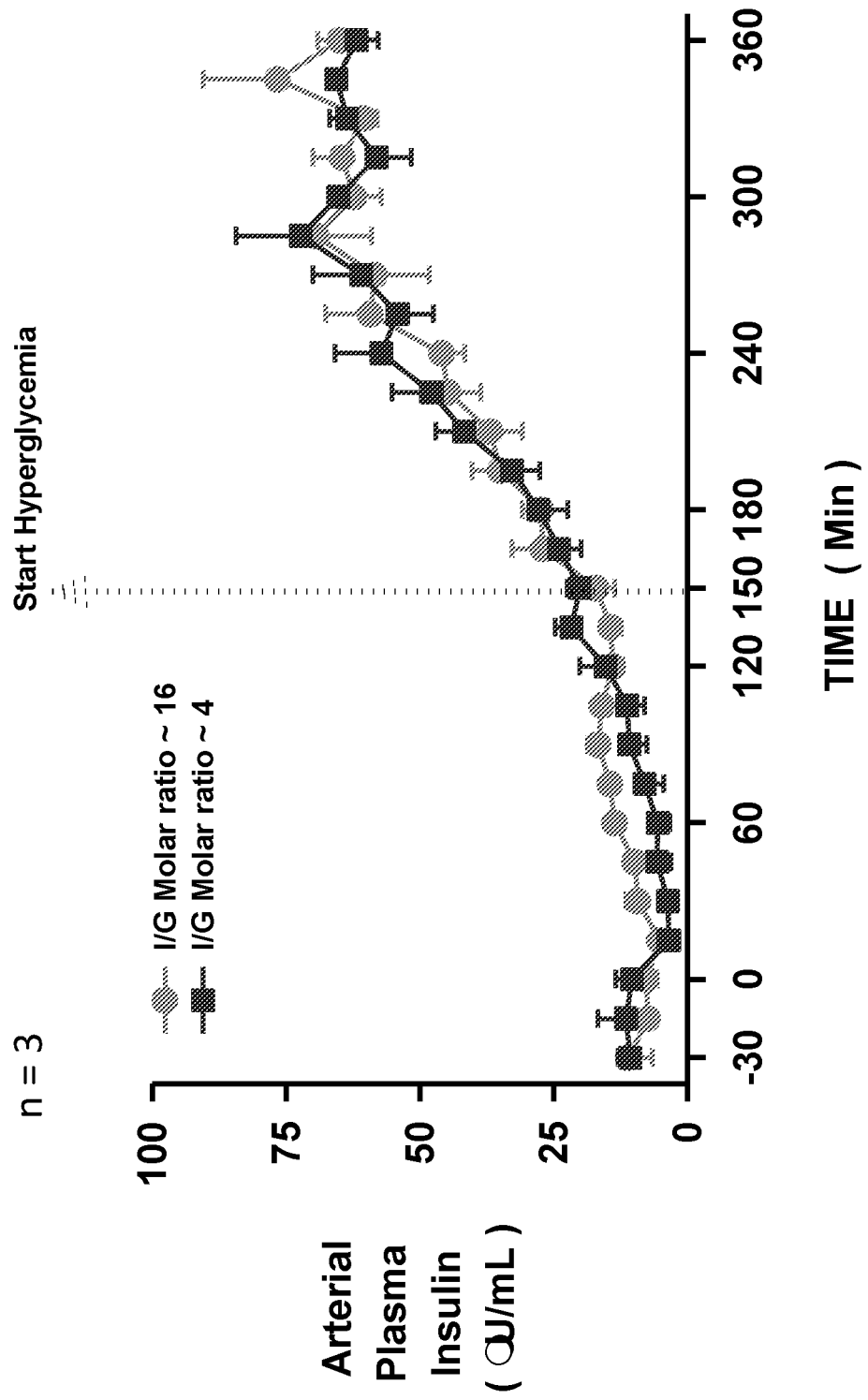
Figure 46:
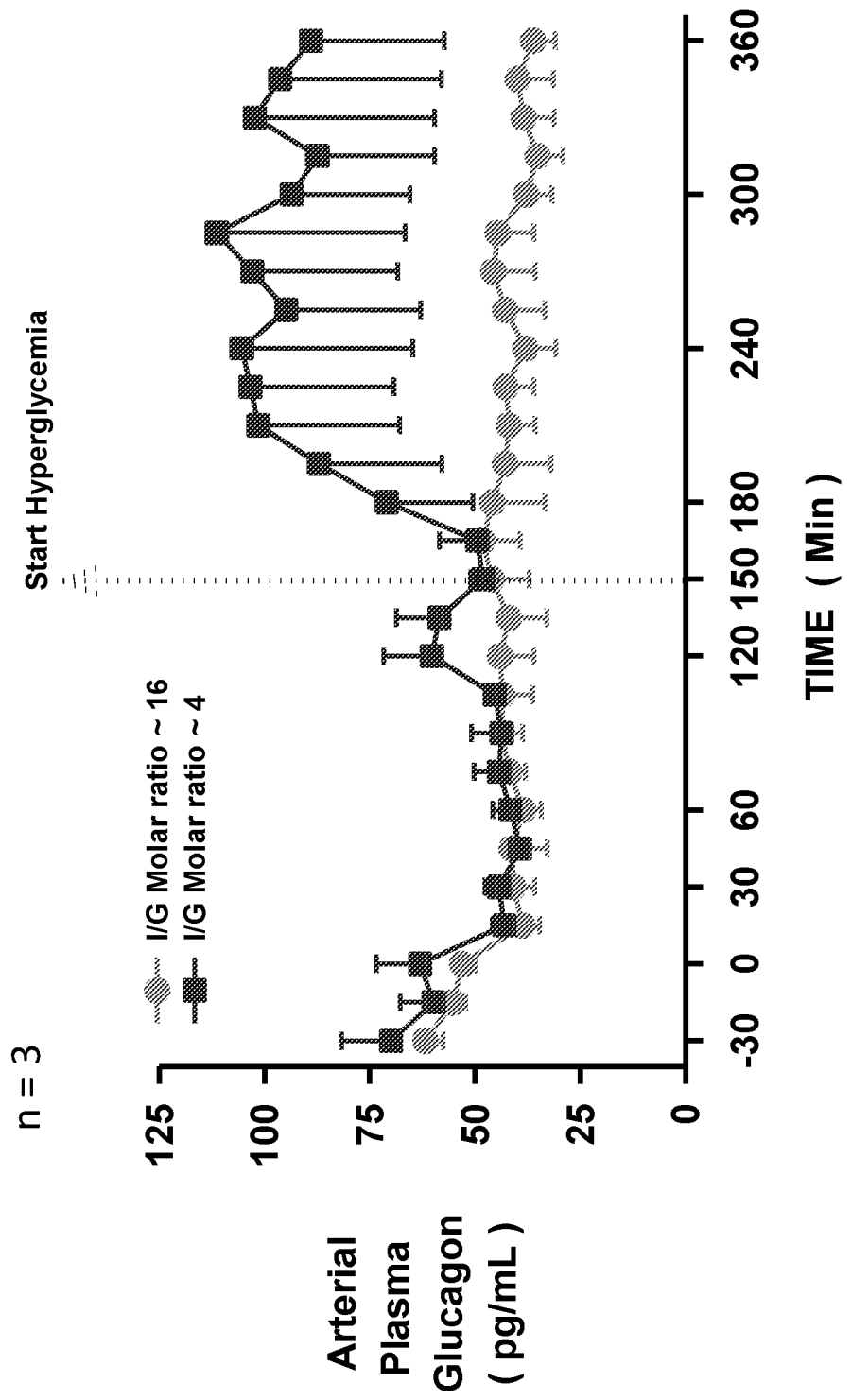

Further studies using subcutaneous hormone infusion examined the impact of maintaining the I/G molar ratio of 4 vs 16 on the ability of the subject to respond to an IV infusion of glucose at 10 mg/kg/min into a leg vein (FIG. 42). Once again, the experiment consisted of a control period (−30 to 0 min), a basal clamp period (0-150 min) and a glucose infusion period (150-360 min). Somatostatin was infused starting at 0 min to disable the endocrine pancreas and insulin and glucagon were infused subcutaneously at rates of 0.4 mU/kg/min and 2 ng/kg/min respectively (I/G molar ratio of 4.1). There was a slight fall in plasma glucose during the basal period (FIG. 43), as was shown in the same period of the subcutaneous hypoglycemic studies. At 150 min, the glucose infusion was started and the insulin infusion rate was quadrupled while the glucagon infusion was either quadrupled or left at basal creating I/G molar ratios of 4.1 or 16.2 respectively. The glucose excursion was slightly higher in the group with an I/G ratio of 4, but this was attributable to a difference in the 150 min baseline value (FIG. 43) such that when the data were plotted as change from baseline (FIG. 44) there was no effect whatsoever of the extra glucagon. As can be seen in FIG. 45 the rise in plasma insulin was identical in the two groups, while glucagon rose in the group with an I/G ratio of 4 but not the group with an I/G ratio of 16 (FIG. 46).

Figure 47:
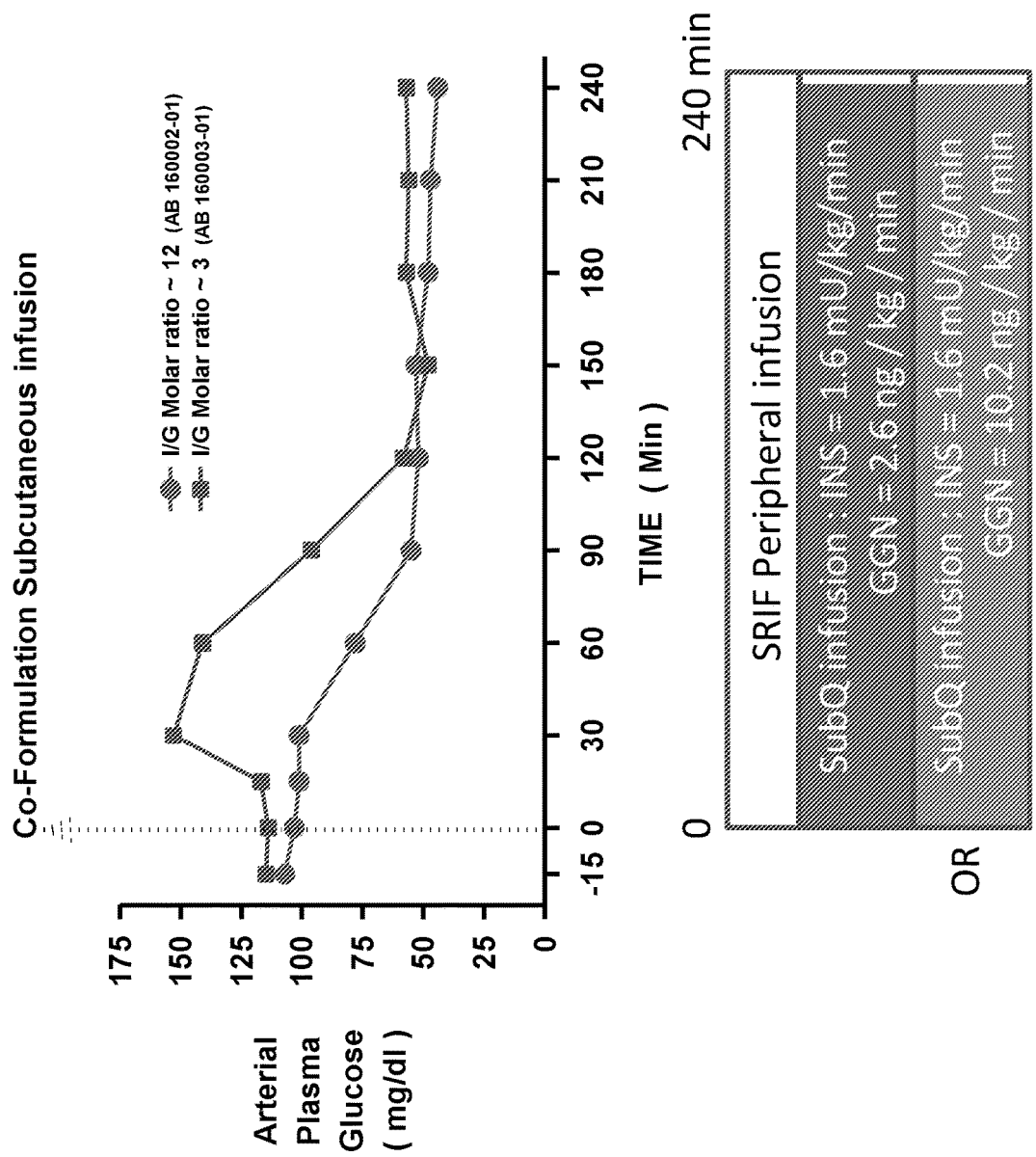
FIGS. 47-48 illustrates data from mammalian studies conducted by applicant in which a co-formulation of insulin and glucagon was used, consistent with the present inventive concepts.
Figure 48:
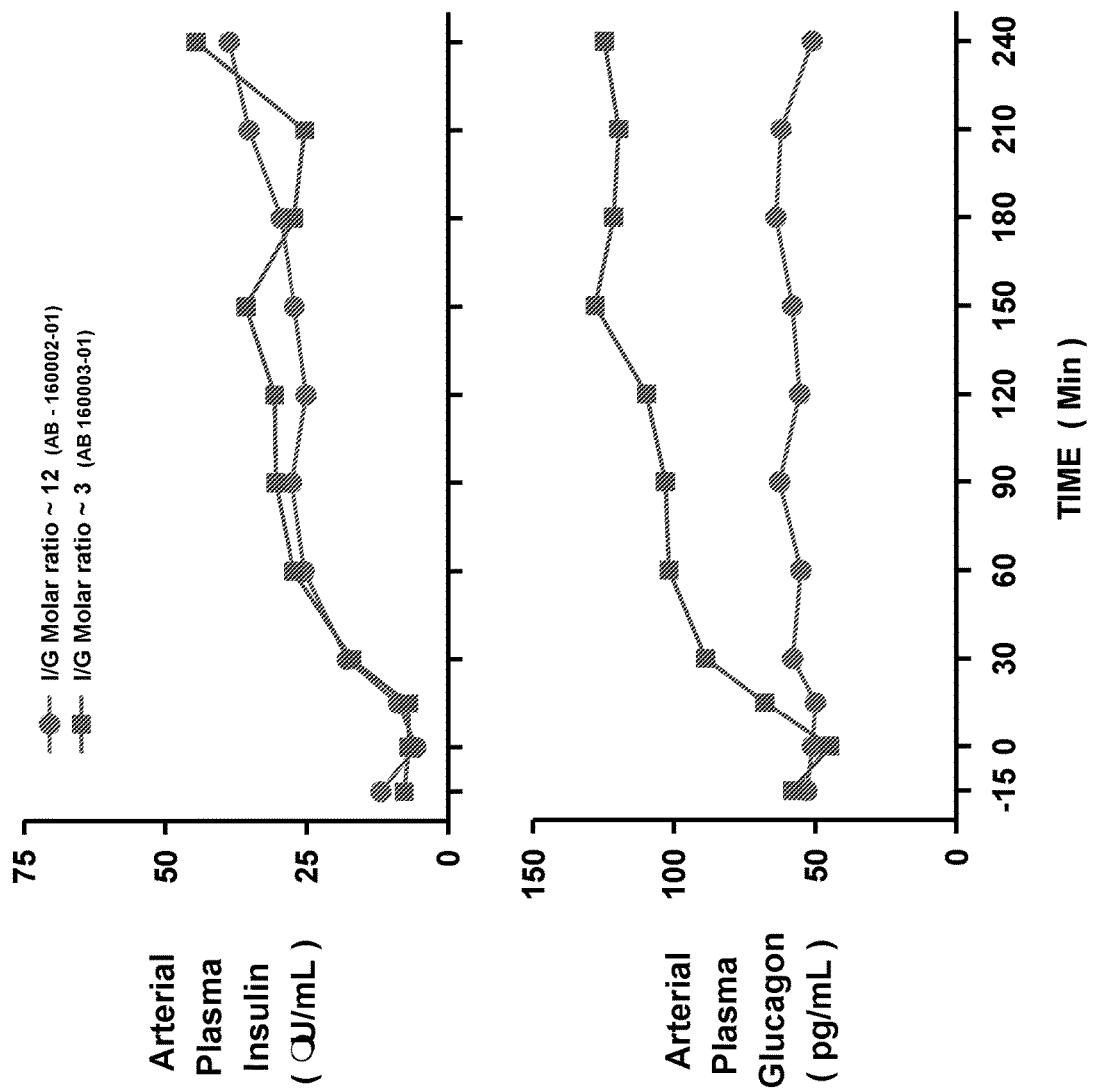

Applicant's further studies include administering a co-formulation of insulin and glucagon subcutaneously. Data from these experiments is illustrated in FIGS. 47-48. In subject 12, two experiments (A and B) were performed. In experiment A, a co-formulated solution of glucagon and insulin in dimethylsulfoxide (DMSO) with an I/G molar ratio of 12 was infused at a rate of ~20 microliters/hr (glucagon 2.6 ng/kg/min and insulin 1.6 mU/kg/min) via a catheter placed in subcutaneous tissue on the day of the study. During the infusion period, plasma glucose drifted down beginning at about 30 mins, eventually plateauing for the last hour at approximately 44 mg/dl (see FIG. 47). The study was then repeated on a second day using another co-formulated glucagon and insulin solution in DMSO with an I/G molar ratio of 3. This co-formulation was also infused at approximately 20 microliters/hr (glucagon 10.2 ng/kg/min and insulin 1.6 mU/kg/min). In this case, there was an initial rise in glucose followed by a fall to a minimum value at 150 mins, similar to that seen in experiment A. Then, however, plasma glucose level increased plateauing at ~56 mg/dl (see FIG. 47). Thus, as occurred with independent subcutaneous infusion of insulin and glucagon, the extent of hypoglycemia caused by the rise in insulin was markedly reduced by the concomitant elevation of glucagon. The insulin levels in plasma were similar in the two experiments (35 vs 31 µU/ml during the last hour) while glucagon remained low (60 pg/ml) in experiment A and rose to 121 pg/ml in experiment B (see FIG. 48). These data established two important principles. First, it is clearly possible to co-formulate insulin and glucagon in a solvent that is mutually compatible so that these peptide hormones can be co-administered in one solution. Second, the biologic response to the two hormones is similar whether they are infused subcutaneously independently or as a co-formulated mixture. In both cases, quadrupling an insulin infusion with a concomitant and proportional rise in glucagon (I/G molar ratio of 3) reduced the insulin induced hypoglycemia by ~10-12 mg/dl. It is very likely that this effect will be associated with a significantly reduced activation of the autonomic nervous system.

Taken together, the studies described herein established an efficacious I/G molar ratio for use for subcutaneous insulin and glucagon delivery, in one or more forms. These studies also confirm the IV infusion data indicating that maintaining a low I/G molar ratio while raising insulin protects against hypoglycemia without significantly interfering with the ability of insulin to deal with hyperglycemia.

Referring now to FIGS. 49-60, results from studies conducted by applicant are presented, consistent with the present inventive concepts. In these studies, the ability of glucagon to increase and sustain increased glucose production when presented with insulin-induced hypoglycemia was assessed. Results of these studies indicate that glucagon can produce a significant and sustained production of glucose when presented with insulin-induced hypoglycemia. As described herebelow, the data indicates glucagon has a biphasic rather than a time-dependent effect on the liver. Glucagon produces a rapid burst of glucose, followed by a prolonged second phase of glucose production, indicating that in the presence of insulin-induced hypoglycemia, glucagon continues to function for a prolonged period (e.g. at least 4 hours). These studies have shown that the body is aware of the increased levels of glucagon, and in response, reduces its sympathetic nervous system response to hypoglycemia. A reduction in sympathetic nervous system response to hypoglycemia suggests that the brain can sense plasma glucagon, and that there is a reciprocal relationship between glucagon and sympathetic nervous systems in controlling blood sugar levels. The brain monitors the glucagon level and, in the presence of excess glucagon, decreases the sympathetic nervous system's response to a given hypoglycemia. This would allow for a further decline in glucose to trigger a more substantial increase in the central nervous system response, thereby providing greater protection against hypoglycemia. The studies demonstrate that a co-formulated insulin and glucagon solution of the present inventive concept could provide safe and effective therapeutic value to a diabetic patient.

Applicant has conducted a study on each of eight conscious subjects (canine), in support of the therapeutic value of a co-formulated insulin and glucagon solution of the present inventive concepts. The eight subjects were broken into two groups of four subjects, the first group denoted as the basal glucagon group (Ba GGN) and the second group denoted as the high glucagon group (Hi GGN). Results of this study are shown in FIGS. 49-60.

Each canine subject was adrenalectomized and treated with gluco and mineralo corticoids, to maintain basal levels of these hormones in the blood, such that a hypoglycemia-induced glucose production response could be attributed to glucagon and not epinephrine. Catheters were placed in the blood vessels supplying blood to (e.g. artery, hepatic portal vein), and draining blood (e.g. hepatic vein) from the liver. Blood flow probes were placed around the hepatic artery and portal vein to allow for use of an arteriovenous difference (AV) method to calculate net hepatic glucose output (HGO). Additionally, tracer methods (e.g. 3-3H glucose) were used to assess hepatic glucose production (HGP). Following recovery from surgery and after an overnight fast, experiments were conducted on each subject in a conscious state.

Figure 49:
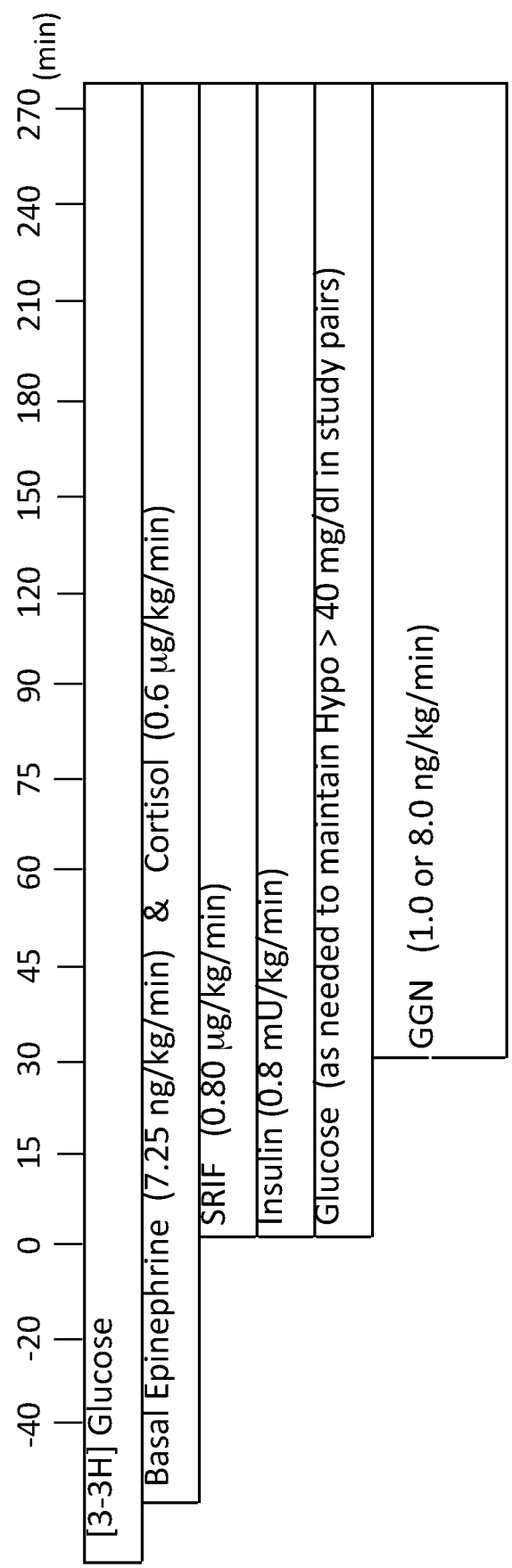
FIG. 49 illustrates an experimental timeline of a mammalian study conducted by applicant to assess the ability of glucagon to increase and sustain increase glucose production when presented with insulin-induced hypoglycemia, consistent with the preset inventive concepts.

FIG. 49 illustrates the experimental timeline employed for each of the eight subjects. The tracer infusion commenced at −140 min and 100 min was allowed for equilibration. A control period from −40 min to 0 min was followed by a 270 min test period. At 0 min, somatostatin (SRIF) was infused to disable the endocrine pancreas. Insulin was infused into a leg vein at 0.8 mU/kg/min to create hypoglycemia. Beginning at 30 min, glucagon was also infused into a leg vein at 1 or 8 ng/kg/min (e.g. 1 ng/kg/min for a Ba GGN subject, and 8 ng/kg/min for a Hi GGN subject). Glucose was infused as required to match the rate of glucose fall in the two groups and to ensure the plasma glucose level did not drop below 40 mg/dL in either group.

Figure 50:
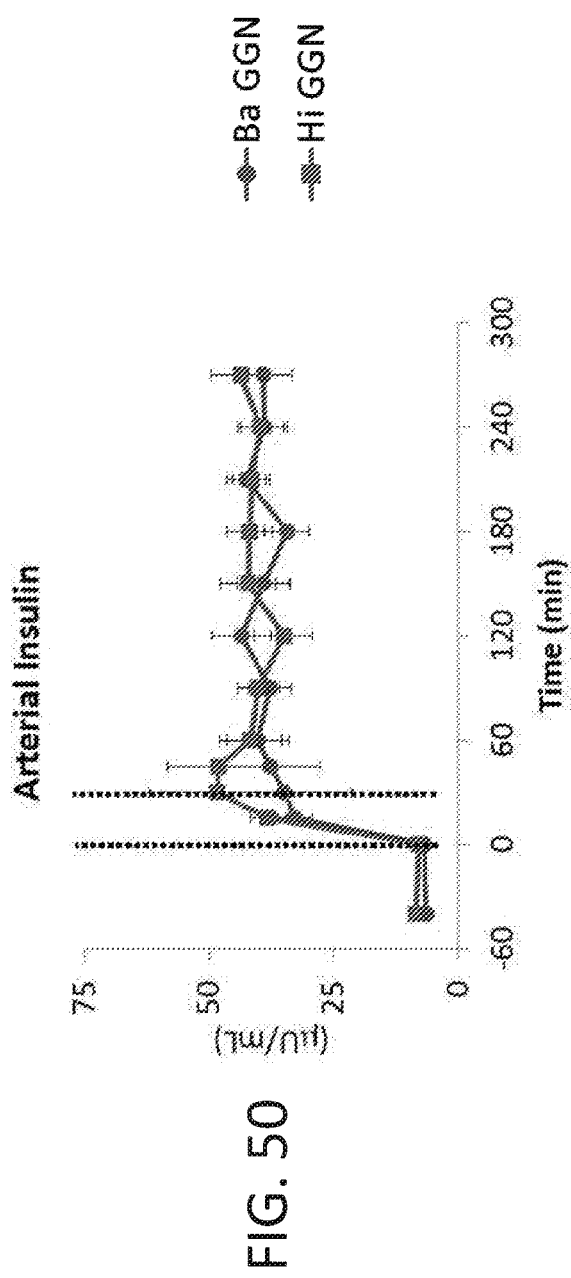
FIGS. 50-60 illustrate data from mammalian studies conducted by applicant to assess the ability of glucagon to increase and sustain increase glucose production when presented with insulin-induced hypoglycemia, consistent with the preset inventive concepts, consistent with the present inventive concepts.

FIG. 50 illustrates data that shows the arterial insulin level increased from ~10 μU/mL to ~40 μU/mL in both groups.

Figure 51:
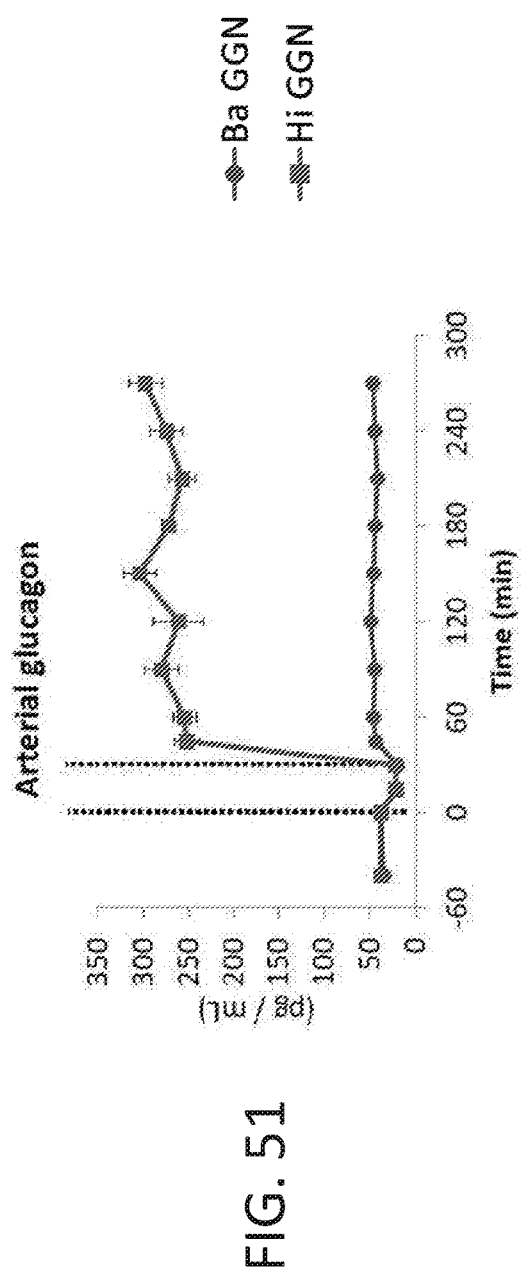

FIG. 51 illustrates data that shows the arterial glucagon level remained basal (e.g. ~45 pg/mL) in the Ba GGN group but increased to ~270 pg/mL in the Hi GGN group.

Figure 52:
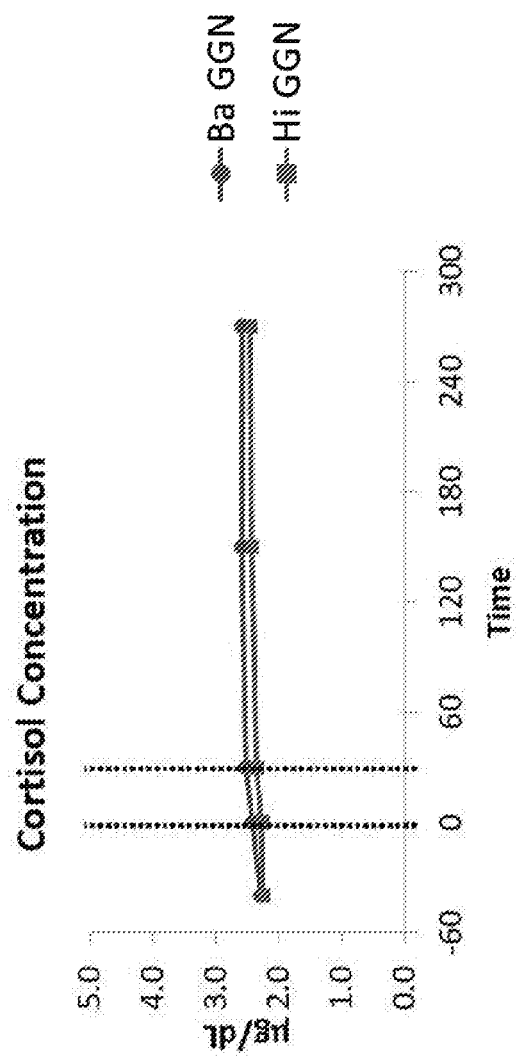

FIG. 52 illustrates data that shows cortisol concentrations remained basal (e.g. 2.5 μg/dL) in both groups, as attributed to the adrenalectomy and basal hormone replacement.

Figure 53:
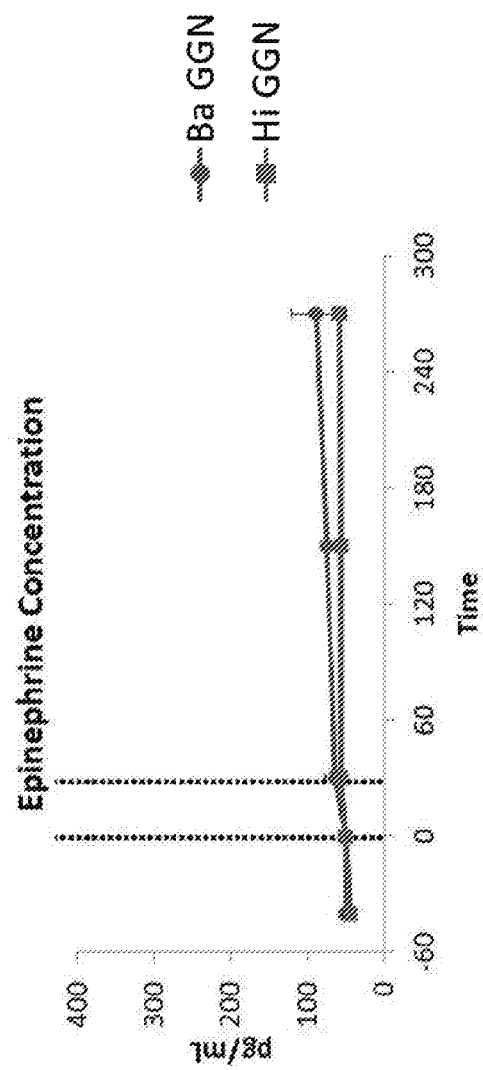

FIG. 53 illustrates data that shows epinephrine concentrations remained basal (e.g. 50-75 pg/mL) in both groups, as attributed to the adrenalectomy and basal hormone replacement.

Figure 54:
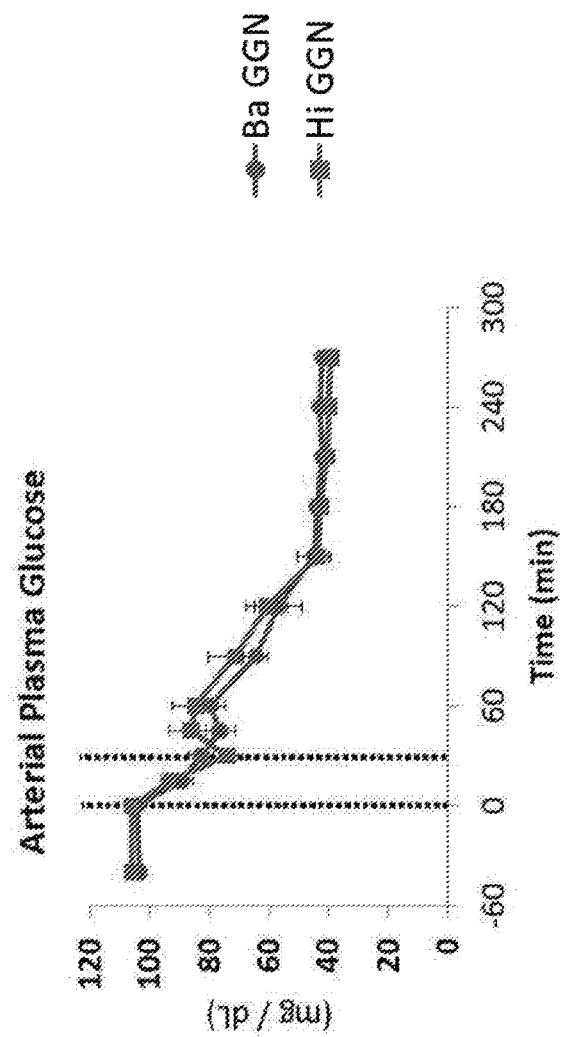

FIG. 54 illustrates data that shows, for both groups, arterial plasma glucose decreased equivalently and plateaued at a similar level for the last 2.5 hours of the experiment (e.g. 42 mg/dL in the Ba GGN group and 40 mg/dL in the Hi GGN group).

Figure 55:
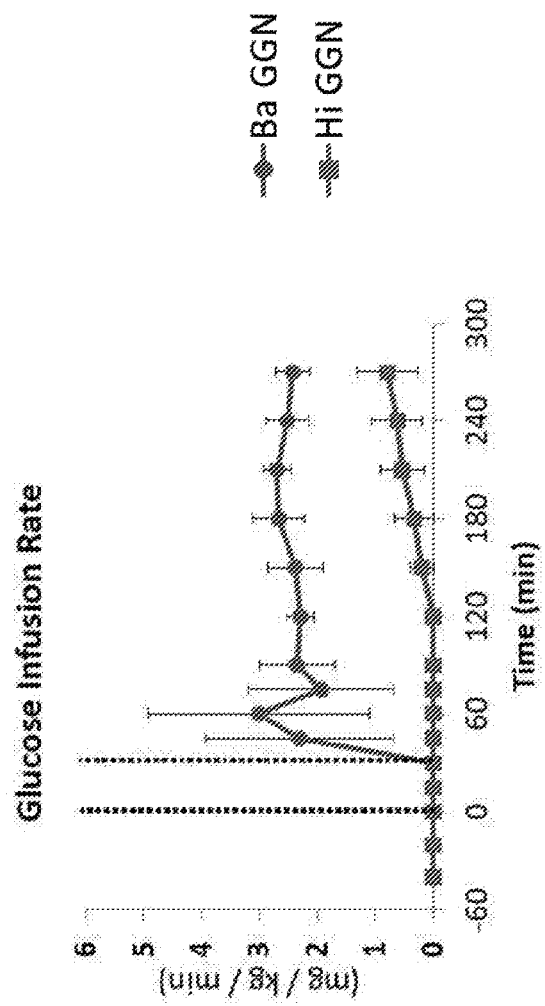

FIG. 55 illustrates data that shows the glucose infusion rate required to match the glucose curves for each group. For the Ba GGN group, glucose was infused beginning at 30 min (e.g. coincident with the glucagon infusion) and was continued throughout the experiment averaging about 2.8 mg/kg/min during the last 2.5 hours. For the Hi GGN group, glucose was infused beginning at 2 hours and the infusion rate was slowly increased to about 0.8 mg/kg/min.

Figure 56:
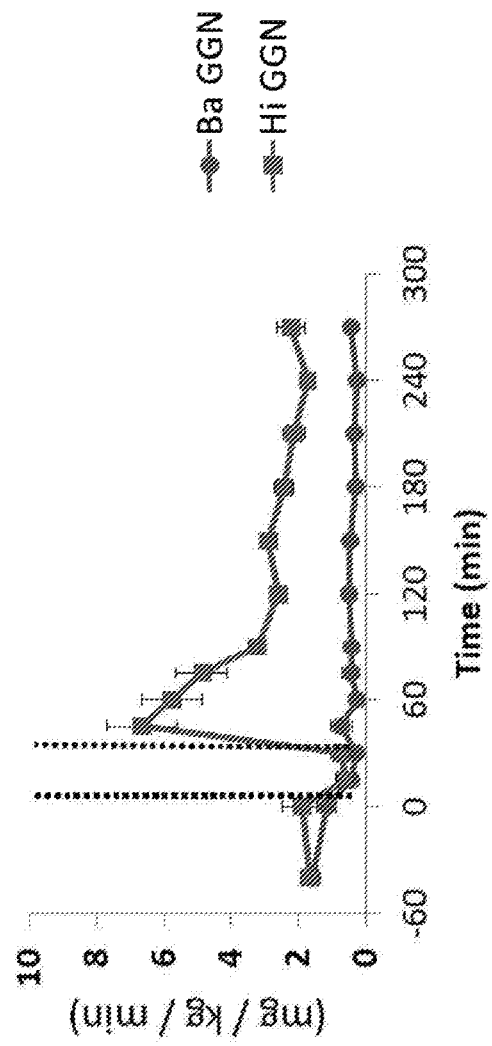

FIG. 56 illustrates data that shows the net hepatic glucose output. For both groups, the net hepatic glucose output decreased over 0 to 30 min as a consequence of the increase in insulin and the decrease in glucagon. Following the infusion of glucagon at 30 min, the Ba GGN group net hepatic glucose output was maintained at about ~0.4 mg/kg/min. Following the infusion of glucagon at 30 min, the Hi GGN group net hepatic glucose output increased rapidly to about 7 mg/kg/min, and thereafter decreased, over a time period of about 90 min, eventually reaching a rate averaging 2.4 mg/kg/min for the last 2.5 hours of the experiment. Such data indicates that in the presence of hypoglycemia, the increase in glucagon sustains an increase in glucose production of about 2-2.5 mg/kg/min despite the continued presence of elevated insulin.

Figure 57:
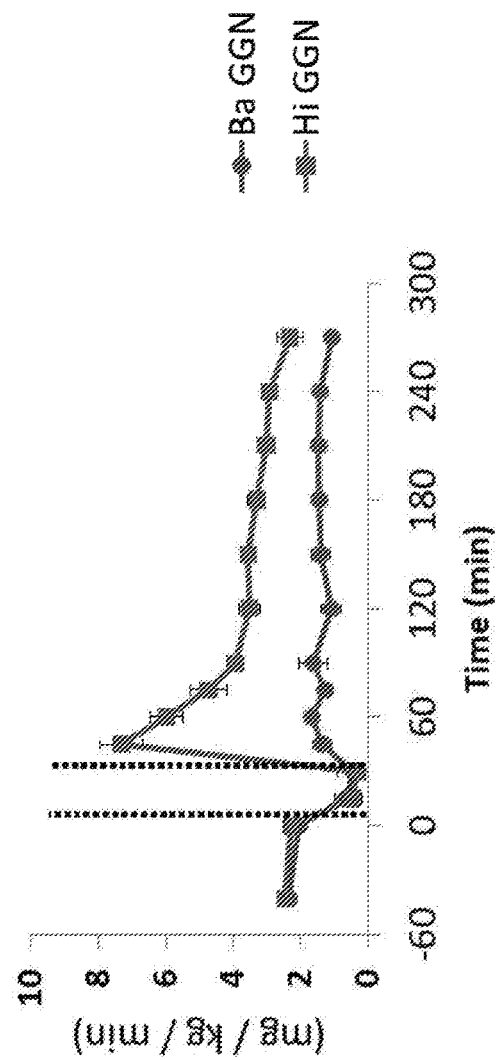

FIG. 57 illustrates the 3-3H glucose tracer determined glucose production data and confirms the net hepatic glucose balance data as described hereabove in reference FIG. 56.

Figure 58A:
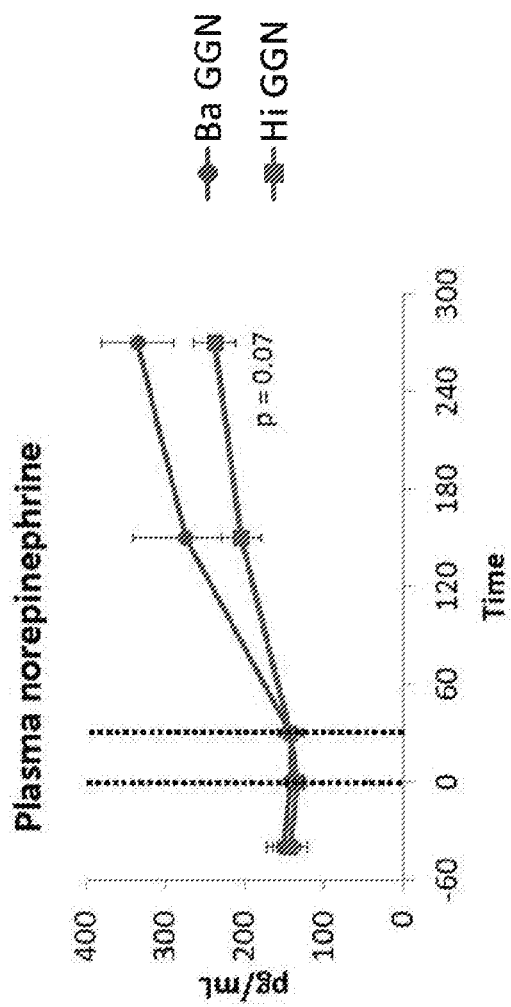
Figure 58B:
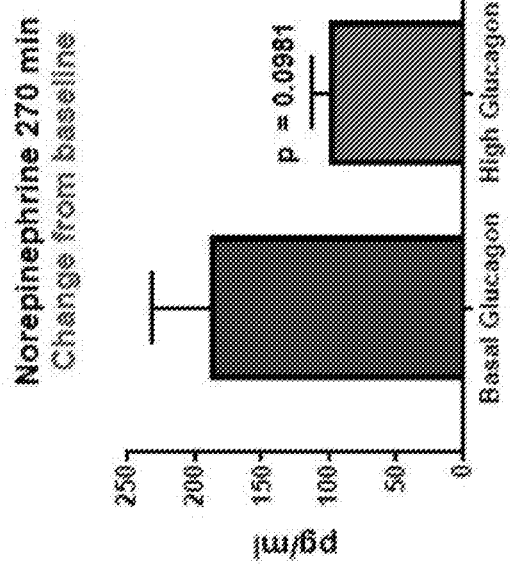

FIG. 58A illustrates data that shows, in both groups, hypoglycemia caused an increase in plasma norepinephrine. This data reflects the spillover of norepinephrine from nerve endings throughout the body (e.g. sympathetic nervous system tone) and reflects the signal that stimulates lipolysis during insulin-induced hypoglycemia. FIG. 58B illustrates data that shows the increase in plasma norepinephrine in the Ba GGN group was twice as large as the increase in the Hi GGN group.

Figure 59A:
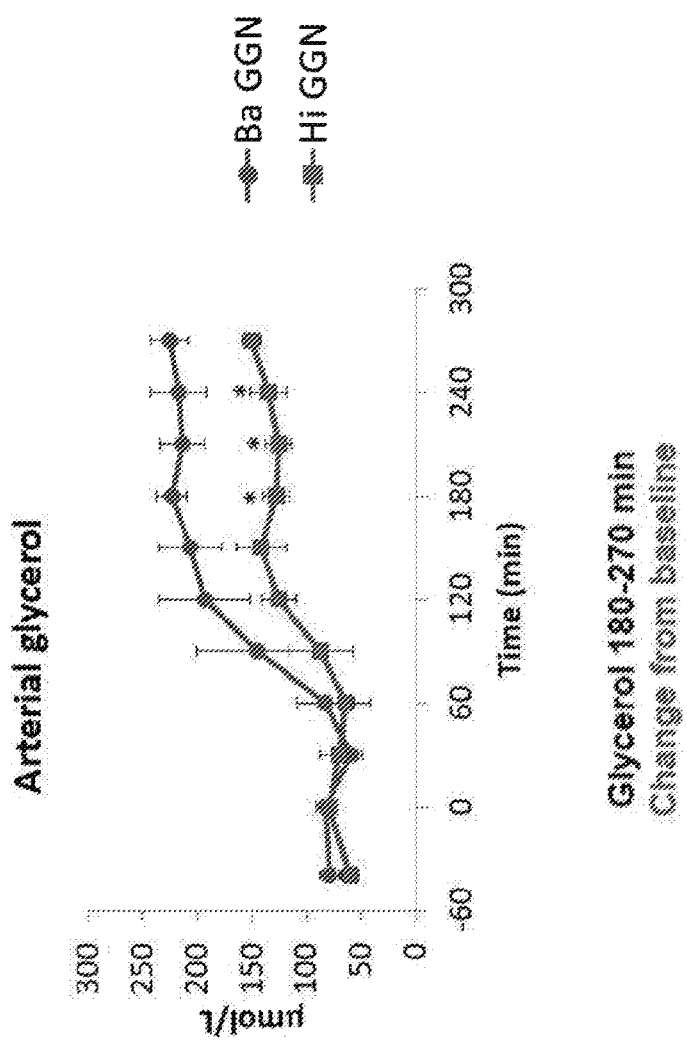
Figure 59B:
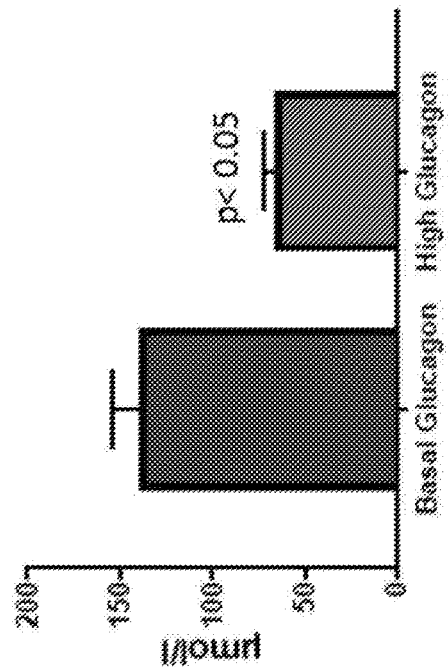

FIGS. 59A and B illustrate data that show that in Hi GGN group, hypoglycemia caused a decreased lipolytic response, as assessed using arterial glycerol levels, relative to that in the Ba GGN group. The lipolytic response to hypoglycemia was decreased by ~60% in the presence of high glucagon.

Figure 60:
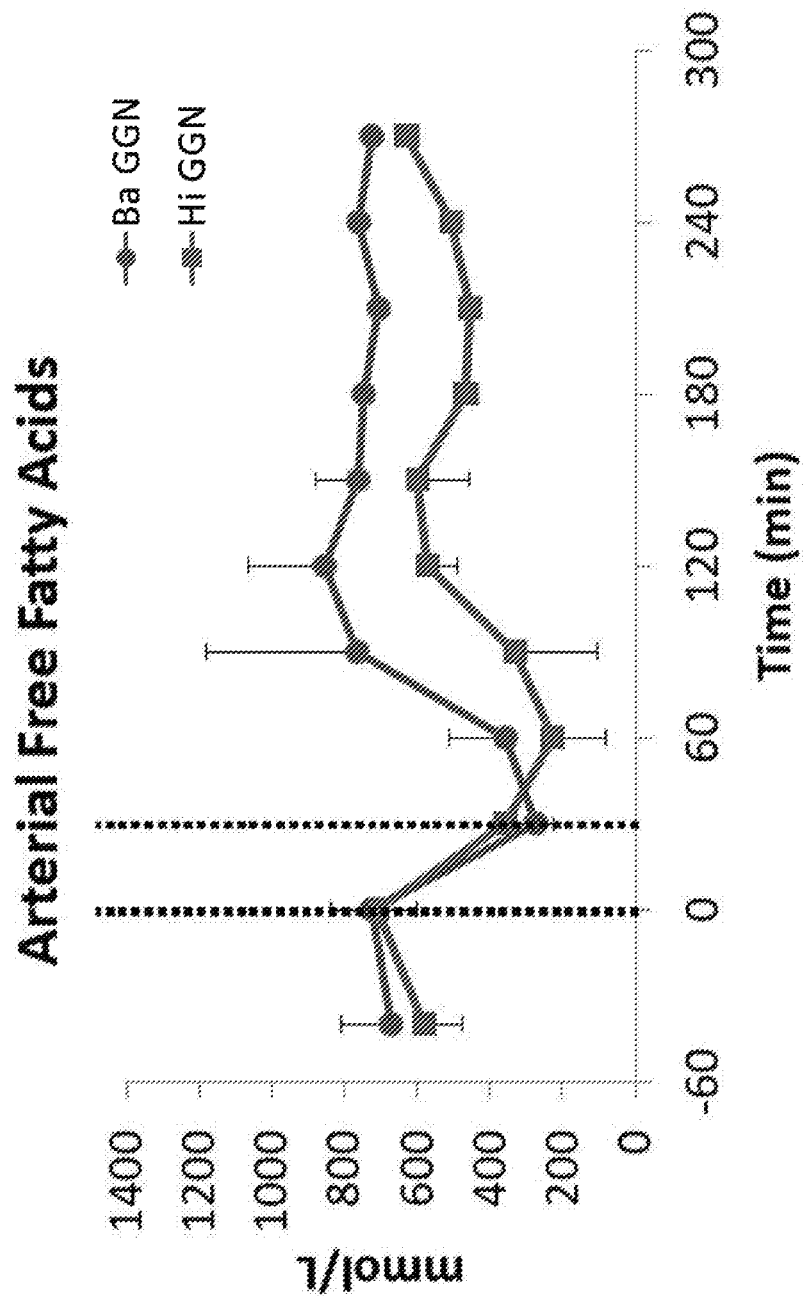

FIG. 60 illustrates data that shows that in the Hi GGN group, hypoglycemia caused a decreased lipolytic response relative to the Ba GGN group, as assessed using arterial free fatty acids levels.

Figure 61:
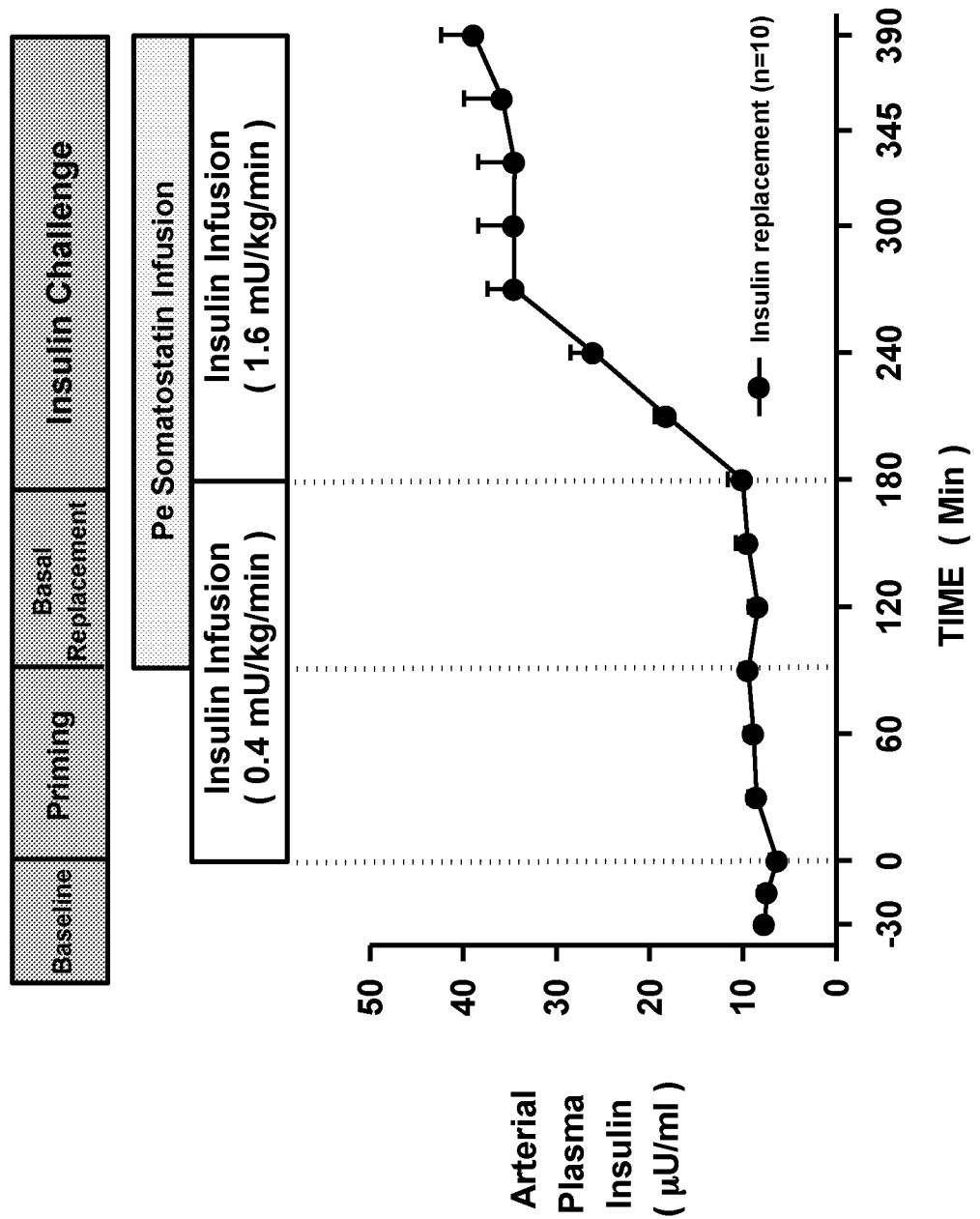
FIGS. 61 and 62 illustrate data from mammalian studies conducted by applicant to assess the potential of a co-formulation of insulin and glucagon to allow for basal hormone replacement and to provide significant hypoglycemia protection, consistent with the present inventive concepts.
Figure 62:
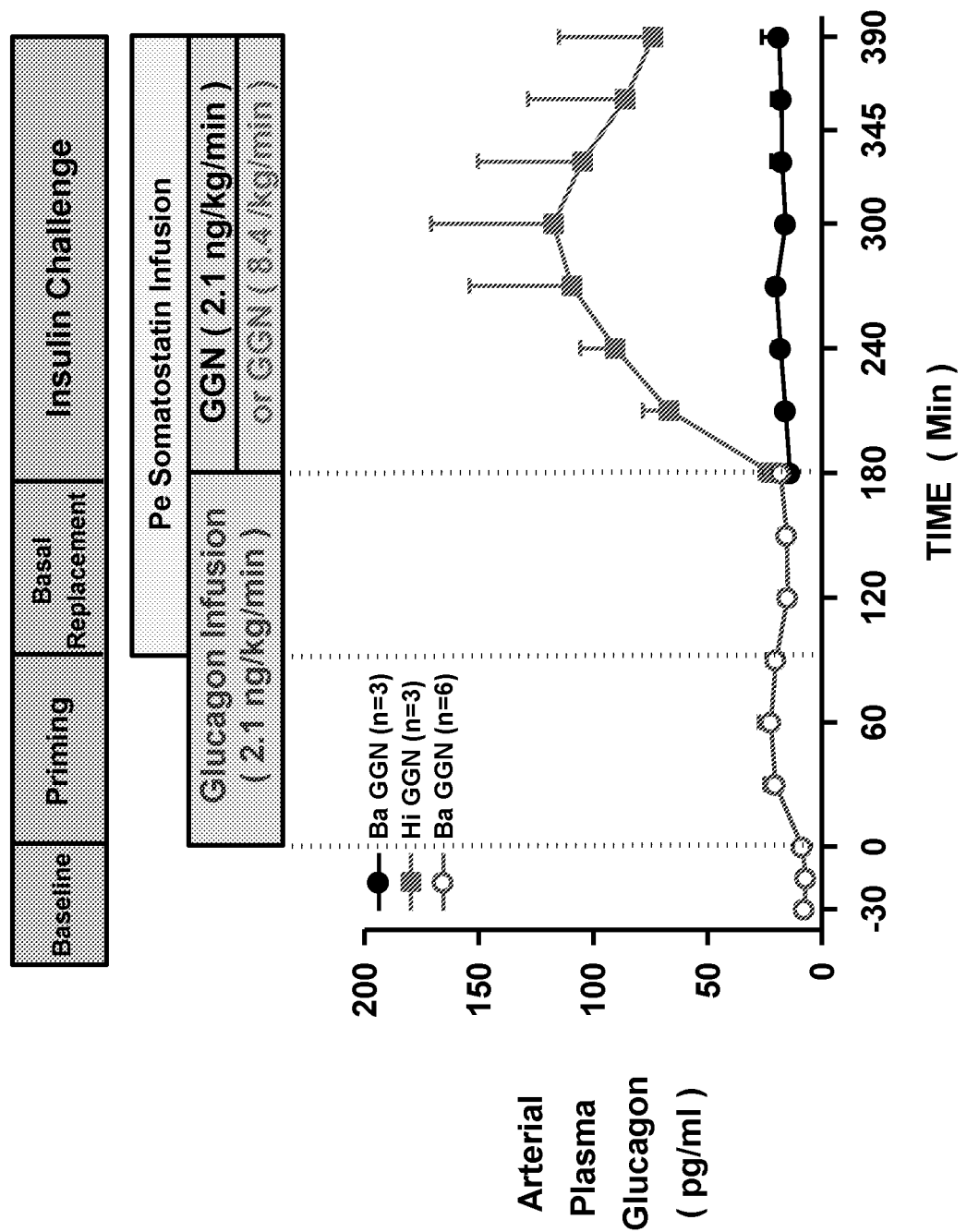

Referring now to FIGS. 61 and 62, results from studies conducted by applicant are presented, consistent with the present inventive concepts. In these studies, the potential of a co-formulation of insulin and glucagon of the present inventive concepts was assessed, the co-formulation was configured to allow basal hormone replacement and provide significant hypoglycemia protection. Results of these studies show an optimized insulin to glucagon (I/G) molar ratio to be greater than 1 but less than 10. As described herebelow, subcutaneous co-infusion of insulin at a rate of 0.4 mU/kg/min (±20%) and glucagon at a rate of 2.1 ng/kg/min (±20%), with an I/G molar ratio of 4, can replace basal secretion of the two hormones with minimal deviation of the plasma glucose level. The results of these studies also show there is a significant reduction in insulin-induced hypoglycemia and an evident reduction in central nervous system activation when the I/G molar ratio is maintained as insulin is increased 4-fold. These studies were conducted on conscious canine subjects to further examine the efficacy of co-formulated insulin and glucagon solutions with varying I/G molar ratios.

Preliminary experiments were conducted to better understand the pharmacokinetic (PK) and pharmacodynamic (PD) properties of subcutaneously infused insulin. FIG. 61 illustrates data that relates to subcutaneous insulin infusion in conscious canine subjects, consistent with the present inventive concepts. As described herebelow, increasing the insulin infusion rate 4-fold has been shown to increase the arterial insulin level ~4-fold with a lag time of ~90 min. In overnight fasted canines, baseline arterial plasma insulin was 7.1±0.7 μM/mL at −30 min to 0 min. Following 90 min of subcutaneous infusion of insulin at 0.4 mU/kg/min, arterial plasma insulin increased to 9.4±0.8 μU/mL; reflecting both the endogenously released and infused insulin. At 90 min, a somatostatin infusion was commenced to disable the endocrine pancreas. Endogenous insulin secretion quickly ceased (as indicated by a decrease in C-peptide), such that the insulin attributed to endogenous insulin secretion was depleted within 30 min. During the last 30 min of the basal hormone replacement period (e.g. from 150 to 180 min), the arterial insulin averaged 9.8±1.4 μU/mL and was solely attributable to the subcutaneous infusion. Thus, arterial insulin increased from the baseline by approximately 40% when insulin was delivered subcutaneously at 0.4 mU/kg/min. This increase is similar to the increase in arterial insulin required to maintain euglycemia when endogenous insulin secretion is replaced by peripheral intravenous insulin delivery. It can be estimated that the insulin level within the liver was ~17 μU/mL at baseline (from −30 min to 0 min due to endogenous insulin release into the portal vein) and 7.8 μU/mL during the basal hormone replacement period (e.g. when endogenous secretion was inhibited) a decrease of almost 50%. Therefore, with a subcutaneous insulin infusion rate of 0.4 mU/kg/min, the clinical situation typically seen with subcutaneous insulin administration in humans with Type 1 Diabetes Mellitus lacking beta cell function was replicated. Increasing the insulin infusion rate 4-fold during the insulin challenge period caused the arterial insulin level to increase to 34.5±2.9 μU/mL within 90 min, after which it increased minimally, ultimately reaching 38.8±3.5 μU/mL. Based on these data, it was determined that ~90 min of subcutaneous insulin infusion (20 μL/h) is required to "prime" the system (i.e. infusion of insulin in the absence of somatostatin infusion). A subcutaneous insulin infusion at a rate of 0.4 mU/kg/min provides basal insulin replacement and a 4-fold increase in the insulin infusion rate, increasing the arterial insulin 4-fold.

FIG. 62 illustrates data that relates to subcutaneous glucagon infusion in conscious canine subjects. As described herebelow, increasing the glucagon infusion rate 4-fold (referred to as the Hi GGN group) increased the arterial glucagon level over 1 to 2 hours, after which it decreased. It should be noted that the Mercodia assay was used to measure glucagon in these experiments due to its improved accuracy thus the plasma glucagon levels are lower than in earlier studies. The peak fold rise in the arterial glucagon levels in three canine subjects were 3.7, 5.7, and 6.8 ($\bar{x}$=5.4), respectively. In overnight fasted canines (as indicated by the blue dots and referred to as Ba GGN), baseline arterial plasma glucagon was 7.5±1.2 pg/mL at −30 min to 0 min, giving rise to a predicted level of ~15 pg/mL at the liver (e.g. as a result of endogenous glucagon secretion into the portal vein). Coincident with the commencement of the SQ insulin infusion at 0 min, as shown in FIG. 61, glucagon was also subcutaneously infused at a rate of 2.1 ng/kg/min. Following 90 min of subcutaneous infusion of glucagon, arterial plasma glucagon had increased to an average of 21.5±4.0 pg/mL; reflecting both endogenously released and infused glucagon. Within 30 min of the commencement of the somatostatin infusion (e.g. to inhibit endogenous glucagon secretion) the arterial glucagon level decreased to ~15.0±4.5 pg/mL, representing a level close to twice the baseline glucagon value. Therefore, the level of glucagon within the liver sinusoids from infusing at a rate of 2.1 ng/kg/min can be estimated to be close to its baseline value. During the insulin challenge period, in which the basal glucagon infusion rate remained at 2.1 ng/kg/min, the arterial glucagon level was maintained for 3.5 hours.

Referring now to FIGS. 63-65, results from studies conducted by applicant are presented, consistent with the present inventive concepts. In these studies, the ability of a co-infusion of insulin and glucagon of the present inventive concepts, at optimal replacement rates, was assessed, the co-infusion was configured to replace basal endogenous secretion of the two hormones while still maintaining euglycemia.

FIGS. 63A and B illustrate data that relate to hormone concentrations during co-infusion of insulin and glucagon of the present inventive concepts. Insulin was infused at a rate of 0.4 mU/kg/min and glucagon was infused at a rate of 2.1 ng/kg/min. During the priming and basal replacements periods from 0-180 min, the I/G molar ratio was 4. At the commencement of the insulin challenge period at 180 min, insulin infusion was increased 4-fold to 1.6 mU/kg/min, while glucagon was either increased 4-fold to 8.4 ng/kg/min (an I/G molar ratio of 4, referred to as the Hi GGN group) or kept basal at 2.1 ng/kg/min (an I/G molar ratio of 16, referred to as the Ba GGN group). As shown in FIG. 63A, the arterial insulin levels in both groups were very similar and increased ~4-fold during the insulin challenge period. As shown in FIG. 63B, the arterial glucagon levels remained basal in the Ba GGN group and increased over 5-fold in the Hi GGN group during the insulin challenge period.

Figure 64A:
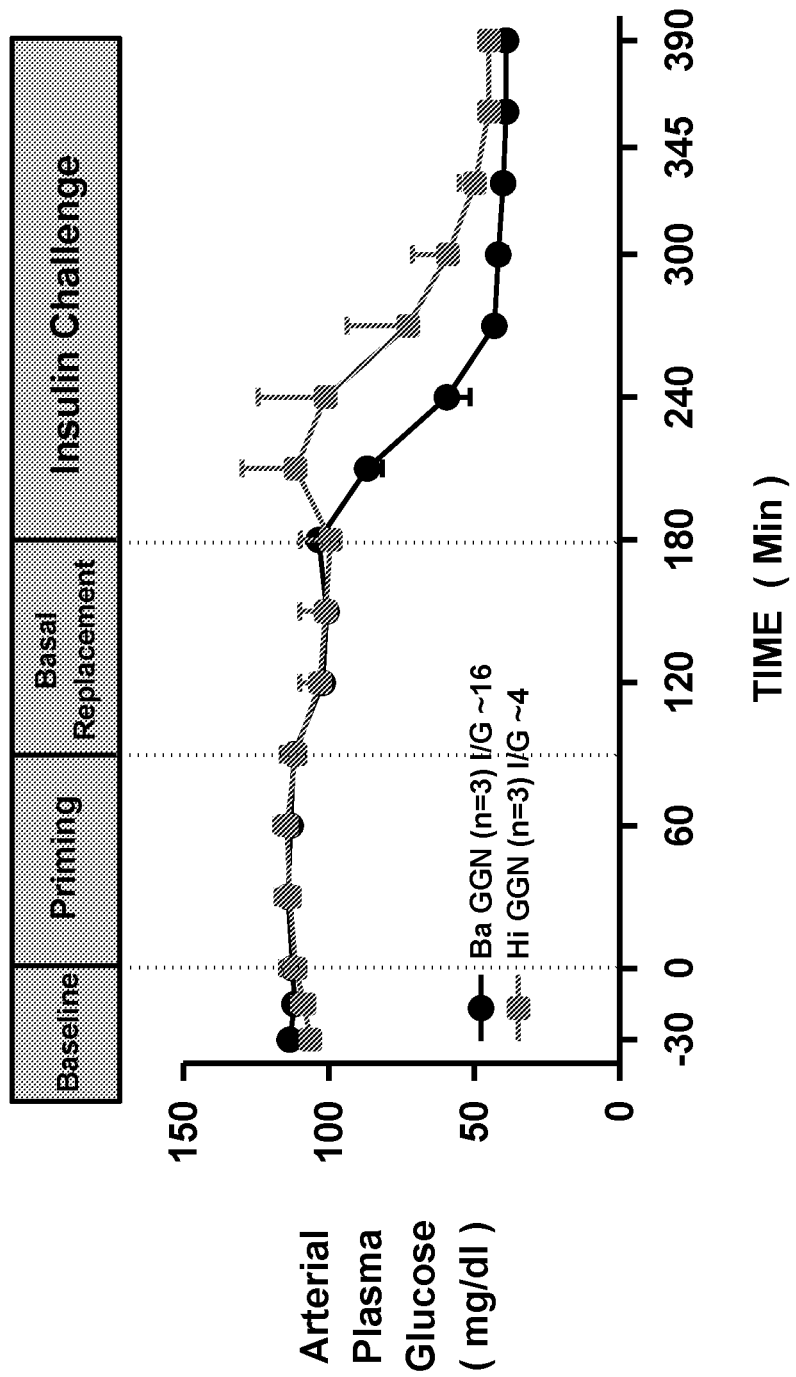
Figure 65A:
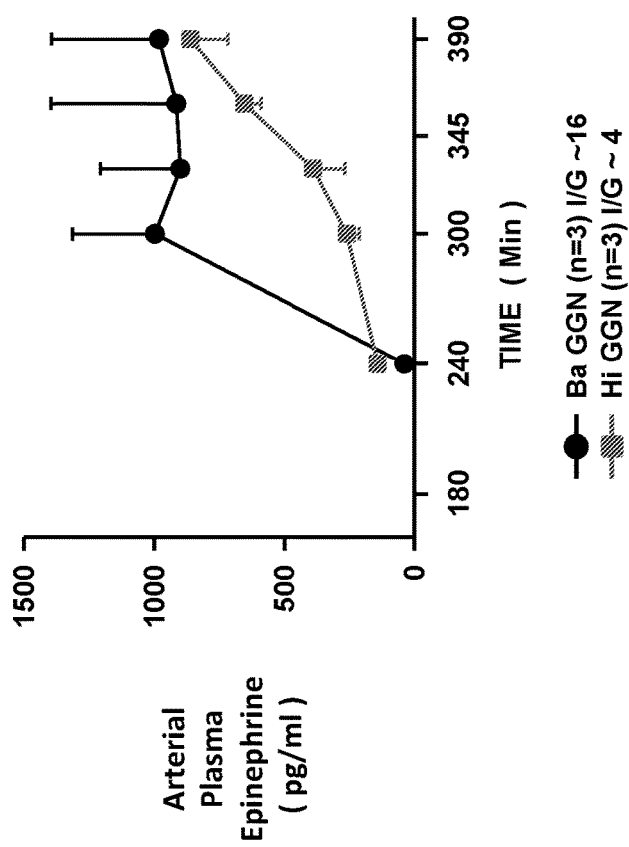
Figure 65B:
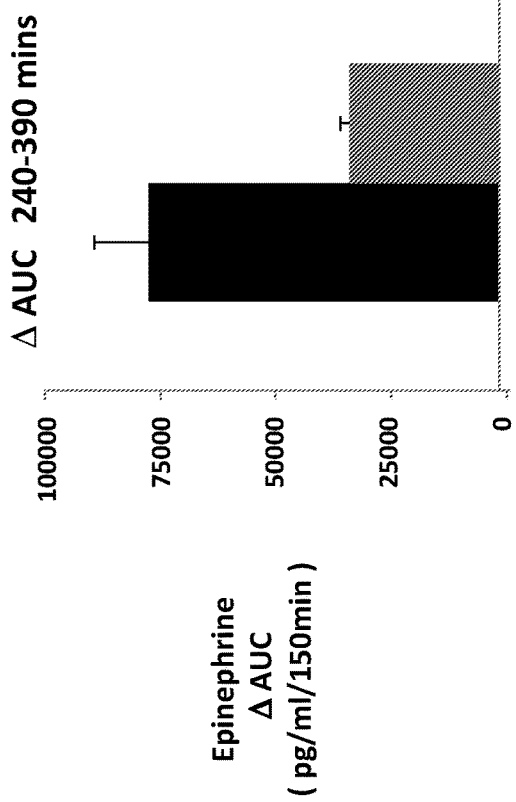
Figure 65C:
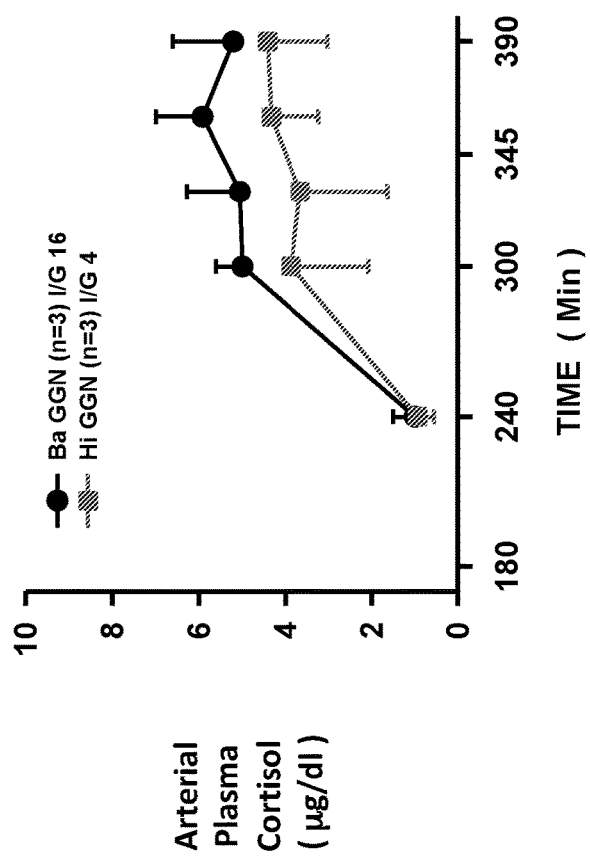
Figure 65D:
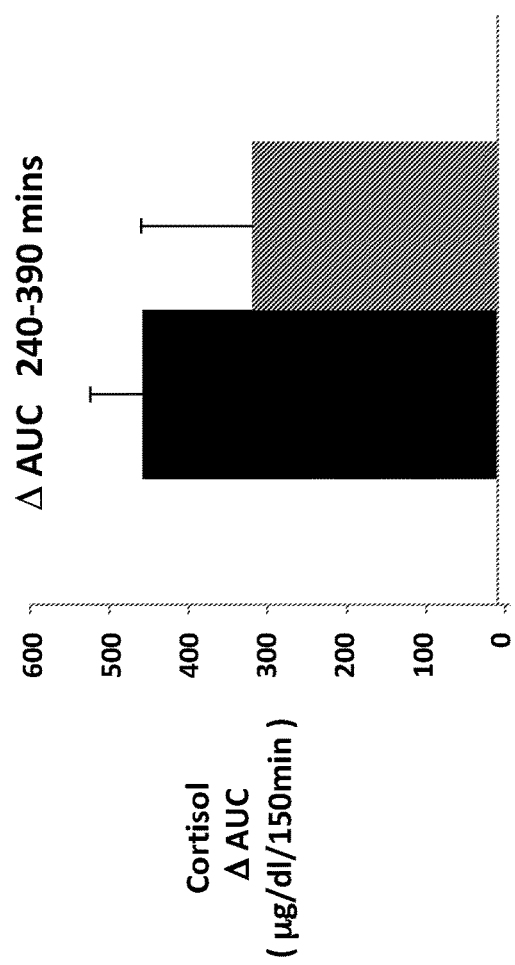

FIGS. 64A-C illustrate data that relate to glucose concentration during co-infusion of insulin and glucagon of the present inventive concepts. Insulin was infused at a rate of 0.4 mU/kg/min and glucagon was infused at a rate of 2.1 ng/kg/min. During the priming and basal replacements periods from 0-180 min, the I/G molar ratio was 4. At the commencement of the insulin challenge period at 180 min, insulin infusion was increased 4-fold to 1.6 mU/kg/min, while glucagon was either increased 4-fold to 8.4 ng/kg/min (an I/G molar ratio of 4, referred to as the Hi GGN group) or kept basal at 2.1 ng/kg/min (an I/G molar ratio of 16, referred to as the Ba GGN group). As shown in FIG. 64A, the plasma glucose level was stable at ~100 mg/dL during the basal hormone replacement period from 120-180 min, indicating that infusion of subcutaneous insulin at a rate of 0.4 mU/kg/min and glucagon at a rate of 2.1 ng/kg/min can successfully replace endogenous insulin and glucagon secretion. However, when glucagon remained basal with an I/G molar ratio of 16, the plasma glucose level decreased over 90 min and plateaued at ~41 mg/dL during the last 1 hour of the experiment. As shown in FIGS. 64A and B, when the I/G molar ratio was maintained at 4, the glucose level decreased much more slowly and averaged ~46 mg/dL during the last 1 hour of the experiment. As shown in FIG. 64C, glucose was infused at a rate of ~0.8 mg/kg/min in the Ba GGN group to prevent the plasma glucose levels from decreasing below 40 mg/dL. The glucose infusion and the time dependent 44% fall (from peak) in glucagon in the Hi GGN group both caused the data to underestimate the hypoglycemic protection afforded by the glucagon. The data nevertheless shows that the presence of extra glucagon minimizes the hypoglycemic effect of insulin.

FIGS. 65A-D illustrate data that relate to epinephrine and cortisol concentrations during co-infusion of insulin and glucagon of the present inventive concepts. Insulin was infused at a rate of 1.6 mU/kg/min. Glucagon was infused at a rate of 4-fold basal at 8.4 ng/kg/min (an I/G molar ratio of 4, referred to as the Hi GGN group) or kept basal at 2.1 ng/kg/min (an I/G molar ratio of 16, referred to as the Ba GGN group). In the presence of extra glucagon, the increase in epinephrine and cortisol levels (e.g. resulting from activation of the central nervous system) were reduced by ~50% and 30%, respectively. Additionally, an improvement in glycemia was observed despite the reduced engagement of the central nervous system. This shows that there is an increased availability of the central nervous system for further defense of the blood sugar.

Figure 66A:
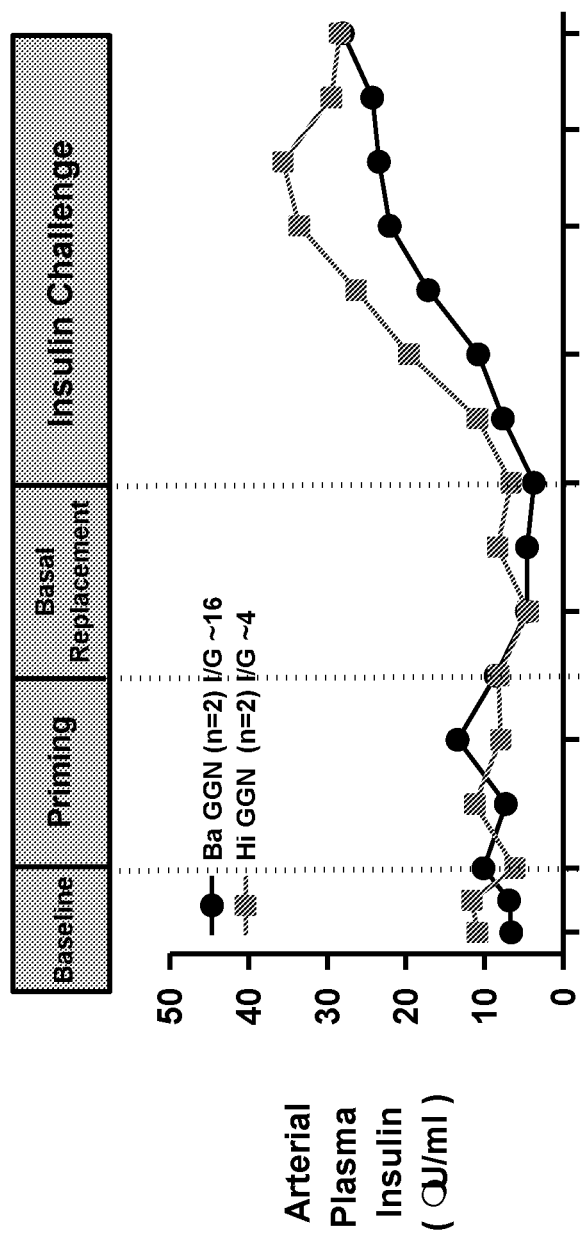
FIGS. 66 and 67 illustrate data from mammalian studies conducted by applicant to determine if maintaining an I/G molar ratio of 4 while reducing the basal replacement rates of insulin and glucagon maintains euglycemia, consistent with the present inventive concepts.
Figure 66B:
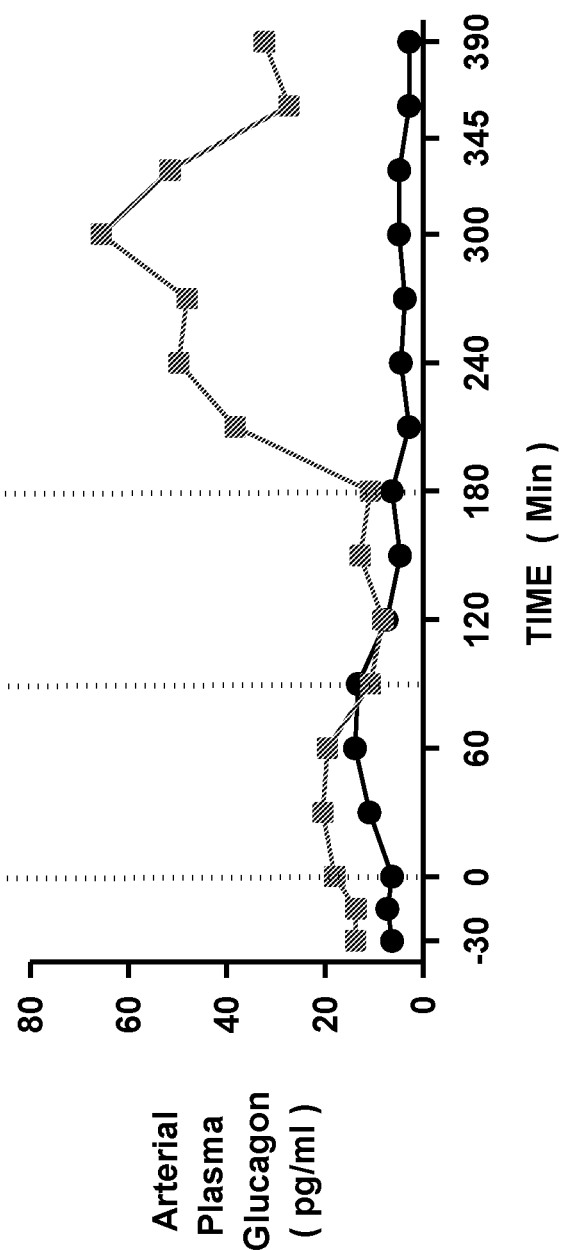
Figure 67B:
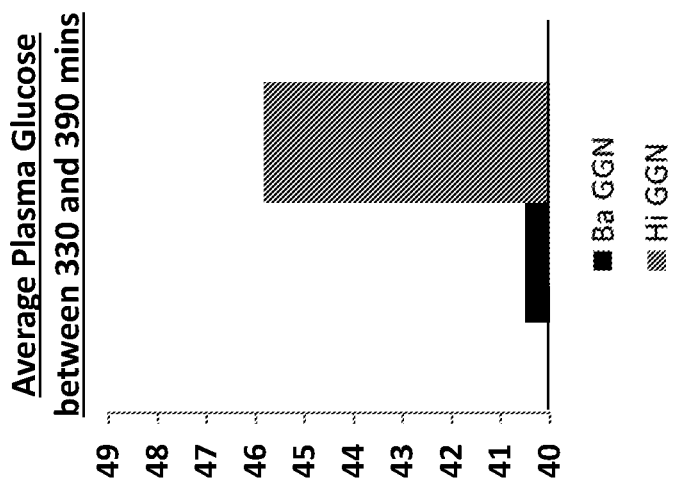

Referring now to FIGS. 66 and 67, results from studies conducted by applicant are presented, consistent with the present inventive concepts. These studies were conducted to determine whether maintaining an I/G molar ratio of 4 while reducing the basal replacement rates of insulin and glucagon would still maintain euglycemia. This is important given that insulin sensitivity can vary between individuals and not all animals require the same basal replacement rate of insulin and glucagon.

FIGS. 66A and B illustrate data that relate to hormone concentrations during co-infusion of insulin and glucagon of the present inventive concepts. Insulin was infused at a rate of 0.32 mU/kg/min and glucagon was infused at a rate of 1.68 ng/kg/min. During the priming and basal replacements periods from 0-180 min, the I/G molar ratio was 4. At the commencement of the insulin challenge period at 180 min, insulin infusion was increased 4-fold to 1.28 mU/kg/min, while glucagon was either increased 4-fold to 6.72 ng/kg/min (an I/G molar ratio of 4, referred to as the Hi GGN group) or kept basal at 1.68 ng/kg/min (an I/G molar ratio of 16, referred to as the Ba GGN group). As shown in FIG. 66A, the insulin level during the last 1 hour of the basal hormone replacement period averaged only 6 µU/mL, consistent with the reduced insulin infusion rate. As shown in FIG. 66B, the glucagon level during the last 1 hour of the basal hormone replacement period averaged only ~9 pg/mL, consistent with the reduced glucagon infusion.

Figure 67A:
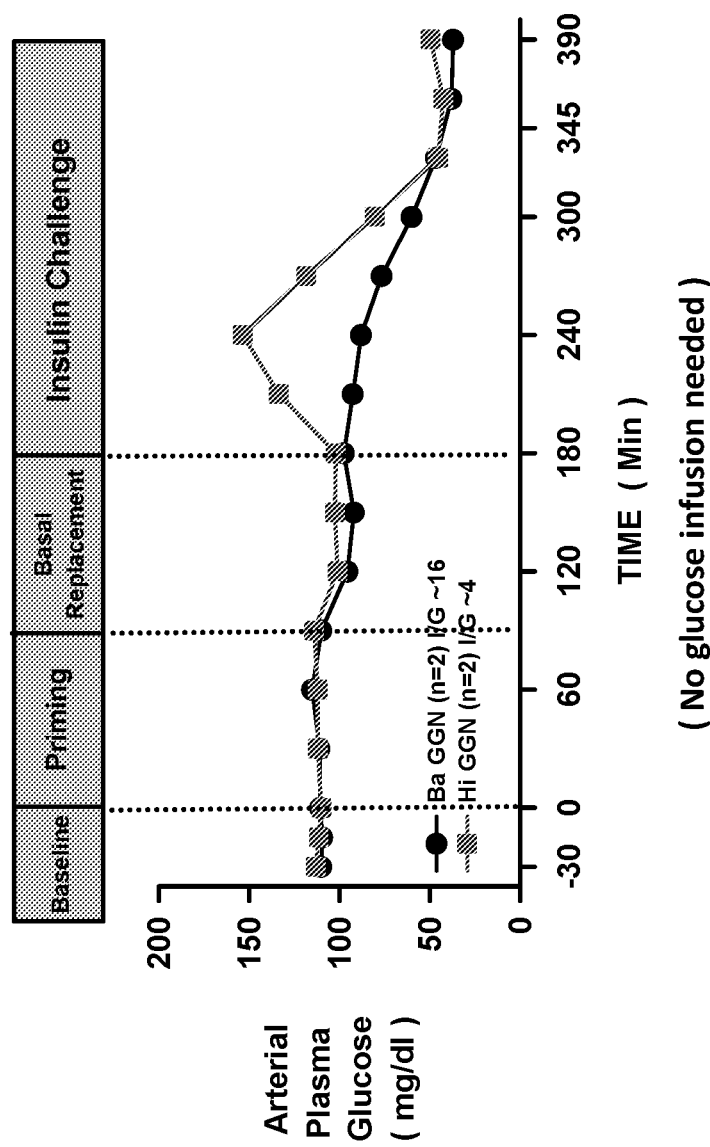

FIGS. 67A and B illustrate data that relate to glucose concentration during co-infusion of insulin and glucagon of the present inventive concepts. Insulin was infused at a rate of 0.32 mU/kg/min and glucagon was infused at a rate of 1.68 ng/kg/min. During the priming and basal replacements periods from 0-180 min, the I/G molar ratio was 4. At the commencement of the insulin challenge period at 180 min, insulin infusion was increased 4-fold to 1.28 mU/kg/min, while glucagon was either increased 4-fold to 6.72 ng/kg/min (an I/G molar ratio of 4, referred to as the Hi GGN group) or kept basal at 1.68 ng/kg/min (an I/G molar ratio of 16, referred to as the Ba GGN group). As shown in FIGS. 67A and B, the plasma glucose level during the basal hormone replacement period was nearly identical to that as described hereabove in reference to FIG. 64. This data suggests that since the plasma level of both insulin and glucagon were reduced, the effects of the reductions in infusion offset one another. The 4-fold increase in insulin (e.g. to 1.28 mU/kg/min) in the absence of a rise in glucagon caused a slow decrease in plasma glucose to a final level of 37 mg/dL at 390 min. An accompanying 4-fold increase in glucagon caused a slow decrease in plasma glucose to a final level of ~50 mg/dL at 390 min. Therefore, the co-administration of insulin and glucagon of the present inventive concepts at an I/G molar ratio of 4 affords protection against hypoglycemia even when one modestly alters (~20%) the absolute basal replacement rate of insulin and glucagon, as might be required for a given individual.

Referring now to FIGS. 68 and 69, results from studies conducted by applicant are presented, consistent with the present inventive concepts. In these studies, the ability of insulin infusion at a rate of 0.4 mU/kg/min and glucagon infusion at a rate of 1.38 ng/kg/min (an I/G molar ratio of 6) to effectively replace basal secretion of insulin and glucagon and to limit insulin-induced hypoglycemia was assessed, consistent with the present inventive concepts.

FIGS. 68A and B, illustrate data that relate to hormone concentrations during co-infusion of insulin and glucagon of the present inventive concepts. Insulin was infused at a rate of 0.4 mU/kg/min and glucagon was infused at a rate of 1.38 ng/kg/min. During the priming and basal replacements periods from 0-180 min, the I/G molar ratio was 6. At the commencement of the insulin challenge period at 180 min, insulin infusion was increased 4-fold to 1.6 mU/kg/min, while glucagon was either increased 4-fold to 5.56 ng/kg/min (an I/G molar ratio of 6, referred to as the Hi GGN group) or kept basal at 1.39 ng/kg/min (an I/G molar ratio of 24, referred to as the Ba GGN group). As shown in FIG. 68A, during the basal hormone replacement period, the insulin levels were similar to those as described hereabove in reference to FIG. 61. The increase in insulin levels, which occurred in response to the 4-fold increase in its infusion rate, also approached the levels similar to those as described hereabove in reference to FIG. 61. As shown in FIG. 68B, the glucagon levels increased less with the infusion rate of 1.38 ng/kg/min as compared to an infusion rate of 2.1 ng/kg/min during both the basal hormone replacement period and when the glucagon infusion rate was increased 4-fold.

Figure 69B:
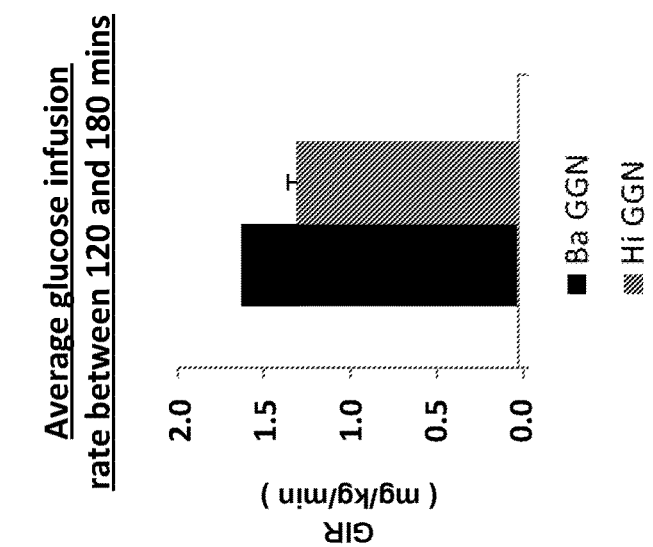
Figure 69A:
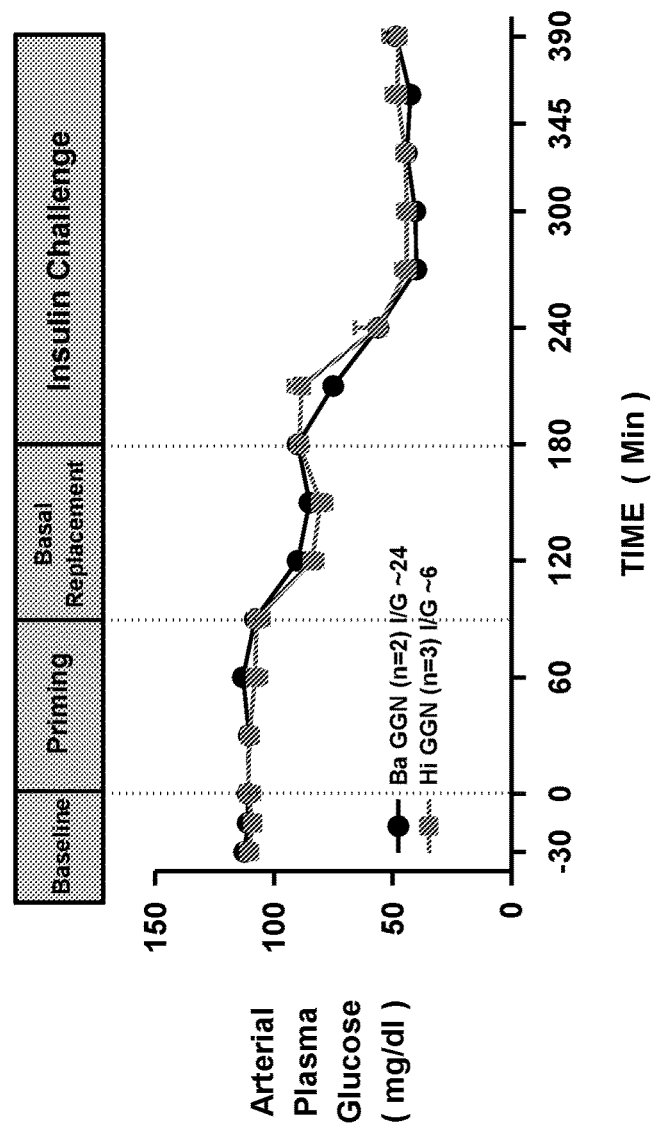
Figures 69C, 69D:
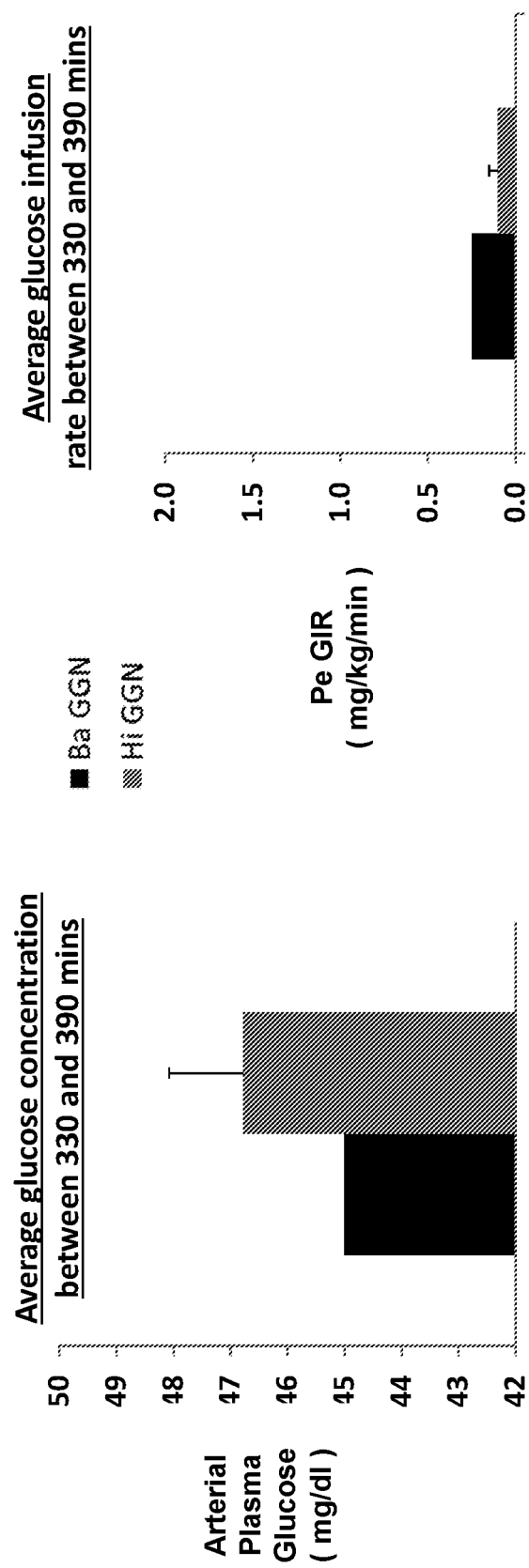

FIGS. 69A-D illustrate data that relate to glucose concentration during co-infusion of insulin and glucagon of the present inventive concepts. Insulin was infused at a rate of 0.4 mU/kg/min and glucagon was infused at a rate of 1.38 ng/kg/min. During the priming and basal replacements periods from 0-180 min, the I/G molar ratio was 6. At the commencement of the insulin challenge period at 180 min, insulin infusion was increased 4-fold to 1.6 mU/kg/min, while glucagon was either increased 4-fold to 5.52 ng/kg/min (an I/G molar ratio of 6, referred to as the Hi GGN group) or kept basal at 1.38 ng/kg/min (an I/G molar ratio of 24, referred to as the Ba GGN group). As shown in FIG. 69A, with an I/G molar ratio of 6, the plasma glucose level in the basal hormone replacement period decreased to 80 mg/dL. As shown in FIG. 69B, glucose was infused to prevent the plasma glucose level from decreasing further (e.g. below 80 mg/dL). As shown in FIGS. 69C and D, the protection from insulin-induced hypoglycemia was 2 mg/dL despite slightly more glucose being infused in the basal glucose group.

Referring now to FIGS. 70-73, results from studies conducted by applicant are presented, consistent with the present inventive concepts. These studies were conducted to support the development of a co-formulation of insulin and glucagon containing non-aqueous co-solvent for use in infusion pumps, such as pump 100 of system 10 described here above, that is compatible with pumping systems and stable at 2-8° C., as well as under agitation conditions. Challenges included the solubility of insulin and glucagon in a non-aqueous solution co-formulation with organic solvents, as well as the co-formulation's compatibility with infusion pump 100. With an objective of achieving improved solubility and stability, two approaches were employed: pure organic solvents, such as acetone, benzyl alcohol, benzyl benzoate, dimethyl sulfoxide (DMSO), ethanol, ethyl acetate, glycerol, methanol, N-methylpyrrolidone (NMP), polyethylene glycol, and propylene glycol (PG); and co-solvents, such as a solution of organic solvents mixed with aqueous solution, as well as the addition of primary co-solvent mixtures plus additives.

These studies were conducted with a target concentration of insulin of between 1 to 10 mg/mL and a target concentration of glucagon of between 0.1 and 1.0 mg/mL, more specifically insulin concentration from 3 to 5 mg/mL and glucagon concentration from 0.1 to 0.8 mg/mL. A basal insulin rate of U-100 between 10-20 µL/hr, and an I/G molar ratio of 3 to 16 with a fixed insulin dose were assumed.

FIGS. 70 and 70A-C illustrate data related to three co-formulations of insulin and glucagon in DMSO as administered to canine subjects. To determine the concentrations of co-formulations, samples were diluted with 0.01 N HCl, then analyzed by reversed-phase high-performance liquid chromatography (RP-HPLC) method. The retention time of insulin and glucagon is at 10.7 min and 14.6 min, respectively. As shown in FIG. 70, co-formulation AB-160003-01 comprises 4.48 mg/mL of insulin and 0.83 mg/mL of glucagon, co-formulation AB-160002-01 comprises 4.48 mg/mL of insulin and 0.21 mg/mL of glucagon, and co-formulation AB-160001-01 comprises 1.08 mg/mL of insulin and 0.21 mg/mL of glucagon. The molar ratio comprises 3 for both co-formulation AB-160003-01 and AB-160001-01. The molar ratio comprises 12 for co-formulation AB-160002-01.

An agitation study was conducted for a co-formulation in DMSO comprising 1.0 mg/mL of insulin and 0.5 mg/mL of glucagon. Aliquoted samples were placed in three conditions up to 7 days: 5° C. with 0 rpm (as control), 25° C. with 50 rpm, and 37° C. with 50 rpm. Samples were diluted with 0.01N HCl, then analyzed by RP-HPLC. The recovery of active (insulin and glucagon) was calculated and listed in table below. Both insulin and glucagon showed good recovery after 7 days agitation.

netetraacetic acid (EDTA). Target concentrations of insulin were observed in all co-solvents comprising 34.5-35.5% PB. Additionally, target concentrations of glucagon were observed in a first co-solvent comprising 34.5-35.5% PBS, 4.5% vitamin E TPGS, 30% DMSO, and 30% PG, and second co-solvent comprising 34.5-35.5% PBS, 4.5% vitamin E TPGS, 30% DMSO, and 30% glycerol.

FIG. 73 illustrates data related to the solubility of insulin and glucagon, respectively, in co-solvents comprising non-aqueous organic solvents mixed with up to 40% aqueous PB (pH 7.8). The co-solvents comprise at least one of the following organic solvents: NMP; PG; glycerol; and DMSO, consistent with the present inventive concepts, where the co-solvent or co-solvent mixture comprises at least 60% of the formulation. The concentrations of insulin and glucagon in the supernatant were analyzed by RP-HPLC. In a solution comprising 30% or greater of an organic solvent, glucagon

| | Glucagon | | | Insulin | | |
|---|---|---|---|---|---|---|
| Time (day) | 37° C., 50 rpm | 25° C., 50 rpm | 5° C., 0 rpm | 37° C., 50 rpm | 25° C., 50 rpm | 5° C., 0 rpm |
| 0 | 100.0% | 100.0% | 100.0% | 100.0% | 100.0% | 100.0% |
| 3 | 96.6% | 97.5% | 100.4% | 96.0% | 99.2% | 99.6% |
| 5 | 97.6% | 95.0% | 100.8% | 95.6% | 98.9% | 103.6% |
| 7 | 94.0% | 95.4% | 96.1% | 91.8% | 97.1% | 100.1% |

Figures 71A, 71B:
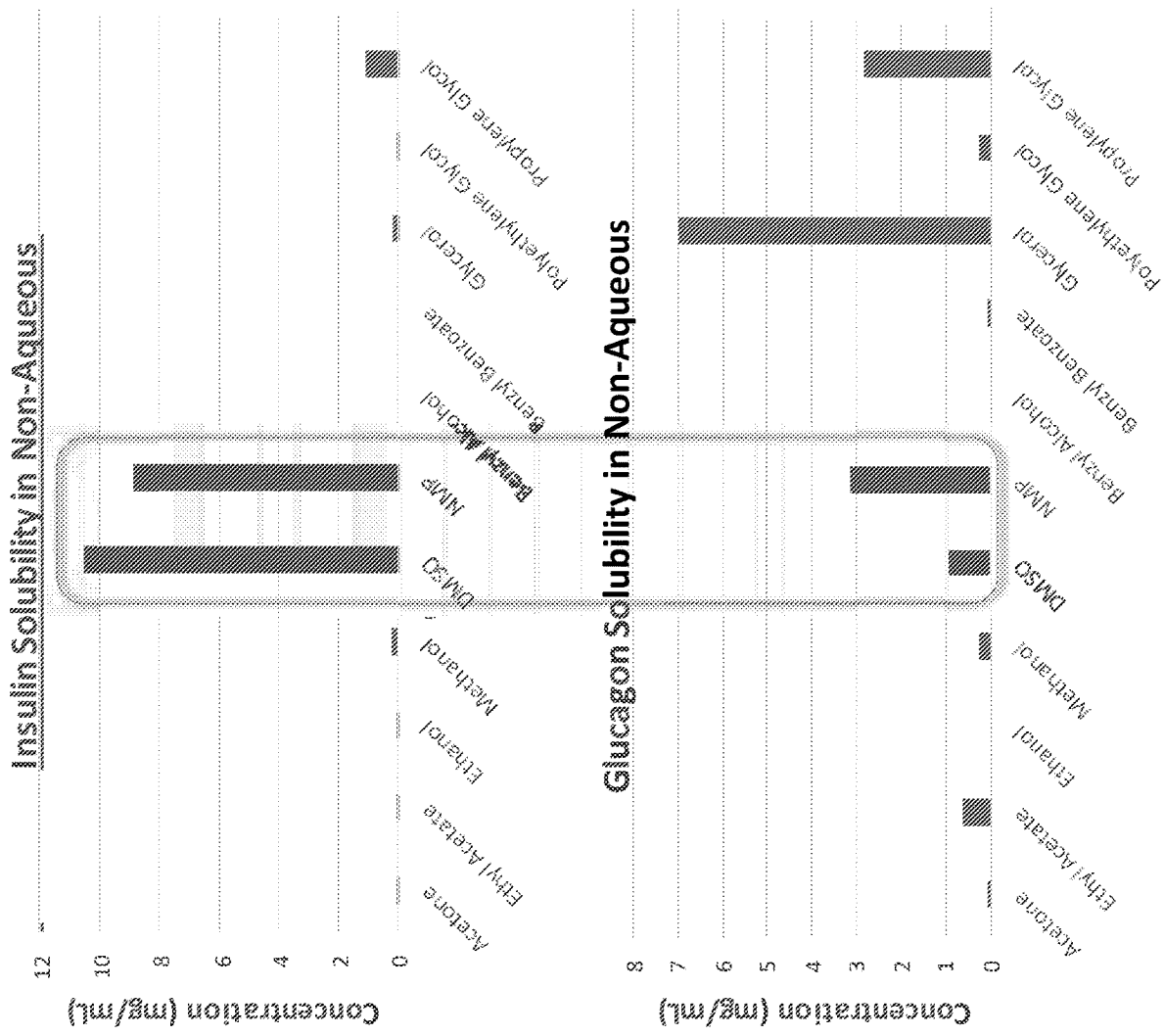

FIGS. 71A and B illustrate data related to the solubility of insulin and glucagon, respectively, in non-aqueous solvents, consistent with the present inventive concepts. The concentrations of insulin and glucagon in the supernatant were analyzed by RP-HPLC. As shown in FIGS. 71A and B, both DMSO and NMP indicate good solubility for insulin (e.g. a concentration greater than 8 mg/mL) and glucagon (e.g. a concentration greater than 1 mg/mL). Both glycerol and propylene glycol indicate good solubility for glucagon (e.g. a concentration greater than 2.5 mg/mL), but poor solubility for insulin (e.g. a concentration less than 2 mg/mL). Non-aqueous solvents with a dielectric constant between 25 and 70 have a relatively higher solubility for glucagon, for example, solvents (dielectric constants in parenthesis) such as N-methylpyrrolidone (32), methanol (33), N,N-dimethyl formamide (37), acetonitrile (38), dimethyl acetamide (38), DMSO (47), propylene carbonate (65).

FIGS. 72A and B illustrate data related to the solubility of a co-formulation of insulin and glucagon in co-solvents comprising non-aqueous organic solvents mixed with phosphate buffer saline (PBS) or phosphate buffer (PB), and vitamin E TPGS, consistent with the present inventive concepts, where the non-aqueous organic co-solvent comprised at least 60% of the formulation. The concentrations of insulin and glucagon in the supernatant were analyzed by RP-HPLC. In a solution comprising 60% organic solvent, glucagon demonstrated a better solubility in PB. As shown in FIG. 72A, the solubility of an insulin and glucagon co-formulation, comprising 75-95% PBS, were observed when mixed with at least one of the following co-solvents: 5% vitamin E TPGS; 10% DMSO; 10% NMP; 10% PG; and 10% glycerol. When mixed with 95% PBS and 5% vitamin E TPGS, the individual DS solubility of insulin was 1.38 mg/mL and glucagon was 0.25 mg/mL. As shown in FIG. 72B, the solubility of an insulin and glucagon co-formulation of the present inventive concepts, comprising 34.5-35.5% PB, was observed when mixed with at least one of the following co-solvents: 4.5% vitamin E TPGS; 30% DMSO; 30% NMP; 30% PG; 30% glycerol; and 1% ethylenediamidemonstrated a better solubility (e.g. 0.1-0.3 mg/mL) in PB as opposed to glucagon's solubility in 100% PB (e.g. less than 0.02 mg/mL). Insulin demonstrated target concentrations in all co-solvents tested where the organic co-solvent comprised greater than 30% of the mixture.

Figure 74:
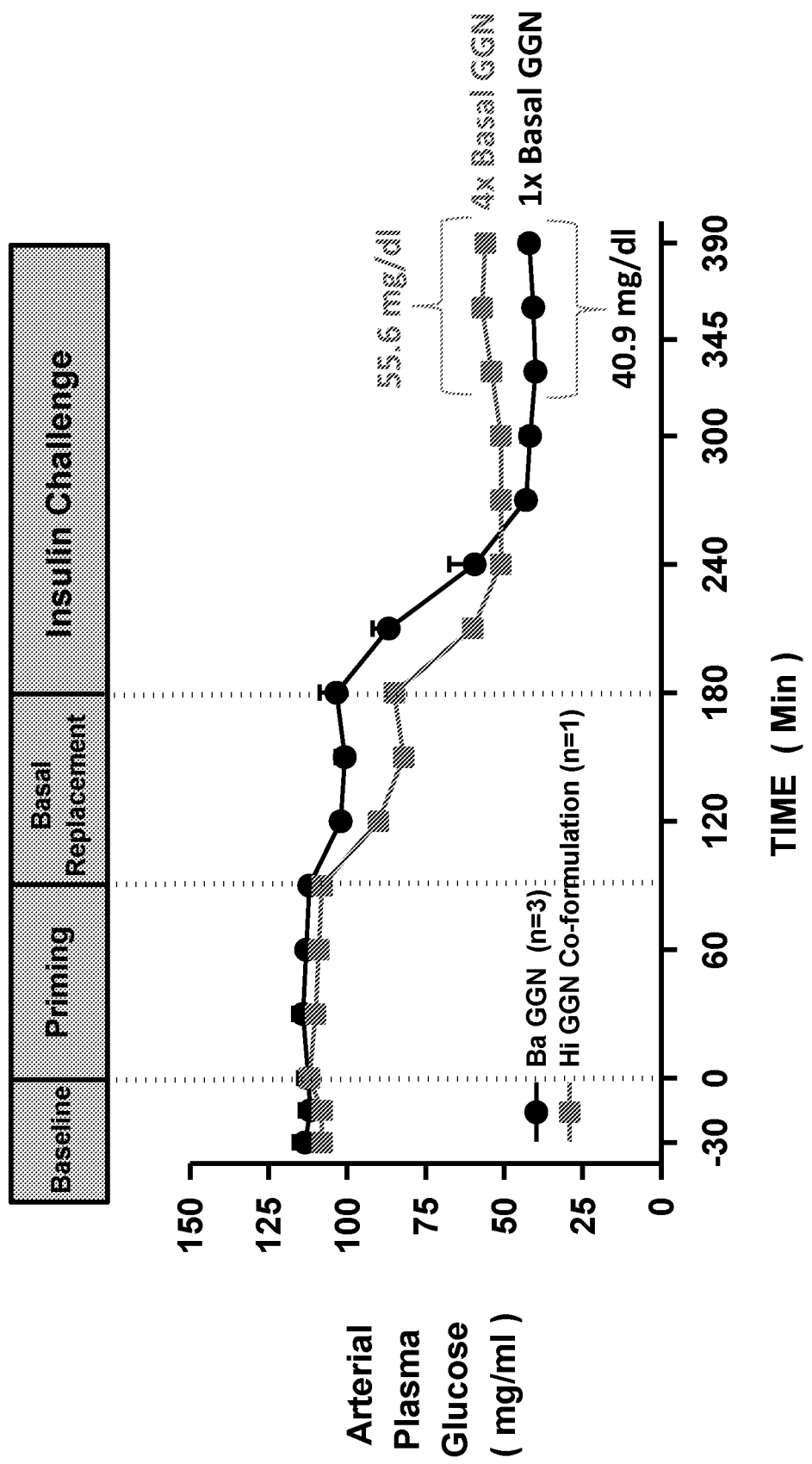

Referring now to FIGS. 74-76, results from studies conducted by applicant are presented, consistent with the present inventive concepts. These studies were conducted on canine subjects to assess the therapeutic value of a co-formulated insulin and glucagon solution as compared to insulin and glucagon as separate solutions.

A co-formulation of insulin and glucagon was prepared by diluting a stock solution of glucagon in DMSO with PG and PB (pH 7.4), followed by the addition of insulin. The glucagon DMSO stock solution was prepared by dissolving glucagon in DMSO at a concentration of 0.55 mg/mL and diluted to 0.12 mg/mL with PG, followed by PB (e.g. 20 mM, pH 7.4) at a volume ratio of 4:2:4 (glucagon DMSO stock solution: PG: PB). A desired quantity of insulin was added into the glucagon solution (e.g. 0.12 mg/mL) to achieve an insulin concentration of 0.83 mg/mL. The molar ratio of insulin to glucagon is 4. The final co-formulation was observed to be clear and colorless.

The concentrations of insulin and glucagon in the co-formulation were analyzed by RP-HPLC. A sample of the co-formulation was diluted with 0.01N HCl. The diluted co-formulation was analyzed using an Agilent HPLC, equipped with Diode Array Detector (DAD), and further comprising a Zorbax SB-C8 of 5 μm, a 4.6×250 mm column flow rate of 1 mL/min, an ultraviolet detection of 214 nm, and an injection volume of 50 μl. The column temperature was maintained at 30° C. and the sample chamber was maintained at 5° C. The mobile phase consisted of a combination of 0.1% trifluoroacetic acid (TFA) in Milli-Q water (mobile phase A) and 0.1% TFA in acetonitrile (mobile phase B). The mobile phase combination began with 70% of mobile phase A isocratic for 5 min, then decreased to 60% of mobile phase A at a rate of 0.5% per min, and followed by a column wash at a higher percentage of mobile phase B for 5 min.

FIG. 74 illustrates data related to the plasma glucose levels during an infusion of the co-formulation as compared to a co-infusion of insulin and glucagon as separate solutions. During the 90-390 min period, somatostatin was administered to the canine subjects to disable the endocrine pancreas. During the 0-180 min period, insulin at a rate of 0.4 mU/kg/min and glucagon at a rate of 2.1 ng/kg/min were infused subcutaneously in basal amounts, either as separate solutions (referred to as the Ba GGN group) or as a co-formulation (referred to as the Hi GGN group). At 180 min, the insulin infusion rate was increased to 1.6 mU/kg/min for both the Ba GGN and Hi GGN group. The glucagon infusion rate was kept basal in the Ba GGN group, but was increased to 8.4 ng/kg/min in the Hi GGN group.

During the basal hormone replacement period from 90-180 min, the glucose level was 100 mg/dL in the Ba GGN group. The glucose level was closer to 80 mg/dL in the Hi GGN group, thereby indicating a predominance of insulin action in the co-formulation. During the insulin challenge period from 180-390 min, the glucose level decreased to 41 mg/dL in the Ba GGN group with an I/G molar ratio of 16. When the glucagon level was increased 4-fold to maintain an I/G molar ratio of 4 (as shown in FIG. 76) the glucose level decreased to only 56 mg/dL in the Hi GGN group.

FIG. 75 illustrates data related to the arterial insulin levels during an infusion of insulin in the co-formulation or as a separate solution. During the priming and basal replacement period from 0-180 min, insulin was infused subcutaneously at a rate of 0.4 mU/kg/min, either as a single solution (referred to as the Ba GGN group) or in a co-formulation with glucagon (referred to as the Hi GGN group). During the challenge period from 180-390 min, insulin was infused subcutaneously at a rate of 1.6 mU/kg/min in both the Ba GGN and Hi GGN groups, with the former being in co-formulation with glucagon. The insulin levels increased similarly in both groups.

FIG. 76 illustrates data related to the arterial glucagon levels during an infusion of the co-formulation as compared to an infusion of glucagon as a separate solution. Glucagon was infused subcutaneously at a rate of 2.1 ng/kg/min for the entire experiment from 0-390 min as a single solution in the Ba GGN group. Glucagon was infused at rate of 2.1 ng/kg/min in a co-formulation with insulin during the first 180 min in the Hi GGN group. During the insulin challenge period from 180-390 min, glucagon was infused subcutaneously at a rate of 8.4 ng/kg/min in co-formulation with insulin in the Hi GGN group. The glucagon levels increased ~4-fold.

During the experiments shown in FIGS. 75 and 76, during the priming and replacement periods from 0-180 min, the I/G molar ratio was 4 in both groups. During the insulin challenge period from 180-390 min, the I/G molar ratio increased to 16 in the Ba GGN group and remained at 4 in the Hi GGN group.

Aspects of the present disclosure may be further embodied in the inventions set forth in the following clauses:

Clause 1: A method of treatment comprising co-administering insulin and glucagon to a subject, wherein the insulin and glucagon are co-administered at an insulin:glucagon molar ratio between about 1:1 and about 6:1, and wherein the insulin and glucagon are administered in an amount therapeutically effective to simultaneously treat or inhibit hyperglycemia and to inhibit hypoglycemia.

Clause 2: The method of clause 1, wherein the subject is hyperglycemic prior to co-administering the insulin and the glucagon.

Clause 3: The method of either clause 1 or clause 2, wherein co-administering the insulin and the glucagon comprises administering to the subject a co-formulation comprising insulin and glucagon.

Clause 4: The method of clause 3, wherein the co-formulation comprises insulin at a concentration between about 1 mg/ml and about 10 mg/ml, and glucagon at a concentration between about 0.1 mg/ml and about 1 mg/ml.

Clause 5: The method of either clause 3 or clause 4, wherein the co-formulation comprises insulin at a concentration between about 3 mg/ml and about 5 mg/ml, and glucagon at a concentration between about 0.1 mg/ml and about 0.8 mg/ml.

Clause 6: The method of any of clauses 3-5, wherein the co-formulation comprises a solvent that includes one or more non-aqueous solvents.

Clause 7: The method of clause 6, wherein between about 20% and about 60% of the solvent (v/v) consists of the one or more non-aqueous solvents.

Clause 8: The method of either clause 6 or clause 7, wherein at least one non-aqueous solvent is dimethyl sulfoxide (DMSO) or N-methylpyrrolidone (NMP).

Clause 9: The method of any of clauses 6-8, wherein the solvent further includes one or more aqueous solvents.

Clause 10: The method of claim 9, wherein no more than about 40% of the solvent (v/v) consists of the one or more aqueous solvents.

Clause 11: The method of any of clauses 6-10, wherein between about 10% and about 40% of the solvent (v/v) is propylene glycol (PG), glycerol, or a combination of PG and glycerol.

Clause 12: The method of any of clauses 3-10, wherein the co-formulation of insulin and glucagon has adequate in-use stability for patient handling as an injection or in an infusion pump.

Clause 13: The method of any of the preceding clauses, wherein co-administering the insulin and the glucagon comprises administering the insulin and the glucagon subcutaneously.

Clause 14: The method of any of the preceding clauses, wherein the insulin comprises hepato-preferential insulin.

Clause 15: The method of any of the preceding clauses, wherein the insulin and glucagon are co-administered at an insulin:glucagon molar ratio between about 1:1 and about 5:1.

Clause 16: The method of any of the preceding clauses, wherein the insulin and glucagon are co-administered at an insulin:glucagon molar ratio between about 3:1 and about 6:1.

Clause 17: The method of any of the preceding clauses, wherein the insulin and glucagon are co-administered at an insulin:glucagon molar ratio between about 3:1 and about 5:1.

Clause 18: The method of any of the preceding clauses, wherein co-administering the insulin and glucagon comprises administering the insulin at a basal infusion rate of about 0.2-0.6 mU/kg/minute and administering the glucagon at a basal infusion rate of about 1-4 ng/kg/minute.

Clause 19: The method of clause 18, wherein co-administering the insulin and glucagon comprises administering the insulin at a basal infusion rate of about 0.3-0.5 mU/kg/minute.

Clause 20: The method of either clause 18 or clause 19, wherein co-administering the insulin and glucagon comprises administering the glucagon at a basal infusion rate of about 2-3 ng/kg/minute.

Clause 21: The method of any of the preceding clauses, wherein the insulin comprises an insulin analog.

Clause 22: The method of any of the preceding clauses, wherein the glucagon comprises a glucagon analog.

Clause 23: The method of any of the preceding clauses, wherein the subject has type-1, type-2, gestational, or other forms of diabetes mellitus.

Clause 24, wherein when the insulin and glucagon are co-administered, the subject is presenting hypoglycemia associated autonomic failure.

Clause 25: A co-formulation comprising insulin at a concentration between about 1 mg/ml and about 10 mg/ml, and glucagon at a concentration between about 0.1 mg/ml and about 1 mg/ml, wherein the molar ratio of insulin:glucagon is between about 1:1 and about 6:1.

Clause 26: The co-formulation of clause 25, wherein the molar ratio of insulin:glucagon is between about 1:1 and about 5:1.

Clause 27: The co-formulation of either clause 25 or clause 26, wherein the molar ratio of insulin:glucagon is between about 3:1 and about 6:1.

Clause 28: The co-formulation of any of clauses 25-27, wherein the molar ratio of insulin:glucagon is between about 3:1 and about 5:1.

Clause 29: The co-formulation of any of clauses 25-28, wherein the insulin is at a concentration between about 3 mg/ml and about 5 mg/ml, and the glucagon is at a concentration between about 0.1 mg/ml and about 0.8 mg/ml.

Clause 30: The co-formulation of any of clauses 25-29, further comprising a solvent that includes one or more aqueous solvents and one or more non-aqueous solvents.

Clause 31: The co-formulation of clause 30, wherein between about 20% and about 60% of the solvent (v/v) consists of the one or more non-aqueous solvents, and no more than about 40% of the solvent (v/v) consists of the one or more aqueous solvents.

Clause 32: The method of either clause 30 or clause 31, wherein at least one non-aqueous solvent is dimethyl sulfoxide (DMSO) or N-methylpyrrolidone (NMP).

Clause 33: The method of any of clauses 30-32, wherein between about 10% and about 40% of the solvent is propylene glycol (PG), glycerol, or a combination of PG and glycerol.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of treatment comprising co-administering insulin and glucagon to a subject, wherein the insulin and glucagon are co-administered at an insulin:glucagon molar ratio between about 1:1 and about 6:1, wherein the insulin and glucagon are administered in an amount therapeutically effective to simultaneously treat or inhibit hyperglycemia and to inhibit hypoglycemia;
   wherein co-administering the insulin and glucagon comprises administering the insulin at a basal infusion rate of about 0.2-0.6 mU/kg/minute and administering the glucagon at a basal infusion rate of about 1-4 ng/kg/minute; and, wherein the insulin basal infusion rate and the glucagon basal infusion rate are increased by 4- to 5-fold at initiation of a meal.

2. The method of claim 1, wherein the subject is hyperglycemic prior to co-administering the insulin and the glucagon.

3. The method of claim 1, wherein co-administering the insulin and the glucagon comprises administering to the subject a co-formulation comprising insulin and glucagon.

4. The method of claim 3, wherein the co-formulation comprises insulin at a concentration between about 1 mg/ml and about 10 mg/ml, and glucagon at a concentration between about 0.1 mg/ml and about 1 mg/ml.

5. The method of claim 3, wherein the co-formulation comprises insulin at a concentration between about 3 mg/ml and about 5 mg/ml, and glucagon at a concentration between about 0.1 mg/ml and about 0.8 mg/ml.

6. The method of claim 3, wherein the co-formulation comprises a solvent that includes one or more non-aqueous solvents.

7. The method of claim 6, wherein between about 20% and about 60% of the solvent (v/v) consists of the one or more non-aqueous solvents.

8. The method of claim 6, wherein at least one non-aqueous solvent is dimethyl sulfoxide (DMSO) or N-methylpyrrolidone (NMP).

9. The method of claim 6, wherein the solvent further includes one or more aqueous solvents.

10. The method of claim 9, wherein no more than about 40% of the solvent (v/v) consists of the one or more aqueous solvents.

11. The method of claim 6, wherein between about 10% and about 40% of the solvent is propylene glycol (PG), glycerol, or a combination of PG and glycerol.

12. The method of claim 3, wherein the co-formulation of insulin and glucagon has adequate in-use stability for patient handling as an injection or in an infusion pump.

13. The method of claim 1, wherein co-administering the insulin and the glucagon comprises administering the insulin and the glucagon subcutaneously.

14. The method of claim 1, wherein the insulin comprises hepato-preferential insulin.

15. The method of claim 1, wherein the insulin and glucagon are co-administered at an insulin:glucagon molar ratio between about 1:1 and about 5:1.

16. The method of claim 1, wherein the insulin and glucagon are co-administered at an insulin:glucagon molar ratio between about 3:1 and about 6:1.

17. The method of claim 1, wherein the insulin and glucagon are co-administered at an insulin:glucagon molar ratio between about 3:1 and about 5:1.

18. The method of claim 1, wherein co-administering the insulin and glucagon comprises administering the insulin at a basal infusion rate of about 0.3-0.5 mU/kg/minute.

19. The method of claim 1, wherein co-administering the insulin and glucagon comprises administering the glucagon at a basal infusion rate of about 2-3 ng/kg/minute.

20. The method of claim 1, wherein the insulin comprises an insulin analog.

21. The method of claim 1, wherein the glucagon comprises a glucagon analog.

22. The method of claim 1, wherein the subject has type-1, type-2, gestational, or other forms of diabetes mellitus.

23. The method of claim 22, wherein when the insulin and glucagon are co-administered, the subject is presenting hypoglycemia associated autonomic failure.

* * * * *